US009057053B2

(12) United States Patent
Wernig et al.

(10) Patent No.: US 9,057,053 B2
(45) Date of Patent: Jun. 16, 2015

(54) DIRECT CONVERSION OF CELLS TO CELLS OF OTHER LINEAGES

(75) Inventors: Marius Wernig, Stanford, CA (US); Thomas C. Sudhof, Stanford, CA (US); Thomas Vierbuchen, Stanford, CA (US); Austin Ostermeier, West Plains, MO (US); Zhiping Pang, Stanford, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 0 days.

(21) Appl. No.: 13/522,002

(22) PCT Filed: Jan. 19, 2011

(86) PCT No.: PCT/US2011/021731
§ 371 (c)(1),
(2), (4) Date: Oct. 8, 2012

(87) PCT Pub. No.: WO2011/091048
PCT Pub. Date: Jul. 28, 2011

(65) Prior Publication Data
US 2013/0022583 A1    Jan. 24, 2013

Related U.S. Application Data

(60) Provisional application No. 61/336,309, filed on Jan. 19, 2010.

(51) Int. Cl.
| | |
|---|---|
| *C12N 5/0797* | (2010.01) |
| *C12N 5/071* | (2010.01) |
| *C12Q 1/68* | (2006.01) |

(Continued)

(52) U.S. Cl.
CPC ............ *C12N 5/0619* (2013.01); *C12N 5/0622* (2013.01); *C12N 5/0623* (2013.01); *G01N 33/5058* (2013.01); *C12N 2501/60* (2013.01); *C12N 2506/02* (2013.01);
(Continued)

(58) Field of Classification Search
CPC ........... C12N 2502/99; C12N 2510/00; C12N 5/0622
See application file for complete search history.

(56) References Cited

U.S. PATENT DOCUMENTS

| 7,041,507 B1 | 5/2006 | Levesque et al. |
| 2003/0134413 A1 | 7/2003 | Rathjen et al. |

(Continued)

OTHER PUBLICATIONS

Bussmann; et al. "A robust and highly efficient immune cell reprogramming system", Cell Stem Cell (Nov. 2006), 5 (5):554-66.

(Continued)

*Primary Examiner* — Kimberly A Ballard
*Assistant Examiner* — Aurora M Fontainhas
(74) *Attorney, Agent, or Firm* — Bozicevic, Field & Francis LLP; Pamela J. Sherwood

(57) ABSTRACT

Methods, compositions and kits for producing functional neurons, astroctyes, oligodendrocytes and progenitor cells thereof are provided. These methods, compositions and kits find use in producing neurons, astrocytes, oligodendrocytes, and progenitor cells thereof for transplantation, for experimental evaluation, as a source of lineage- and cell-specific products, and the like, for example for use in treating human disorders of the CNS. Also provided are methods, compositions and kits for screening candidate agents for activity in converting cells into neuronal cells, astrocytes, oligodendrocytes, and progenitor cells thereof.

20 Claims, 18 Drawing Sheets

(51) Int. Cl.
    *G01N 33/536* (2006.01)
    *C12N 5/0793* (2010.01)
    *C12N 5/079* (2010.01)
    *G01N 33/50* (2006.01)

(52) U.S. Cl.
    CPC .... *C12N 2506/1307* (2013.01); *C12N 2506/14* (2013.01); *C12N 2510/00* (2013.01)

(56) References Cited

U.S. PATENT DOCUMENTS

| | | | |
|---|---|---|---|
| 2003/0219894 A1* | 11/2003 | Seino et al. | 435/370 |
| 2008/0233649 A1 | 9/2008 | Seaberg et al. | |
| 2009/0148431 A1 | 6/2009 | Goldman et al. | |

OTHER PUBLICATIONS

Castro; et al. "Proneural bHLH and Brn proteins coregulate a neurogenic program through cooperative binding to a conserved DNA motif", Dev Cell (Dec. 2006), 11(6):831-844.

Chambers; et al. "Highly efficient neural conversion of human ES and iPS cells by dual inhibition of SMAD signaling", Nat Biotechnol (Mar. 2009), 27(3):275-80.

Choi; et al. "MyoD converts primary dermal fibroblasts, chondroblasts, smooth muscle, and retinal pigmented epithelial cells into striated mononucleated myoblasts and multinucleated myotubes", Proc Nat Acad Sci USA (Oct. 1990), 87(20):7988-7992.

Cobaleda; et al. "Conversion of mature B cells into T cells by dedifferentiation to uncommitted progenitors", Nature (Sep. 2007), 449(7161):473-477.

Elkabetz; et al. "Human ES cell-derived neural rosettes reveal a functionally distinct early neural stem cell stage", Genes Dev (Jan. 2008), 22(2):152-165.

Feng; et al. "PU.1 and C/EBPalpha/beta convert fibroblasts into macrophage-like cells", Proc Natl Acad Sci USA (Apr. 2008), 105(16):6057-6062.

Jiang; et al. "Neuroectodermal differentiation from mouse multipotent adult progenitor cells", Nat Acad Sci USA (Sep. 2003), 1:11854-11860.

Johnson; et al. "Functional neural development from human embryonic stem cells: accelerated synaptic activity via astrocyte coculture", J Neurosci (Mar. 2007), 27(12):3069-77.

Kim; et al. "Control of neurogenesis and tyrosine hydroxylase expression in neural progenitor cells through bHLH proteins and Nurr1", Exp Neurol (Feb. 2007), 203(2):394-405.

Koch; et al. "A rosette-type, self-renewing human ES cell-derived neural stem cell with potential for in vitro instruction and synaptic integration", Proc Natl Acad Sci USA (Mar. 2009), 106(9):3225-3230.

Kondo; et al. "Cell-fate conversion of lymphoid-committed progenitors by instructive actions of cytokines", Nature (Sep. 2001), 407(6802):383-386.

Okabe; et al. "Development of neuronal precursor cells and functional postmitotic neurons from embryonic stem cells in vitro", Mech Dev (Sep. 1996), 59(1):89-102.

Roybon; et al. "GABAergic differentiation induced by Mash1 is compromised by the bHLH proteins Neurogenin2, NeuroD1, and NeuroD2", Cereb Cortex (May 2010), 20(5):1234-44.

Shim; et al. "Generation of functional dopamine neurons from neural precursor cells isolated from the subventricular zone and white matter of the adult rat brain using Nurr1 overexpression", Stem Cells (May 2007), 25(5):1252-1262.

Vierbuchen; et al. "Direct conversion of fibroblasts to functional neurons by defined factors", Nature (Feb. 2010), 463(7284):1035-1041.

Vutskits; et al. "PSA-NCAM modulates BDNF-dependent survival and differentiation of cortical neurons", Eur J Neurosci (Apr. 2001), 13(7):1391-1402; Abstract only.

Werning; et al. "Neurons derived from reprogrammed fibroblasts functionally integrate into the fetal brain and improve symptoms of rats with Parkinson's disease", Proc Natl Acad Sci USA (Apr. 2008), 105(15):5856-5861.

Wu; et al. "Integrative genomic and functional analyses reveal neuronal subtype differentiation bias in human embryonic stem cell lines", Proc Natl Acad Sci USA (Aug. 2007), 104(34):13821-13826.

Xie; et al. "Stepwise reprogramming of B cells into macrophages", Cell (May 2004), 117(5):663-676.

Zhang; et al."In vitro differentiation of transplantable neural precursors from human embryonic stem cells", Nat Biotechnol (Dec. 2001), 19(12):1129-1133.

Zhou; et al. "Extreme Makeover: Converting One Cell into Another", Cell Stem Cell (Oct. 2008), 3(4):382-388.

Zhou; et al. "In vivo reprogramming of adult pancreatic exocrine cells to beta-cells", Nature (Oct. 2008), 455 (7213):627-632.

\* cited by examiner a

| Protein stained | TauEGFP MEFs | Balb/c MEFs | TauEGFP TTFs |
|---|---|---|---|
| Tuj1 | <0.1%* | <0.1%* | <0.1* |
| Sox2 | Absent | Absent | Absent |
| Brn2 | Absent | Absent | Absent |
| GFAP | Absent | Absent | Absent |
| P75 | Absent | Absent | Absent |
| Cytokeratins | <0.1% | n.d. | n.d. |
| Pax3 | <0.1% | n.d. | <0.1% |
| Pax6 | Absent | n.d. | Absent |
| Pax7 | Absent | n.d. | Absent |
| Nkx2.2 | Absent | n.d. | Absent |
| Olig1 | Absent | n.d. | Absent |

*Cells with a fibroblast-like morphology b

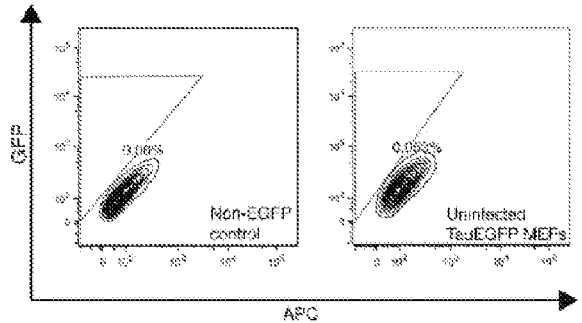

c

| | TauEGFP MEFs | | | TauEGFP perinatal TTF | | |
|---|---|---|---|---|---|---|
| | Neural media | Neural media+EGF +FGF2 | Neural media (GF withdrawal) | Neural media | Neural media+EGF +FGF2 | Neural media (GF withdrawal) |
| Sox2 | Absent | Absent | Absent | Absent | Absent | Absent |
| Brn2 | Absent | Absent | Absent | Absent | Absent | Absent |
| GFAP | Absent | <0.1% | Absent | Absent | Absent | Absent |
| MAP2 | Absent | Absent | Absent | Absent | Absent | Absent |
| Tuj1 | <1%* | <1%* | <1%* | <1%* | <1%* | <1%* |
| TauEGFP | Absent | Absent | Absent | Absent | Absent | Absent |

*Cells with a fibroblast-like morphology d.

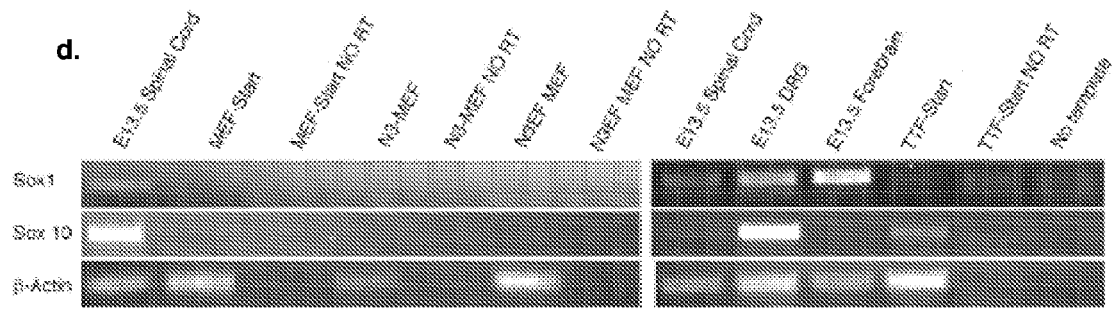

Figure 6 a  Spontaneous synaptic activity
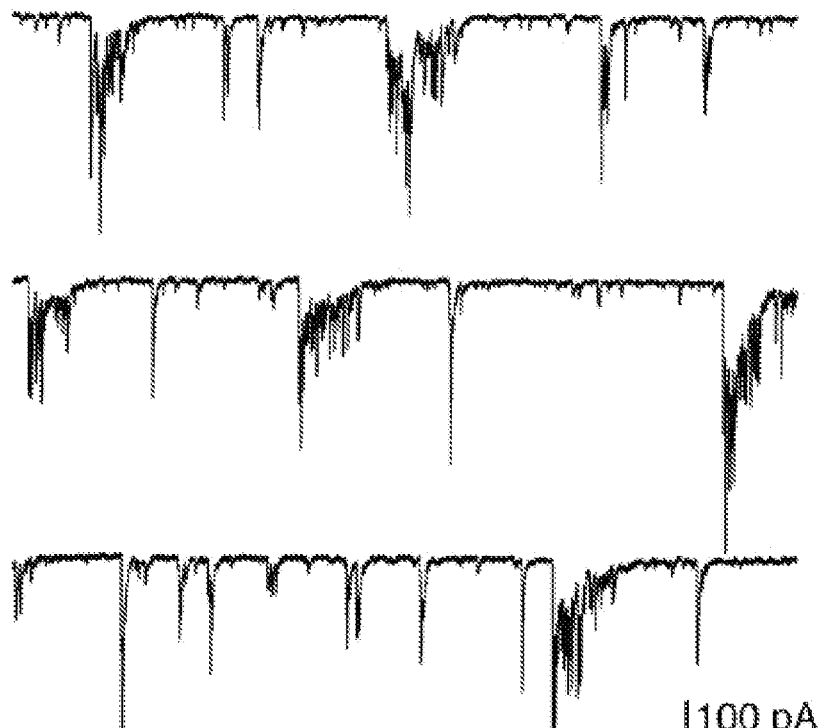
b  Evoked synaptic activity
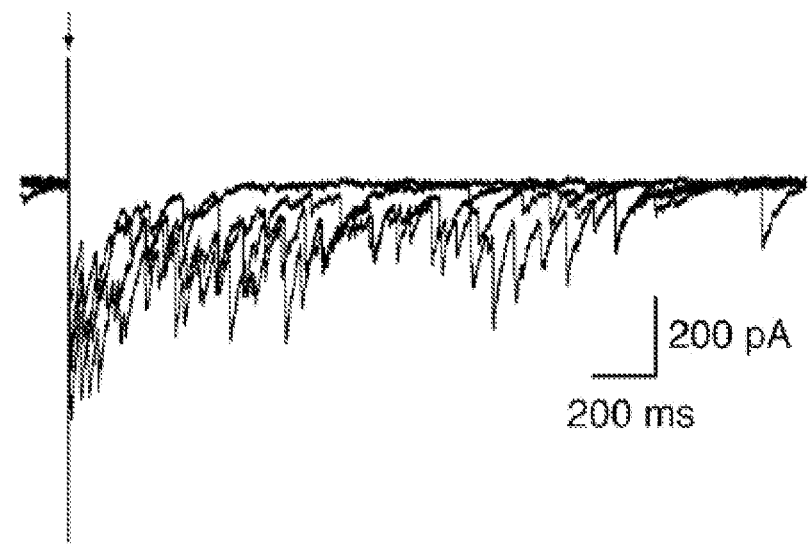
Figure 9

DIRECT CONVERSION OF CELLS TO CELLS OF OTHER LINEAGES

GOVERNMENT RIGHTS

This invention was made with support under 1018438-142-PABCA awarded by the National Institutes of Health and 5T32NS007280 awarded by the National Institutes of Health/National Institute of Neurological Disorders and Stroke. The Government has certain rights in the invention.

BACKGROUND OF THE INVENTION

The diverse cell types present in the adult organism are produced during development by lineage-specific transcription factors that define and reinforce cell type specific gene expression patterns. Cellular phenotypes are further stabilized by epigenetic modifications that allow faithful transmission of cell-type specific gene expression patterns over the lifetime of an organism (Jenuwein, T. & Allis, C. D. (2001) Science 293, 1074-80; Bernstein, B. E., et al. (2007) Cell 128, 669-81). Recent work by Yamanaka and colleagues showing that four transcription factors are sufficient to induce pluripotency in primary fibroblasts demonstrated that fully differentiated cells can be induced to undergo dramatic cell fate changes (Takahashi, K. & Yamanaka, S. (206) Cell 126, 663-76). Similarly, the transfer of somatic cell nuclei into oocytes, as well as cell fusion of pluripotent cells with differentiated cells have proven to be capable of inducing pluripotency (Briggs, R. & King, T. J. (1952) Proc Natl Acad Sci USA 38, 455-63; Gurdon, J. B., et al. (1958) Nature 182, 64-5; Campbell, K. H., et al. (1996) Nature 380, 64-6; Tada, M., et al. (2001) Curr Biol 11, 1553-8; Do, J. T. & Scholer, H. R. (2004) Stem Cells 22, 941-9; Cowan, C. A., et al. (2005) Science 309, 1369-73). This transformation has been interpreted as a reversion of mature into more primitive developmental states, with a concomitant erasure of developmentally relevant epigenetic information (Silva, J. & Smith, A. (2008) Cell 132, 532-6). The resultant cells may then be reprogrammed to a new cell fate.

Reprogramming into an embryonic state with subsequent differentiation of the embryonic-state cells into cells of the Central Nervous System (CNS) is slow and inefficient, requiring significant time and manipulation in vitro. More useful would be direct reprogramming between divergent somatic lineages. It has been observed that cell fusion or forced expression of lineage-specific genes in somatic cells can induce traits of other cell types (Blau, H. M. (1989) Trends Genet. 5, 268-72; Zhou, Q. & Melton, D. A. (2008) Cell Stem Cell 3, 382-8). For example, the basic helix-loop-helix (bHLH) transcription factor MyoD can induce muscle-specific properties in fibroblasts but not hepatocytes (Davis, R. L., et al. (1987) Cell 51, 987-1000; Schafer, B. W., et al. (1990) Nature 344, 454-8); ectopic expression of IL2 and GM-CSF receptors can lead to myeloid conversion in committed lymphoid progenitor cells (Kondo, M. et al. (2000) Nature 407, 383-6); expression of CEBPα in B-cells or Pu.1 and CEBPα in fibroblasts induces characteristics of macrophages (Bussmann, L. H. et al. (2009) Cell Stem Cell 5, 554-66; Feng, R. et al. (2008) Proc Natl Acad Sci USA 105, 6057-62; Xie, H., et al. (2004) Cell 117, 663-76) deletion of Pax5 can induce B-cells to de-differentiate toward a common lymphoid progenitor (Cobaleda, C., et al. (2007) Nature 449, 473-7); and the (bHLH) transcription factor neurogenin3, in combination with Pdx1 and MafA, can efficiently convert pancreatic exocrine cells into functional β-cells in vivo (Zhou, Q., et al. (2008) Nature 455, 627-32).

Publications relevant to conversion of pluripotent cells to neurons include, inter alia, Wu, H. et al. Proc Natl Acad Sci USA 104, 13821-13826 (2007); Johnson et al. J Neurosci 27, 3069-3077 (2007); Zhang et al. Nat Biotechnol 19, 1129-1133 (2001); Elkabetz, et al., Genes Dev 22, 152-165 (2008); Koch et al. Proc Natl Acad Sci USA 106, 3225-3230 (2009); Chambers et al. Nat Biotechnol 27, 275-280 (2009).

SUMMARY OF THE INVENTION

Methods, compositions and kits for producing functional neurons, astroctyes, oligodendrocytes and progenitor cells thereof are provided. These methods, compositions and kits find use in producing neurons, astrocytes, oligodendrocytes, and progenitor cells thereof for transplantation, for experimental evaluation, as a source of lineage- and cell-specific products, and the like, for example for use in treating human disorders of the CNS. Also provided are methods, compositions and kits for screening candidate agents for activity in converting cells into neuronal cells, astrocytes, oligodendrocytes, and progenitor cells thereof.

In some embodiments, methods are provided for converting pluripotent cells including, without limitation, embryonic stem cells, induced pluripotent stem cells, etc., into induced neuronal cells (iNs) by contacting the pluripotent cell with a neuronal reprogramming system (NR) comprising three or more factors selected from an Ascl agent, a Ngn agent, a Brn agent, a NeuroD agent, a Myt1 agent, an Olig agent or a Zic agent. In certain embodiments, particularly for human cells, neuron reprogramming factors are combination of an Ascl agent, a Brn agent, a NeuroD agent, and a Myt1 agent, which combinations of interest include without limitation, Ascl1, Brn2, Myt1l and NeuroD1. Cell culture systems for such methods are also provided. The cells find use in therapeutic methods, e.g. to provide cells for neuron replacement therapy; in screening methods, and the like. In some embodiments, the pluripotent cells are mammalian cells. In some embodiments, the mammalian pluripotent cells are human or mouse cells. In some embodiments, the cell population is combined with a reagent that specifically recognizes a marker associated with cells of the neuronal lineage, and cells that express the marker are selected for to provide an enriched population of iN cells. An advantage of the methods of the invention is the rapidity with which neuronal cells with functional properties can be generated, for example as early as 6, 7, 8, 9, 10 days after contacting the cells with the reprogramming system.

In other embodiments, methods are provided for directly converting somatic cells of one lineage into somatic cells of a different cell lineage. In some embodiments, the methods are for directly converting somatic cells into induced neuronal cells (iNs). In some embodiments, a population of non-neuronal somatic cells is contacted with a neuron reprogramming (NR) system comprising one or more neuron reprogramming (NR) factors so as to produce a population of iN cells. In some embodiments, the NR factors are selected from an Ascl agent, a Ngn agent, a Brn agent, a Myt1 agent, an Olig agent or a Zic agent. In some embodiments, the somatic cells are mammalian cells. In some embodiments, the mammalian somatic cells are human or mouse cells. In some embodiments, the efficiency of reprogramming the somatic cells to become induced neurons is at least about 0.1%. In some embodiments, the NR system-contacted population is combined with a reagent that specifically recognizes a marker associated with cells of the neuronal lineage, and cells that express the marker are selected for to provide an enriched population of iN cells. In some embodiments, selection of the cells is effected by flow cytometry (FACS). In some embodiments, selection of the cells is effected by magnetic activated cell sorting (MACS). In some embodiments, the marker associated with neural progenitors is Poly-Sialated Neural Cell Adhesion Molecule (PSA-NCAM). In some embodiments, the reagent that specifically recognizes PSA-NCAM is an anti-PSA-NCAM antibody.

In some aspects of the invention, a cell culture system is provided for directly converting somatic cells into somatic cells of a different lineage. In some embodiments, the cell culture system is for directly converting somatic cell into induced neuronal cells (iNs). In some such embodiments, the cell culture system comprises non-neuronal somatic cells and a neuron reprogramming (NR) system. In some embodiments, the NR system comprises one or more neuron reprogramming (NR) factors selected from an Ascl agent, a Ngn agent, a Brn agent, a Myt agent, an Olig agent or a Zic agent. In some embodiments, the somatic cells are mammalian cells. In some embodiments, the mammalian somatic cells are human or mouse cells.

In some aspects of the invention, methods are provided for screening candidate agents for activity modulating the direct conversion of somatic cells into somatic cells of a different cell lineage. In some embodiments, the methods are for screening candidate agents for activity modulating the direct conversion of somatic cells into induced neuronal cells (iNs). In some such embodiments, a cell culture system comprising non-neuronal somatic cells and a neuron reprogramming (NR) system, or an incomplete NR system (e.g. lacking one or more factors, comprising sub-optimal levels of one or more factors, and the like) is contacted with a candidate agent. The characteristics of the candidate-agent contacted cell culture system are compared with those of a cell culture system that has not been contacted with the candidate agent, where differences in the characteristics between the cell culture system that was contacted with candidate agent and the cell culture system that was not contacted with candidate agent indicate that the candidate agent modulates somatic cell conversion into iNs.

In some aspects of the invention, methods are provided for treating a subject in need of cell transplantation therapy in the CNS. In some embodiments, the cell transplantation therapy is neuron transplantation therapy. In some such embodiments, the subject is contacted with a composition of induced neuronal cells (iNs) prepared by converting somatic cells into induced neuronal cells using the methods and compositions of the invention. In certain embodiments, the somatic cells are derived from the subject. In some embodiments, the subject is contacted with NR factors. In some embodiments, the subject has a CNS condition. In some embodiments, the CNS condition is a neurodegenerative disease, a neuropsychiatric disorder, a channelopathy, a lysosomal storage disorder, an autoimmune disease of the CNS, a cerebral infarction, a stroke, or a spinal cord injury.

In some aspects of the invention, a neuronal cell induced by the direct conversion of a non-neuronal somatic cell is provided, where the reprogramming is performed directly on a somatic cell, in the absence of pluripotent cells, such as eggs, embryos, embryonic stem (ES) cells, induced pluripotent stem (iPS) cells, or embryonic germ cells.

BRIEF DESCRIPTION OF THE DRAWINGS

The invention is best understood from the following detailed description when read in conjunction with the accompanying drawings. The patent or application file contains at least one drawing executed in color. Copies of this patent or patent application publication with color drawing(s) will be provided by the Office upon request and payment of the necessary fee. It is emphasized that, according to common practice, the various features of the drawings are not to-scale. On the contrary, the dimensions of the various features are arbitrarily expanded or reduced for clarity. Included in the drawings are the following figures.

FIG. 6. Characterization of MEF and tail-tip fibroblast cultures. a, Passage 3 TauEGFP MEF, Balb/c MEF, and TauE-GFP TTF cultures were immunostained with antibodies against the listed antigens. Each antibody was independently validated using an appropriate positive control. The listed of antigens includes multiple markers for neural stem cells (Sox2, Brn2, GFAP), peripheral and spinal neural progenitor cells (p75, Pax3, Pax6, Pax7, Nkx2-2, Olig1) and markers for neurons and astroglia (Tuj1, TauEGFP, GFAP, Olig1). Listed percentages are out of >4500 cells. Absent means no positive cells were detected in the stained field. n.d. means fibroblast cultures were not stained. b, FACs analysis of uninfected P3 TauEGFP MEFs and control BALB/c MEFs for GFP fluorescence. Graph plots GFP fluorescence (y-axis) against APC (x-axis). c, Characterization of passage 3 TauEGFP MEFs and perinatal TTFs after culturing in neural media. Cells were either cultured in N3 media for 12 days (to promote the differentiation of potentially contaminating neural progenitor cells), N3 media with EGF and FGF2 for 12 days (a condition promoting neural progenitor cell expansion), or N3 with EGF and FGF2 for 8 days followed by growth factor withdrawal for 5 days (to first expand and then differentiate any potentially existing neural progenitor cells). Under no conditions could we detect the presence of neural cell types, only in one condition rare cells were labeled above background with a polyclonal antibody against GFAP. At least 10,000 cells were screened for each staining. d, Reverse transcription-PCR on cDNA isolated from passage 3 TauEGFP MEF and Rosa-rtTA TTF cultures. Sox1 and Sox10 could not be detected in MEFs grown in MEF media (MEF-Start), MEFs grown in N3 media (N3-MEF) for 8 days, or in MEFs grown in N3 with EGF and FGF2 for 8 days (N3EF-MEF). TTFs appear to express Sox10 at a low level. Positive controls included E13.5 spinal cord, E13.5 dorsal root ganglia (DRG), and E13.5 forebrain cDNAs. For each experimental sample a control reaction was carried without reverse transcriptase (No RT).

FIG. 9. Synaptic integration of TTF-derived 5F-iN cells in cortical neural networks. 5F perinatal TTF-iN cells were FACS-sorted for EGFP expression 7-8 days post infection and plated on cortical neuronal cultures (7 days in vitro). Electrophysiological recordings from the TauEGFP cells were performed 7 days after sorting. a, Representative consecutive traces of spontaneous synaptic network activities recorded from a TTF-iN cell. b, Representative evoked synaptic activity following stimulation (indicated by arrow). Four superimposed responses are shown.

DETAILED DESCRIPTION OF THE INVENTION

Figure 1:
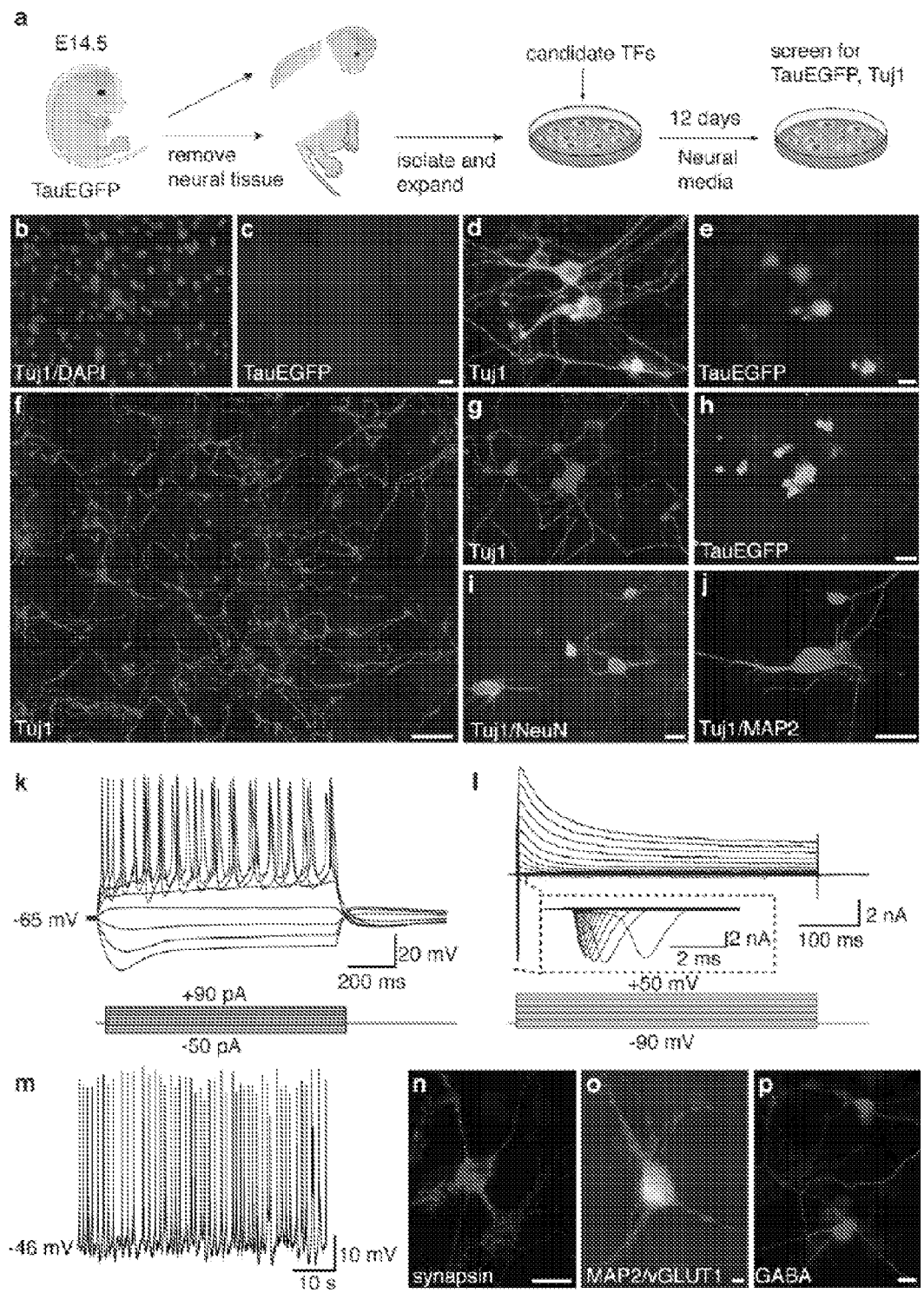
FIG. 1. A screen for neuronal fate-inducing factors and characterization of MEF-derived iN cells. a, Experimental rationale. b, Uninfected, p3 TauEGFP MEFs contained rare Tuj1-positive cells (red) with flat morphology. Blue: DAPI counterstain. c, Tuj1-positive fibroblasts in panel b do not express visible TauEGFP. d-e, MEF-iN cells express Tuj1 (red) and TauEGFP (green) and display complex neuronal morphologies 32 days after infection with the 19-factor (19F) pool. f, Tuj1 expression in MEFs 13 days after infection with the 5F pool. g-j, MEF-derived Tuj1-positive iN cells co-express the pan-neuronal markers TauEGFP (h), NeuN (red,i) and MAP2 (red,j). k, Representative traces of membrane potential responding to step depolarization by current injection (lower panel). Membrane potential was current-clamped at around −65 mV. I, Representative traces of whole-cell currents in voltage-clamp mode, cell was held at −70 mV, step depolarization from −90 mV to 60 mV at 10 mV interval were delivered (lower panel). Insert showing $Na^+$ currents. m, Spontaneous action potentials (AP) recorded from a 5F MEF-iN cell 8 days post infection. No current injection was applied. n-p, 22 days post-infection 5F MEF-iN cells express synapsin (red,n) and vesicular glutamate transporter 1 (vGLUT1) (red,o) or GABA (p). Scale bars=5 μm (o), 10 μm (e,n,p) 20 μm (c,h,i), and 200 μm (f).

Before the present methods and compositions are described, it is to be understood that this invention is not limited to particular method or composition described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supercedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a cell" includes a plurality of such cells and reference to "the peptide" includes reference to one or more peptides and equivalents thereof, e.g. polypeptides, known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DEFINITIONS

Methods, compositions and kits for producing a population of somatic cells of one cell lineage from a population of somatic cells of a different cell lineage are provided. Alternatively methods are provided for the conversion of pluripotent cells into neuronal cells. These methods, compositions and kits find use in producing neurons, astrocytes, oligodendrocytes, and progenitor cells thereof for transplantation, for experimental evaluation, as a source of lineage- and cell-specific products, and the like, for example for use in treating human disorders of the CNS. Also provided are methods, compositions and kits for screening candidate agents for activity in directly converting somatic cells into neurons, astrocytes, and oligodendrocytes. These and other objects, advantages, and features of the invention will become apparent to those persons skilled in the art upon reading the details of the subject methods and compositions as more fully described below.

The terms "induced neuronal cell," "iN cell," "induced neuron," or "iN" encompass cells of the neuronal lineage i.e. mitotic neuronal progenitor cells and post-mitotic neuronal precursor cells and mature neurons, that arise from a non-neuronal cell by experimental manipulation. Induced neuronal cells express markers specific for cells of the neuronal lineage, e.g. Tau, Tuj1, MAP2, NeuN, and the like, and may have characteristics of functional neurons, that is, they may be able to be depolarized, i.e. propagate an action potential, and they may be able to make and maintain synapses with other neurons.

The terms "induced astrocytic cell," "iA cell," "induced astrocyte," or "iA" encompass cells of the astrocyte lineage, i.e. glial progenitor cells, astrocyte precursor cells, and mature astocytes, that arise from a non-astrocytic cell by experimental manipulation. Induced astrocytes express markers specific for cells of the astrocyte lineage, e.g. GFAP, S-100, Fgfr3 and the like, and may have characteristics of functional astrocytes, that is, they may have the capacity of promoting synaptogenesis in primary neuronal cultures.

The terms "induced oligodendrocytic cell," "iO cell," "induced oligodendrocyte," or "iO" encompass cells of the oligodendrocyte lineage, i.e. glial progenitor cells, oligodendrocyte precursor cells, and mature oligodendrocytes that arise from a non-oligodendrocytic cell by experimental manipulation. Induced oligodendrocytes express markers specific for cells of the oligodendrocyte lineage, e.g. Olig1/2, 04, MBP, NG2 and the like, and may have characteristics of functional oligodendrocytes, that is, they may be able to myelinate neuronal axons in vivo and in vitro.

The terms "induced neural stem cell" or "iNSC" encompass neural stem cells that arise from a non-neuronal cell by experimental manipulation. Neural stem cells are self-renewing multipotent progenitor cells of the CNS. By self-renewing, it is meant that when they undergo mitosis, they produce at least one daughter cell that is a neural stem cell. By multipotent it is meant that it is capable of giving rise to progenitor cell (neuronal progenitors and glial progenitors) that give rise to all cell types of the central nervous system (CNS), i.e. neurons, astrocytes, and oligodendrocytes. They are not pluripotent, that is, they are not capable of giving rise to cells of other organs. Induced neural stem cells express the markers Nestin, GFAP, Pax6, Brn2, and musashi. In addition, they are mitotic so can incorporate BrdU into their DNA. They often grow as clumps or spheres (neurospheres) in culture.

The term "somatic cell" encompasses any cell in an organism that cannot give rise to all types of cells in an organism, i.e. it is not pluripotent. In other words, somatic cells are cells that have differentiated sufficiently that they will not naturally generate cells of all three germ layers of the body, i.e. ectoderm, mesoderm and endoderm.

The term "pluripotent" or "pluripotency" refers to cells with the ability to give rise to progeny that can undergo differentiation, under appropriate conditions, into cell types that collectively exhibit characteristics associated with cell lineages from the three germ layers (endoderm, mesoderm, and ectoderm). A "stem cell" is a cell characterized by the ability of self-renewal through mitotic cell division and the potential to differentiate into a tissue or an organ. Among mammalian stem cells, embryonic and somatic stem cells may be distinguished. Pluripotent stem cells, which include embryonic stem cells, embryonic germ cells and induced pluripotent cells, can contribute to tissues of a prenatal, postnatal or adult organism.

The terms "primary cells", "primary cell lines", and "primary cultures" are used interchangeably herein to refer to cells and cell cultures that have been derived from a subject and allowed to grow in vitro for a limited number of passages, i.e. splittings, of the culture. For example primary cultures are cultures that may have been passaged 0 times, 1 time, 2 times, 4 times, 5 times, 10 times, or 15 times, but not enough times go through the crisis stage. Typically, the primary cell lines of the present invention are maintained for fewer than 10 passages in vitro.

The terms "neuron reprogramming factors" or "NR factors" refer to one or more, i.e. a cocktail, of biologically active factors that act on a non-neuronal cell to promote the reprogramming, i.e. direct conversion, of the targeted cell into a neuron.

The terms "astrocyte reprogramming factors" or "AR factors" refer to one or more, i.e. a cocktail, of biologically active factors that act on a non-astrocytic cell to promote the reprogramming, i.e. direct conversion, of a non-astrocytic cell into an astrocyte.

The terms "oligodendrocyte reprogramming factors" or "OR factors" refer to one or more, i.e. a cocktail, of biologically active factors that act on a non-oligodendrocytic cell to promote the reprogramming, i.e. direct conversion, of a non-oligodendrocytic cell into an oligodendrocyte.

The terms neural stem cell (NSC) reprogramming factors" or "NSCR factors" refer to one or more, i.e. a cocktail, of biologically active factors that act to promote the reprogramming, i.e. direct conversion, of non-neuronal cell into a neural stem cell.

The term "neuron reprogramming system" or "NR system" refers to reagents and culture conditions that promote the reprogramming, i.e. direct conversion, of non-neuronal cells to induced neuronal cells (iNs), where the non-neuronal cells may be somatic cells or may be pluripotent cells. An NR system comprises one or more, i.e. a cocktail, of somatic cell-to-neuron reprogramming factors. An NR may also optionally comprise other reagents, such as agents that promote cell reprogramming, agents that promote the survival and differentiation of neurons, agents that promote the differentiation of subtypes of neurons, and the like, as known in the art. An NR system does not induce a non-neuronal somatic cell to become pluripotent, e.g. an induced pluripotent stem cell (iPS), in the course of conversion into induced neuronal cells. In other words, an NR system induces the direct conversion of somatic cells of one lineage into induced neuronal cells (iNs), or induces pluripotent cells to become neuronal cells. Thus, for example, the NR system does not require iPS reprogramming factors as they are known in the art, e.g. Oct3/4, SOX2, KLF4, MYC, Nanog, or Lin28; or culture conditions developed in the art for culturing pluripotent stem cells, e.g. culture in hanging droplets.

The term "astrocyte reprogramming system" or "AR system" refers to reagents and culture conditions that promote the reprogramming, i.e. direct conversion, of non-astrocytic cells into induced astrocytes (iAs). An AR system comprises one or more, i.e. a cocktail, of cell-to-astrocyte reprogramming factors. An AR may also optionally comprise other reagents, such as agents that promote cell reprogramming, agents that promote the survival and differentiation of astrocytes, agents that promote the differentiation of subtypes of astrocytes, and the like, as known in the art. An AR system does not induce the non-astrocytic cell to become pluripotent, e.g. an induced pluripotent stem cell (iPS), in the course of conversion into an induced astrocyte. In other words, an AR system induces the direct conversion of cells of a non-astrocyte lineage into induced astrocytes.

The term "oligodendrocyte reprogramming system" or "OR system" refers to reagents and culture conditions that promote the reprogramming, i.e. direct conversion, of non-oligodendrocytic cells to induced oligodendrocytes (iOs). An OR system comprises one or more, i.e. a cocktail, of oligodendrocyte reprogramming factors. An OR may also optionally comprise other reagents, such as agents that promote cell reprogramming, agents that promote the survival and differentiation of oligodendrocytes, agents that promote the differentiation of subtypes of oligodendrocytes, and the like, as known in the art. An OR system does not induce the non-oligodendrocytic cell to become pluripotent, e.g. an induced pluripotent stem cell (iPS), in the course of conversion into an induced oligodendrocyte. In other words, an OR system induces the direct conversion of cells of a non-oligodendrocyte lineage into induced oligodendrocytes.

The term "neural stem cell (NSC) reprogramming system" or "NSCR system" refers to reagents and culture conditions that promote the reprogramming, i.e. direct conversion, of post-mitotic somatic cells to induced neural stem cells (iNSCs). An NSCR system comprises one or more, i.e. a cocktail, of cell-to-NSC reprogramming factors. An NSCR may also optionally comprise other reagents, such as agents that promote cell reprogramming, agents that promote the survival and proliferation of neural stem cells, and the like, as known in the art. An NSCR system does not induce the cell to become pluripotent, e.g. an induced pluripotent stem cell (iPS), in the course of conversion into an induced neural stem cell. In other words, an NSCR system induces the direct conversion of cells into induced neural stem cells.

The terms "efficiency of reprogramming", "reprogramming efficiency", "efficiency of conversion", or "conversion efficiency" are used interchangeably herein to refer to the ability of a culture of cells of one cell lineage to give rise to an induced cell of another cell lineage when contacted with the reprogramming system, for example, the ability of a culture of somatic cells to give rise to induced neurons (iNs) when contacted with a cell-to-neuron reprogramming (NR) system. By "enhanced efficiency of reprogramming" or "enhanced efficiency of conversion" it is meant an enhanced ability of a culture of somatic cells to give rise to the induced cell when contacted with the reprogramming system relative to a culture of somatic cells that is not contacted with the reprogramming system, for example, an enhanced ability of a culture of cells to give rise to iN cells when contacted with an NR system relative to a culture of cells that is not contacted with the same NR system. By enhanced, it is meant that the primary cells or primary cell cultures have an ability to give rise to the induced cells (e.g. iN cells) that is greater than the ability of a population that is not contacted with the reprogramming system (e.g. a NR system), i.e. 150%, 200%, 300%, 400%, 600%, 800%, 1000%, or 2000% of the ability of the uncontacted population. In other words, the primary cells or primary cell cultures produce about 1.5-fold, about 2-fold, about 3-fold, about 4-fold, about 6-fold, about 8-fold, about 10-fold, about 20-fold, about 30-fold, about 50-fold, about 100-fold, about 200-fold the number of induced cells (e.g. iN cells) as the uncontacted population, or more.

The terms "treatment", "treating", "treat" and the like are used herein to generally refer to obtaining a desired pharmacologic and/or physiologic effect. The effect may be prophylactic in terms of completely or partially preventing a disease or symptom thereof and/or may be therapeutic in terms of a partial or complete stabilization or cure for a disease and/or adverse effect attributable to the disease. "Treatment" as used herein covers any treatment of a disease in a mammal, particularly a human, and includes: (a) preventing the disease or symptom from occurring in a subject which may be predisposed to the disease or symptom but has not yet been diagnosed as having it; (b) inhibiting the disease symptom, i.e., arresting its development; or (c) relieving the disease symptom, i.e., causing regression of the disease or symptom.

The terms "individual," "subject," "host," and "patient," are used interchangeably herein and refer to any mammalian subject for whom diagnosis, treatment, or therapy is desired, particularly humans.

The subject invention is directed to methods of reprogramming, i.e. converting a somatic cell of one lineage into a somatic cell of a different lineage by contacting the starting somatic cell with a reprogramming system comprising one or more somatic cell reprogramming factors; or of programming a pluripotent cell to rapidly convert to a neuronal cell. Examples of neuronal cells that may be generated by the methods of the invention include neurons, astrocytes, oligodendrocytes, and progenitor cells thereof. In some embodiments the following description focuses on reprogramming, i.e. converting, non-neuronal somatic cells into neurons by contacting them with a somatic cell-to-neuron reprogramming system (NR system) comprising one or more somatic cell-to-neuron reprogramming factors (NR factors). However, with the exception of the reprogramming factors and the reprogramming systems used in the method, the subject methods and the reagents, devices and kits thereof also find use in converting non-astrocytic somatic cells into astrocytes, non-oligodendrocytic somatic cells into oligodendrocytes, and post-mitotic somatic cells of any lineage into neural stem cells as well.

Neuron Reprogramming (NR) Factors and Systems

Neuron reprogramming (NR) factors are biologically active factors that act on a cell to alter transcription so as to convert the cell into a neuron, i.e. an induced neuron (iN). NR factors are provided to somatic or pluripotent cells in the context of a NR system. Examples of NR factors include an Ascl agent, a Ngn agent, a NeuroD agent, a Brn agent, a Myt agent, an Olig agent and a Zic agent In certain embodiments, particularly for human cells, neuron reprogramming factors are combination of an Ascl agent, a Brn agent, a NeuroD agent, and a Myt1 agent, which combinations of interest include without limitation, Ascl1, Brn2, Myt1I and NeuroD1.

The term Ascl agent is used to refer to Ascl (achaete-scute-like) polypeptides and the nucleic acids that encode them. Ascl polypeptides are basic helix-loop-helix transcription factors of the achaete-scute family, which activate transcription by binding to the E box (5'-CANNTG-3'). The terms "Ascl gene product", "Ascl polypeptide", and "Ascl protein" are used interchangeably herein to refer to native sequence Ascl polypeptides, Ascl polypeptide variants, Ascl polypeptide fragments and chimeric Ascl polypeptides that can modulate transcription. Native sequence Ascl polypeptides include the proteins Ascl1 (achaete-scute complex homolog 1 (*Drosophila*); ASH1; HASH1; MASH1; bHLHa46; GenBank Accession Nos. NM_004316.3 and NP_004307.2); Ascl2 (achaete-scute complex homolog 2 (*Drosophila*); ASH2; HASH2; MASH2; bHLHa45; GenBank Accession Nos. NM_005170.2 and NP_005161.1); Ascl3 (achaete-scute complex homolog 3 (*Drosophila*); SGN1; HASH3; bHLHa42; GenBank Accession Nos. NM_020646.1 and NP_065697.1); Ascl4 (achaete-scute complex homolog 4 (*Drosophila*); HASH4; bHLHa44; GenBank Accession Nos. NM_203436.2 and NP_982260.2; and Ascl5 (achaete-scute complex homolog 5 (*Drosophila*); bHLHa47; GenBank Accession Nos. XM_001719321.2 and XP_001719373.2). Ascl polypeptides, e.g. those that are at least 50%, 55%, 60%, 65%, 70%, 75%, 80%, 85%, 90%, 91%, 92%, 95%, 97%, 99%, or are 100% identical to the sequence provided in the GenBank Accession Nos. above find use as reprogramming factors in the present invention, as do nucleic acids encoding these polypeptides or their transcriptionally active domains and vectors comprising these nucleic acids. In certain embodiments, the Ascl agent is an Ascl1 agent.

Ngn (neurogenin) polypeptides are basic helix-loop-helix transcription factors of the neurogenin family of proteins. The terms "Ngn gene product", "Ngn polypeptide", and "Ngn protein" are used interchangeably herein to refer to native sequence Ngn polypeptides, Ngn polypeptide variants, Ngn polypeptide fragments and chimeric Ngn polypeptides that can modulate transcription. Native sequence Ngn polypeptides include the proteins Ngn1 (NeuroG1; AKA; Math4C; bHLHa6; NeuroD3; GenBank Accession Nos. NM_006161.2 and NP_006152.2); Ngn2 (NeuroG2; Atoh4; Math4A; bHLHa8; MGC46562; GenBank Accession Nos. NM_024019.2 and NP_076924.1); and Ngn3 (NeuroG3; Atoh5; Math4B; bHLHa7; GenBank Accession Nos. NM_020999.2 and NP_066279.2). Ngn polypeptides, e.g. those that are at least 50%, 55%, 60%, 65%, 70%, 75%, 80%, 85%, 90%, 91%, 92%, 95%, 97%, 99%, or are 100% identical to the sequence provided in the GenBank Accession Nos. above find use as reprogramming factors in the present invention, as do nucleic acids encoding these polypeptides or their transcriptionally active domains and vectors comprising these nucleic acids. In certain embodiments, the Ngn agent is an Ngn1 agent or an Ngn2 agent.

NeuroD (neurogenic differentiation) polypeptides are basic helix-loop-helix transcription factors of the neurogenic differentiation family of proteins. The terms "NeuroD gene product", "NeuroD polypeptide", and "NeuroD protein" are used interchangeably herein to refer to native sequence NeuroD polypeptides, NeuroD polypeptide variants, NeuroD polypeptide fragments and chimeric NeuroD polypeptides that can modulate transcription. Native sequence NeuroD polypeptides include the proteins NeuroD1 (GenBank Accession Nos. NM_002500.2 and NP_002491.2); NeuroD2 (GenBank Accession Nos. NM_006160.3 and NP_006151.3); and NeuroD4 (GenBank Accession Nos. NM_021191.2 and NP_067014.2). NeuroD polypeptides, e.g. those that are at least 50%, 55%, 60%, 65%, 70%, 75%, 80%, 85%, 90%, 91%, 92%, 95%, 97%, 99%, or are 100% identical to the sequence provided in the GenBank Accession Nos. above find use as reprogramming factors in the present invention, as do nucleic acids encoding these polypeptides or their transcriptionally active domains and vectors comprising these nucleic acids. In certain embodiments, the NeuroD agent is a NeuroD1 agent.

Brn (Brain-specific homeobox) polypeptides are members of the POU-domain containing family of transcription factors, which bind with high affinity to octameric DNA sequences. The terms "Brn gene product", "Brn polypeptide", and "Brn protein" are used interchangeably herein to refer to native sequence Brn polypeptides, Brn polypeptide variants, Brn polypeptide fragments and chimeric Brn polypeptides. Native sequence Brn polypeptides include the proteins Brn1 (POU class 3 homeobox 3; POU3F3; and OTF8; GenBank Accession Nos. NM_006236.1 and NP_006227.1); Brn2 (POU class 3 homeobox 2; POU3F2; POU3F; OCT7; OTF7; GenBank Accession Nos. NM_005604.2 and NP_005595.2); Brn3A (POU class 4 homeobox 1; POU4F1; RDC-1; Oct-T1; FLJ13449; GenBank Accession Nos. NM_006237.3 and NP_006228.3); Brn3B (POU class 4 homeobox 2; POU4F2; BRN3.2; GenBank Accession Nos. NM_004575.2 and NP_004566.2); Brn3C (POU class 4 homeobox 3; POU4F3; DFNA15; MGC138412; GenBank Accession Nos. NM_002700.2 and NP_002691.1); Brn4 (POU class 3 homeobox 4; POU3F4; DFN3; OTF9; DFNX2; GenBank Accession Nos. NM_000307.3 and NP_000298.2); and Brn5 (POU class 6 homeobox 1; POU6F1MPOU; TCFB1; GenBank Accession Nos. NM_002702.3 and NP_002693.3). Brn polypeptides, e.g. those that are at least 50%, 55%, 60%, 65%, 70%, 75%, 80%, 85%, 90%, 91%, 92%, 95%, 97%, 99%, or are 100% identical to the sequence provided in the GenBank Accession Nos. above find use as reprogramming factors in the present invention, as do nucleic acids encoding these polypeptides or their transcriptionally active domains and vectors comprising these nucleic acids. In certain embodiments, the Brn agent is a Brn2 agent or a Brn4 agent.

Myt (myelin transcription factor) polypeptides are members of the Myt family of zinc-finger transcription factors. The terms "Myt gene product", "Myt polypeptide", and "Myt protein" are used interchangeably herein to refer to native sequence Myt1 polypeptides, Myt polypeptide variants, Myt polypeptide fragments and chimeric Myt polypeptides that can modulate transcription. Native sequence Myt1 polypeptides include the proteins Myt1 (Nzf2; Nztf2; and mKIAA0835; GenBank Accession Nos. NM_008665.3 and NP_032691.2); and Myt1l (myelin transcription factor 1-like; NZF1; Neural zinc finger transcription factor 1; GenBank Accession Nos. NM_015025.2 and NP_055840.2). Myt polypeptides, e.g. those that are at least 50%, 55%, 60%, 65%, 70%, 75%, 80%, 85%, 90%, 91%, 92%, 95%, 97%, 99%, or are 100% identical to the sequence provided in the GenBank Accession Nos. above find use as reprogramming factors in the present invention, as do nucleic acids encoding these polypeptides or their transcriptionally active domains and vectors comprising these nucleic acids. In certain embodiments, the Myt agent is a Myt1I agent.

Olig (oligodendrocyte lineage transcription factor) polypeptides are members of the basic helix-loop-helix family of transcription factors. The terms "Olig gene product", "Olig polypeptide", and "Olig protein" are used interchangeably herein to refer to native sequence Olig polypeptides, Olig polypeptide variants, Olig polypeptide fragments and chimeric Olig polypeptides that can modulate transcription. Native sequence Olig polypeptides include the proteins Olig1 (BHLHB6 and BHLHE21; GenBank Accession Nos. NM_138983.2 and NP_620450.2); Olig2 (BHLHB1; OLIGO2; RACK17; PRKCBP; bHLHe19; GenBank Accession Nos. NM_005806.2 and NP_005797.1); and Olig3 (Bhlhb7; bHLHe20; GenBank Accession Nos. NM_175747.2 and NP_786923.1). Olig polypeptides, e.g. those that are at least 50%, 55%, 60%, 65%, 70%, 75%, 80%, 85%, 90%, 91%, 92%, 95%, 97%, 99%, or are 100% identical to the sequence provided in the GenBank Accession Nos. above find use as reprogramming factors in the present invention, as do nucleic acids encoding these polypeptides or their transcriptionally active domains and vectors comprising these nucleic acids. In certain embodiments, the Olig agent is an Olig2 agent.

Zic polypeptides are members of the C2H2-type zinc finger family of transcription factors. The terms "Zic gene product", "Zic polypeptide", and "Zic protein" are used interchangeably herein to refer to native sequence Zic polypeptides, Zic polypeptide variants, Zic polypeptide fragments and chimeric Zic polypeptides that can modulate transcription. Native sequence Zic polypeptides include the proteins Zic1 (ZIC, ZNF201; GenBank Accession Nos. NM_003412.3 and NP_003403.2); Zic2 (HEP5; GenBank Accession Nos. NM_007129.2 and NP_009060.2); Zic3 (HTX; HTX1; ZNF203; GenBank Accession Nos. NM_003413.3 and NP_003404.1); Zic4 (FLJ42609; FLJ45833; GenBank Accession Nos. NM_001168378.1 (isoform 1), NM_001168379.1 (isoform 2), and NM_032153.4 (isoform 3)); and Zic5 (GenBank Accession Nos. NM_033132.3 and NP_149123.2). Zic polypeptides, e.g. those that are at least 50%, 55%, 60%, 65%, 70%, 75%, 80%, 85%, 90%, 91%, 92%, 95%, 97%, 99%, or are 100% identical to the sequence provided in the GenBank Accession Nos. above find use as reprogramming factors in the present invention, as do nucleic acids encoding these polypeptides or their transcriptionally active domains and vectors comprising these nucleic acids. In certain embodiments, the Zic agent is a Zic1 agent.

In some embodiments, the one or more NR factors are provided as nuclear acting polypeptides. In other words, the subject cells are contacted with NR polypeptides that act in the nucleus.

To promote transport of NR polypeptides across the cell membrane, NR polypeptide sequences may be fused to a polypeptide permeant domain. A number of permeant domains are known in the art and may be used in the nuclear acting polypeptides of the present invention, including peptides, peptidomimetics, and non-peptide carriers. For example, a permeant peptide may be derived from the third alpha helix of Drosophila melanogaster transcription factor Antennapaedia, referred to as penetratin, which comprises the amino acid sequence RQIKIWFQNRRMKWKK. As another example, the permeant peptide comprises the HIV-1 tat basic region amino acid sequence, which may include, for example, amino acids 49-57 of naturally-occurring tat protein. Other permeant domains include poly-arginine motifs, for example, the region of amino acids 34-56 of HIV-1 rev protein, nona-arginine, octa-arginine, and the like. (See, for example, Futaki et al. (2003) Curr Protein Pept Sci. 2003 April; 4(2): 87-96; and Wender et al. (2000) Proc. Natl. Acad. Sci. U.S.A 2000 Nov. 21; 97(24):13003-8; published U.S. Patent applications 20030220334; 20030083256; 20030032593; and 20030022831, herein specifically incorporated by reference for the teachings of translocation peptides and peptoids). The nona-arginine (R9) sequence is one of the more efficient PTDs that have been characterized (Wender et al. 2000; Uemura et al. 2002).

The NR polypeptides may be prepared by in vitro synthesis, using conventional methods as known in the art. Various commercial synthetic apparatuses are available, for example, automated synthesizers by Applied Biosystems, Inc., Beckman, etc. By using synthesizers, naturally occurring amino acids may be substituted with unnatural amino acids. The particular sequence and the manner of preparation will be determined by convenience, economics, purity required, and the like. Other methods of preparing polypeptides in a cell-free system include, for example, those methods taught in U.S. Application Ser. No. 61/271,000, which is incorporated herein by reference.

The NR polypeptides may also be isolated and purified in accordance with conventional methods of recombinant synthesis. A lysate may be prepared of the expression host and the lysate purified using HPLC, exclusion chromatography, gel electrophoresis, affinity chromatography, or other purification technique. For the most part, the compositions which are used will comprise at least 20% by weight of the desired product, more usually at least about 75% by weight, preferably at least about 95% by weight, and for therapeutic purposes, usually at least about 99.5% by weight, in relation to contaminants related to the method of preparation of the product and its purification. Usually, the percentages will be based upon total protein. NR polypeptides may be produced recombinantly not only directly, but also as a fusion polypeptide with a heterologous polypeptide, e.g. a polypeptide having a specific cleavage site at the N-terminus of the mature protein or polypeptide. Expression vectors usually contain a selection gene, also termed a selectable marker. This gene encodes a protein necessary for the survival or growth of transformed host cells grown in a selective culture medium.

Following purification by commonly known methods in the art, NR polypeptides are provided to the subject cells by standard protein transduction methods. In some cases, the protein transduction method includes contacting cells with a composition containing a carrier agent and at least one purified NR polypeptide. Examples of suitable carrier agents and methods for their use include, but are not limited to, commercially available reagents such as Chariot™ (Active Motif, Inc., Carlsbad, Calif.) described in U.S. Pat. No. 6,841,535; Bioport™ (Gene Therapy Systems, Inc., San Diego, Calif.), GenomeONE (Cosmo Bio Co., Ltd., Tokyo, Japan), and ProteoJuice™ (Novagen, Madison, Wis.), or nanoparticle protein transduction reagents as described in, e.g., U.S. patent application Ser. No. 10/138,593.

In other embodiments, the one or more NR factors are nucleic acids encoding NR polypeptides, i.e. NR nucleic acids. Vectors used for providing NR nucleic acids to the subject cells will typically comprise suitable promoters for driving the expression, that is, transcriptional activation, of the nucleic acids. This may include ubiquitously acting promoters, for example, the CMV-β-actin promoter, or inducible promoters, such as promoters that are active in particular cell populations or that respond to the presence of drugs such as tetracycline. By transcriptional activation, it is intended that transcription will be increased above basal levels in the target cell by at least about 10-fold, by at least about 100-fold, more usually by at least about 1000-fold. In addition, vectors used for providing the nucleic acids may include genes that must later be removed, e.g. using a recombinase system such as Cre/Lox, or the cells that express them destroyed, e.g. by including genes that allow selective toxicity such as herpesvirus TK, bcl-xs, etc NR nucleic acids may be provided directly to the subject cells. In other words, the cells are contacted with vectors comprising NR nucleic acids such that the vectors are taken up by the cells. Methods for contacting cells with nucleic acid vectors, such as electroporation, calcium chloride transfection, and lipofection, are well known in the art. Vectors that deliver nucleic acids in this manner are usually maintained episomally, e.g. as plasmids or minicircle DNAs.

Alternatively, the nucleic acid may be provided to the subject cells via a virus. In other words, the cells are contacted with viral particles comprising the NR nucleic acids. Retroviruses, for example, lentiviruses, are particularly suitable to such methods. Commonly used retroviral vectors are "defective", i.e. unable to produce viral proteins required for productive infection. Rather, replication of the vector requires growth in a packaging cell line. To generate viral particles comprising nucleic acids of interest, the retroviral nucleic acids comprising the nucleic acid are packaged into viral capsids by a packaging cell line. Different packaging cell lines provide a different envelope protein to be incorporated into the capsid, this envelope protein determining the specificity of the viral particle for the cells. Envelope proteins are of at least three types, ecotropic, amphotropic and xenotropic. Retroviruses packaged with ecotropic envelope protein, e.g. MMLV, are capable of infecting most murine and rat cell types, and are generated by using ecotropic packaging cell lines such as BOSC23 (Pear et al. (1993) P.N.A.S. 90:8392-8396). Retroviruses bearing amphotropic envelope protein, e.g. 4070A (Danos et al, supra.), are capable of infecting most mammalian cell types, including human, dog and mouse, and are generated by using amphotropic packaging cell lines such as PA12 (Miller et al. (1985) Mol. Cell. Biol. 5:431-437); PA317 (Miller et al. (1986) Mol. Cell. Biol. 6:2895-2902); GRIP (Danos et al. (1988) PNAS 85:6460-6464). Retroviruses packaged with xenotropic envelope protein, e.g. AKR env, are capable of infecting most mammalian cell types, except murine cells. The appropriate packaging cell line may be used to ensure that the subject cells are targeted by the packaged viral particles. Methods of introducing the retroviral vectors comprising NR nucleic acids into packaging cell lines and of collecting the viral particles that are generated by the packaging lines are well known in the art.

In some embodiments, only one NR factor is provided, e.g. an Ascl agent (A), an Ngn agent (N); a NeuroD agent (Nd), a Brn agent (B), a Myt agent (M), an Olig agent (O), or a Zic agent (Z). In some embodiments, a set of at least two agents is provided, e.g. an Ascl agent and a Brn agent; an Ascl agent and a Myt agent; an Ascl agent and Olig agent; an Ascl agent and a Zic agent; a Ngn agent and a Brn agent; a Ngn agent and a Myt agent; a Ngn agent and Olig agent; a Ngn agent and a Zic agent; a NeuroD agent and a Brn agent; a NeuroD agent and a Myt agent; a NeuroD agent and Olig agent; a NeuroD agent and a Zic agent; a Brn agent and a Myt1I agent. In some embodiments, a set of at least three agents is provided, e.g., an Ascl agent, a Brn agent, and a Myt agent (BAM); an Ascl agent, a Brn agent and a Zic agent (BAZ); an Ascl agent, a Myt agent and an Olig agent (AMO); an Ascl agent, an Olig agent and a Zic agent (AOZ); an Ascl agent, a Brn agent, and an Olig agent (ABO); an Ascl agent, a Myt agent, and a Zic agent (AMZ); a Brn agent, a Myt agent, and a Zic agent (BMZ); a Brn agent, a Myt agent, and an Olig agent (BMO); an Ngn agent, a Brn agent, and a Myt agent (NBM); a Ngn agent, a Brn agent and a Zic agent (NBZ); a Ngn agent, a Myt agent and an Olig agent (NMO); a Ngn agent, an Olig agent and a Zic agent (NOZ); a Ngn agent, a Brn agent, and an Olig agent (NBO); a Ngn agent, a Myt agent, and a Zic agent (NMZ); a NeuroD agent, a Brn agent, and a Myt agent (NdBM); a NeuroD agent, a Brn agent and a Zic agent (NdBZ); a NeuroD agent, a Myt agent and an Olig agent (NdMO); a NeuroD agent, an Olig agent and a Zic agent (NdOZ); a NeuroD agent, a Brn agent, and an Olig agent (NdBO); a NeuroD agent, a Myt agent, and a Zic agent (NdMZ). In some embodiments, a set of at least four agents is provided, e.g., an Ascl agent, a Brn agent, a Myt agent and an Olig agent (ABMO); an Ascl agent, a Brn agent, a Myt agent, and a Zic agent (ABMZ); an Ascl agent, a Brn agent, an Olig agent and a Zic agent (ABOZ); an Ascl agent, a Myt agent, an Olig agent, and a Zic agent (AMOZ); a Ngn agent, a Brn agent, a Myt and an Olig agent (NBMO); a Ngn agent, a Brn agent, a Myt agent, and a Zic agent (NBMZ); a Ngn agent, a Brn agent, an Olig agent and a Zic agent (NBOZ); a Ngn agent, a Myt agent, an Olig agent, and a Zic agent (NMOZ); a NeuroD agent, a Brn agent, a Myt and an Olig agent (NdBMO); a NeuroD agent, a Brn agent, a Myt agent, and a Zic agent (NdBMZ); a NeuroD agent, a Brn agent, an Olig agent and a Zic agent (NdBOZ); a NeuroD agent, a Myt agent, an Olig agent, and a Zic agent (NdMOZ); a Brn agent, a Myt agent, an Olig agent, and a Zic agent (BMOZ). In some embodiments, a set of at least five agents is provided, e.g. an Ascl agent, a Brn agent, a Myt agent, an Olig agent, and a Zic agent (ABMOZ); an Ngn agent, a Brn agent, a Myt agent, an Olig agent, and a Zic agent (NBMOZ); a NeuroD agent, a Brn agent, a Myt agent, an Olig agent, and a Zic agent (NdBMOZ). In some embodiments, a set of six agents is provided, e.g. an Ascl agent, an Ngn agent, a Brn agent, a Myt agent, an Olig agent, and a Zic agent (ANBMOZ). In some embodiments, a set of seven agents is provided, e.g. an Ascl agent, an Ngn agent, a NeuroD agent, a Brn agent, a Myt agent, an Olig agent, and a Zic agent (ANNdBMOZ).

When more than one NR factors is provided, the NR factors may be provided individually or as a single composition, that is, as a premixed composition, of factors. The NR factors may be added to the subject cells simultaneously or sequentially at different times. NR factors may be provided to non-neuronal somatic cells individually or as a single composition, that is, as a premixed composition, of NRs. The factors may be provided at the same molar ratio or at different molar ratios. The factors may be provided once or multiple times in the course of culturing the cells of the subject invention. For example, the agent(s) may be provided to the subject cells one or more times and the cells allowed to incubate with the agents for some amount of time following each contacting event, e.g. 16-24 hours, after which time the media is replaced with fresh media and the cells are cultured further.

In addition to the one or more NR factors, the NR system may include other reagents. For example, the NR system may include one or more agents known in the art to promote cell reprogramming. Examples of agents known in the art to promote cell reprogramming include GSK-3 inhibitors (e.g. CHIR99021 and the like (see, e.g., Li, W. et al. (2009) Stem Cells, Epub Oct. 16 2009)); histone deacetylase (HDAC) inhibitors (e.g., those described in US20090191159, the disclosure of which is incorporated herein by reference); histone methyltransferase inhibitors (e.g. G9a histone methyltransferase inhibitors, e.g. BIX-01294, and the like (see, e.g. Shi, Y et al. (2008) Cell Stem Cells 3(5):568-574)); agonists of the dihydropyridine receptor (e.g. BayK8644, and the like (see, e.g., Shi, Y et al. (2008) Cell Stem Cell 3(5):568-574)); and inhibitors of TGFβ signaling (e.g. RepSox and the like (see, e.g. Ichida, J K. et al. (2009) Cell Stem Cell 5(5):491-503)). Examples of agents known in the art to promote cell reprogramming also include agents that reduce the amount of methylated DNA in a cell, for example by suppressing DNA methylation activity in the cell or promoting DNA demethylation activity in a cell. Examples of agents that suppress DNA methylation activity include, e.g., agents that inhibit DNA methyltransferases (DNMTs), e.g. 5-aza-cytidine, 5-aza-2'-deoxycytidine, MG98, S-adenosyl-homocysteine (SAH) or an analogue thereof (e.g. periodate-oxidized adenosine or 3-deazaadenosine), DNA-based inhibitors such as those described in Bigey, P. et al (1999) J. Biol. Chem. 274:459-44606, antisense nucleotides such as those described in Ramchandani, S et al, (1997) Proc. Natl. Acad. Sci. USA 94: 684-689 and in Fournel, M et al, (1999) J. Biol. Chem. 274:24250-24256, or any other DNMT inhibitor known in the art. Examples of agents that promote DNA demethylation activity include, e.g., cytidine deaminases, e.g. AID/APOBEC agents (Bhutani, N et al. (2009) Nature. December 21. [Epub ahead of print]; Rai, K. et al. (2008) Cell 135:1201-1212), agents that promote G:T mismatch-specific repair activity, e.g. Methyl binding domain proteins (e.g. Mbp4) and thymine-DNA glycosylase (TDG) protein (Rai, K. et al. (2008) Cell 135:1201-1212), agents that promote growth arrest and DNA-damage-inducible 45 (GADD45) activity protein (Rai, K. et al. (2008) Cell 135:1201-1212), and the like.

Other reagents of interest for optional inclusion in the NR system are agents known in the art to promote the survival and differentiation of stem cells into neurons and/or mitotic neuronal progenitors or post-mitotic neuronal precursors into neurons. These include, for example, B27 (Invitrogen), glucose, transferrin, serum (e.g. fetal bovine serum, and the like), and the like. See, e.g. the Examples section presented below.

Other reagents of interest for optional inclusion in the NR system are agents that inhibit proliferation, e.g. AraC.

Other reagents of interest for optional inclusion in the NR system are agents known in the art to promote the differentiation of neuronal precursors into particular neuronal subtypes. For example, to promote differentiation into excitatory (glutamatergic) neurons, cells may also be contacted with Tlx polypeptides or nucleic acids encoding these polypeptides (e.g. Cheng, L. et al. (2004) Nat. Neurosci. 7(5):510-517). To promote differentiation into inhibitory (GABAergic) neurons, cells may also be contacted with Lbx1 polypeptides or nucleic acids encoding these polypeptides (e.g. Cheng, L. et al. (2005) Nature Neuroscience 8(11):1510-1515). To promote differentiation into dopaminergic (DA) neurons, cells may also be co-cultured with a PA6 mouse stromal cell line under serum-free conditions, see, e.g., Kawasaki et al., (2000) Neuron, 28(1):3140. To promote differentiation into cholinergic neurons, cells may also be contacted with Lhx8 polypeptides or nucleic acids encoding these polypeptides (Manabe, T. et al. (2007) Cell Death and Differentiation 14: 1080-1085). To promote differentiation of spinal cord motor neurons, cells may also be contacted with Mnx1 (Hb9) (Wichterle, H et al. (2002) Cell 110(3):385-397). To promote differentiation into corticospinal projection neurons, e.g. motor neurons, cells may also be contacted with Fezf2 or Ctip2 polypeptides or nucleic acids encoding those polypeptides (e.g. Molyneaux et al. (2005) Neuron 47(6):817-31; Chen et al. (2008) Proc Natl Acad Sci USA 105(32):11382-7). To promote differentiation of corticocortical projection neurons, e.g. callosal neurons, cells may be contacted with Satb2 polypeptides or nucleic acids encoding those polypeptides (e.g. Alcamo et al. (2008) Neuron 57(3):364-77; Britanova et al. (2008) Neuron 57(3):378-92). To promote differentiation of corticothalamic neurons, cells may be contacted with Sox5 polypeptides or nucleic acids encoding those polypeptides (e.g. Lai et al. (2008) Neuron 57(2):232-47). Other methods have also been described, see, e.g., Pomp et al., (2005), Stem Cells 23(7):923-30; U.S. Pat. No. 6,395, 546, e.g., Lee et al., (2000), Nature Biotechnol., 18:675-679.

Reagents in the NR system may be provided in any culture media known in the art to promote cell survival, e.g. DMEM, Iscoves, Neurobasal media, etc. In some cases, the media will be DMEM. In some cases, with media will be N3. Media may be supplemented with agents that inhibit the growth of bacterial or yeast, e.g. penicillin/streptomycin, a fungicide, etc., with agents that promote health, e.g. glutamate, and other agents typically provided to culture media as are known in the art of tissue culture.

Non-NR factor reagents of the NR system, e.g. agents that promote demethylation, agents that promote the survival and/ or differentiation of neurons or subtypes of neurons, agents that inhibit proliferation, and the like, may be provided to the cells prior to providing the NR factors. Alternatively, they may be provided concurrently with providing the NR factors. Alternatively, they may be provided subsequently to providing the NR factors.

The NR system is provided to non-neuronal somatic cells so as to reprogram, i.e. convert, those cells into induced neuronal cells. Non-neuronal somatic cells include any somatic cell that would not give rise to a neuron in the absence of experimental manipulation. Examples of non-neuronal somatic cells include differentiating or differentiated cells from ectodermal (e.g., keratinocytes), mesodermal (e.g., fibroblast), endodermal (e.g., pancreatic cells), hepatocytes, e.g. oval cells, etc.; or neural crest lineages (e.g. melanocytes). The somatic cells may be, for example, pancreatic beta cells, oligodendrocytes, astrocytes, hepatocytes, hepatic stem cells, cardiomyocytes, skeletal muscle cells, smooth muscle cells, hematopoietic cells, osteoclasts, osteoblasts, pericytes, vascular endothelial cells, schwann cells, and the like. They may be terminally differentiated cells, or they may be capable of giving rise to cells of a specific, non-neuronal lineage, e.g. cardiac stem cells, hepatic stem cells, and the like. The somatic cells are readily identifiable as non-neuronal by the absence of neuronal-specific markers that are well-known in the art, as described above.

In Vitro Methods of Conversion, and Uses for Cells Converted In Vitro

In some embodiments, the somatic cells are contacted in vitro with the NR system comprising NR factor(s). The subject cells may be from any mammal, including humans, primates, domestic and farm animals, and zoo, laboratory or pet animals, such as dogs, cats, cattle, horses, sheep, pigs, goats, rabbits, rats, mice etc. They may be established cell lines or they may be primary cells, where "primary cells", "primary cell lines", and "primary cultures" are used interchangeably herein to refer to cells and cells cultures that have been derived from a subject and allowed to grow in vitro for a limited number of passages.

The subject cells may be isolated from fresh or frozen cells, which may be from a neonate, a juvenile or an adult, and from tissues including skin, muscle, bone marrow, peripheral blood, umbilical cord blood, spleen, liver, pancreas, lung, intestine, stomach, adipose, and other differentiated tissues. The tissue may be obtained by biopsy or aphoresis from a live donor, or obtained from a dead or dying donor within about 48 hours of death, or freshly frozen tissue, tissue frozen within about 12 hours of death and maintained at below about $-20°$ C., usually at about liquid nitrogen temperature ($-190°$ C.) indefinitely. For isolation of cells from tissue, an appropriate solution may be used for dispersion or suspension. Such solution will generally be a balanced salt solution, e.g. normal saline, PBS, Hank's balanced salt solution, etc., conveniently supplemented with fetal calf serum or other naturally occurring factors, in conjunction with an acceptable buffer at low concentration, generally from 5-25 mM. Convenient buffers include HEPES, phosphate buffers, lactate buffers, etc.

Cells contacted in vitro with the NR system of reagents, i.e. the one or more NR factors and optionally the one or more other agents that promote reprogramming and promote the growth and/or differentiation of neurons, and the like, may be incubated in the presence of the reagent(s) for about 30 minutes to about 24 hours, e.g., 1 hours, 1.5 hours, 2 hours, 2.5 hours, 3 hours, 3.5 hours 4 hours, 5 hours, 6 hours, 7 hours, 8 hours, 12 hours, 16 hours, 18 hours, 20 hours, or any other period from about 30 minutes to about 24 hours, which may be repeated with a frequency of about every day to about every 4 days, e.g., every 1.5 days, every 2 days, every 3 days, or any other frequency from about every day to about every four days. The agent(s) may be provided to the subject cells one or more times, e.g. one time, twice, three times, or more than three times, and the cells allowed to incubate with the agent(s) for some amount of time following each contacting event e.g. 16-24 hours, after which time the media is replaced with fresh media and the cells are cultured further.

After contacting the non-neuronal somatic cells with the NR system, the contacted cells may be cultured so as to promote the survival and differentiation of neurons. Methods and reagents for culturing cells to promote the growth of neurons or particular subtypes of neurons and for isolating neurons or particular subtypes of neurons are well known in the art, any of which may be used in the present invention to grow and isolate the induced neuronal cells. For example, the somatic cells (either pre- or post-contacting with the NR factors) may be plated on Matrigel or other substrate as known in the art. The cells may be cultured in media such as N3, supplemented with factors. Alternatively, the contacted cells may be frozen at liquid nitrogen temperatures and stored for long periods of time, being capable of use on thawing. If frozen, the cells will usually be stored in a 10% DMSO, 50% FCS, 40% RPMI 1640 medium. Once thawed, the cells may be expanded by use of growth factors and/or stromal cells associated with neuronal survival and differentiation.

The effective amount of a NR system that may used to contact the somatic cells is an amount that induces at least 0.01% of the cells of the culture to increase expression of one or more genes known in the art to become more highly expressed upon the acquisition of a neuronal fate, e.g. Tau, Tuj1, MAP2, NeuN, and the like. An effective amount is the amount that induces an increase in expression of these genes that is about 1.5-fold or more, e.g. 1.5 fold, 2 fold, 3 fold, 4 fold, about 6 fold, about 10 fold greater than the level of expression observed in the absence of the NR system. The level of gene expression can be readily determined by any of a number of well-known methods in the art, e.g. by measuring RNA levels, e.g. by RT-PCR, quantitative RT-PCR, Northern blot, etc., and by measuring protein levels, e.g. Western blot, ELISA, fluorescence activated cell sorting, etc.

It is noted here that the contacted somatic cells do not need to be cultured under methods known in the art to promote pluripotency in order to be converted into induced neuronal cells. By pluripotency, it is meant that the cells have the ability to differentiate into all types of cells in an organism. In other words, the methods of the present invention do not require that the somatic cells of the present invention be provided with reprogramming factors known in the art to reprogram somatic cells to become pluripotent stem cells, i.e. iPS cells, e.g. Oct3/4, SOX2, KLF4, MYC, Nanog, or Lin28, and be cultured under conditions known in the art to promote pluripotent stem cell induction, e.g., as hanging droplets, in order for the subject cells to be reprogrammed into induced neuronal (iN) cells.

Following the methods of the invention, the contacted somatic cells will be converted into induced neuronal cells at an efficiency of reprogramming/efficiency of conversion that is at least about 0.01% of the total number of somatic cells cultured initially, e.g., 0.01%, 0.05%, 0.1%, 0.5%, 1%, 2%, 3%, 4%, 5%, 6%, 7%, 8%, 9%, 10%, 12%, 14%, 16%, 20% or more. At times, depending on the age of the donor, the origin of the tissue, or the culture conditions, higher efficiencies may be achieved. This efficiency of reprogramming is an enhanced efficiency over that which may be observed in the absence of NR factor(s). In other words, somatic cells and cell cultures have an enhanced ability to give rise to the desired type of cell when contacted with one or more NR factor(s) relative to cells that were not contacted with the NR factors. By enhanced, it is meant that the somatic cell cultures have the ability to give rise to the desired cell type that is 150% or greater than the ability of a somatic cell culture that was not contacted with the NR factor(s), e.g. 150%, 200%, 300%, 400%, 600%, 800%, 1000%, or 2000% of the ability of the uncontacted population. In other words, the culture of somatic cells produces about 1.5 fold, about 2-fold, about 3-fold, about 4-fold, about 6-fold, about 10-fold, about 20-fold, about 30-fold, about 50-fold, about 100-fold, about 200-fold the number of iN cells that are produced by a population of somatic cells that are not contacted with the NR factor(s). The efficiency of reprogramming may be determined by assaying the number of neurons that develop in the cell culture, e.g. by assaying the number of cells that express genes that are expressed by neurons, e.g. Tau, Tuj1, MAP2, and/or NeuN, and/or the number of cells that being to extend processes and make synaptic connections.

Induced neuronal (iN) cells produced by the above in vitro methods may be used in cell replacement or cell transplantation therapy to treat diseases. Specifically, iN cells may be transferred to subjects suffering from a wide range of diseases or disorders with a neuronal component, i.e. with neuronal symptoms, for example to reconstitute or supplement differentiating or differentiated neurons in a recipient.

The therapy may be directed at treating the cause of the disease; or alternatively, the therapy may be to treat the effects of the disease or condition. For example, the therapy may be directed at replacing neurons whose death caused the disease, e.g. motor neurons in Amyotrophic lateral sclerosis (ALS), or the therapy may be directed at replacing neurons that died as a result of the disease, e.g. photoreceptors in age related macular degeneration (AMD).

The iN cells may be transferred to, or close to, an injured site in a subject; or the cells can be introduced to the subject in a manner allowing the cells to migrate, or home, to the injured site. The transferred cells may advantageously replace the damaged or injured cells and allow improvement in the overall condition of the subject. In some instances, the transferred cells may stimulate tissue regeneration or repair.

In some cases, the iN cells or a sub-population of iN cells may be purified or isolated from the rest of the cell culture prior to transferring to the subject. In other words, one or more steps may be executed to enrich for the iN cells or a subpopulation of iN cells, i.e. to provide an enriched population of iN cells or subpopulation of iN cells. In some cases, one or more antibodies specific for a marker of cells of the neuronal lineage or a marker of a sub-population of cells of the neuronal lineage are incubated with the cell population and those bound cells are isolated. In other cases, the iN cells or a sub-population of the iN cells express a marker that is a reporter gene, e.g. EGFP, dsRED, lacz, and the like, that is under the control of a neuron-specific promoter or neuron-subtype specific promoter, e.g. Tau, GAD65, CAMK2A, VGLUT1, HB9, and the like, which is then used to purify or isolate the iN cells or a subpopulation thereof.

By a marker it is meant that, in cultures comprising somatic cells that have been reprogrammed to become iN cells, the marker is expressed only by the cells of the culture that will develop, are developing, and/or have developed into neurons. It will be understood by those of skill in the art that the stated expression levels reflect detectable amounts of the marker protein on or in the cell. A cell that is negative for staining (the level of binding of a marker-specific reagent is not detectably different from an isotype matched control) may still express minor amounts of the marker. And while it is commonplace in the art to refer to cells as "positive" or "negative" for a particular marker, actual expression levels are a quantitative trait. The number of molecules on the cell surface can vary by several logs, yet still be characterized as "positive".

Cells of interest, i.e. cells expressing the marker of choice, may be enriched for, that is, separated from the rest of the cell population, by a number of methods that are well known in the art. For example, flow cytometry, e.g. fluorescence activated cell sorting (FACS), may be used to separate the cell population based on the intrinsic fluorescence of the marker, or the binding of the marker to a specific fluorescent reagent, e.g. a fluorophor-conjugated antibody, as well as other parameters such as cell size and light scatter. In other words, selection of the cells may be effected by flow cytometry Although the absolute level of staining may differ with a particular fluorochrome and reagent preparation, the data can be normalized to a control. To normalize the distribution to a control, each cell is recorded as a data point having a particular intensity of staining. These data points may be displayed according to a log scale, where the unit of measure is arbitrary staining intensity. In one example, the brightest stained cells in a sample can be as much as 4 logs more intense than unstained cells. When displayed in this manner, it is clear that the cells falling in the highest log of staining intensity are bright, while those in the lowest intensity are negative. The "low" positively stained cells have a level of staining above the brightness of an isotype matched control, but are not as intense as the most brightly staining cells normally found in the population. An alternative control may utilize a substrate having a defined density of marker on its surface, for example a fabricated bead or cell line, which provides the positive control for intensity.

Other methods of separation, i.e. methods by which selection of cells may be effected, based upon markers include, for example, magnetic activated cell sorting (MACS), immunopanning, and laser capture microdissection.

One example of a protein of interest that may be used as a marker in the present invention is PSA-NCAM. PSA-NCAM is an NCAM polypeptide (GenBank Accession Nos. NM_000615.5 (isoform 1), NM_181351.3 (isoform 2) and NM_001076682.2 (isoform 3)) that is post-translationally modified by the addition of poly-sialic acid. A number of antibodies that are specific for PSA-NCAM are known in the art, including, e.g., anti-PSA-NCAM Clone 2-2B antibody (Millipore).

Another example of a marker that may be used is a fluorescent protein, e.g. GFP, RFP, dsRED, etc., operably linked to a neuron-specific promoter, e.g. Tau, PSA-NCAM, etc. In such embodiments, the marker and promoter are provided to the cell as an expression cassette on a vector, e.g. encoded on a DNA plasmid, encoded in a virus, and the like, The expression cassette may optionally contain other elements, e.g. enhancer sequences, other proteins for expression in the cell, and the like. In some embodiments, the expression cassette is provided to the cell prior to contacting the cell with NR factors, i.e. while the cell is still a somatic cell. In some embodiments, the expression cassette is provided to the cell at the same time as the cell is contacted with the NR factor. In some embodiments, the expression cassette is provided to the cell after the cell is contacted with the NR factors.

Enrichment of the iN population or a subpopulation of iNs may be performed about 3 days or more after contacting the somatic cells with the NR factors of the NR system, e.g. 3 days, 4 days, 5 days, 6 days, 7 days, 10 days, 14 days, or 21 days after contacting the somatic cells with the NR factors. Populations that are enriched by selecting for the expression of one or more markers will usually have at least about 80% cells of the selected phenotype, more usually at least 90% cells and may be 95% of the cells, or more, of the selected phenotype.

In some cases, genes may be introduced into the somatic cells or the cells derived therefrom, i.e. iNs, prior to transferring to a subject for a variety of purposes, e.g. to replace genes having a loss of function mutation, provide marker genes, etc. Alternatively, vectors are introduced that express antisense mRNA or ribozymes, thereby blocking expression of an undesired gene. Other methods of gene therapy are the introduction of drug resistance genes to enable normal progenitor cells to have an advantage and be subject to selective pressure, for example the multiple drug resistance gene (MDR), or anti-apoptosis genes, such as bcl-2. Various techniques known in the art may be used to introduce nucleic acids into the target cells, e.g. electroporation, calcium precipitated DNA, fusion, transfection, lipofection, infection and the like, as discussed above. The particular manner in which the DNA is introduced is not critical to the practice of the invention.

To prove that one has genetically modified the somatic cells or the cells derived therefrom, i.e. iNs, various techniques may be employed. The genome of the cells may be restricted and used with or without amplification. The polymerase chain reaction; gel electrophoresis; restriction analysis; Southern, Northern, and Western blots; sequencing; or the like, may all be employed. The cells may be grown under various conditions to ensure that the cells are capable of maturation to all of the neuronal lineages while maintaining the ability to express the introduced DNA. Various tests in vitro and in vivo may be employed to ensure that the neuronal phenotype of the derived cells has been maintained.

Subjects in need of neuron transplantation therapy, e.g. a subject suffering from a neurological condition associated with the loss of neurons or with aberrantly functioning neurons, could especially benefit from therapies that utilize cells derived by the methods of the invention. Examples of such diseases, disorders and conditions include neurodegenerative diseases (e.g. Parkinson's Disease, Alzheimer's Disease, Huntington's Disease, Amyotrophic Lateral Sclerosis (ALS), Spielmeyer-Vogt-Sjögren-Batten disease (Batten Disease), Frontotemporal Dementia with Parkinsonism, Progressive Supranuclear Palsy, Pick Disease, prion diseases (e.g. Creutzfeldt-Jakob disease), Amyloidosis, glaucoma, diabetic retinopathy, age related macular degeneration (AMD), and the like); neuropsychiatric disorders (e.g. anxiety disorders (e.g. obsessive compulsive disorder), mood disorders (e.g. depression), childhood disorders (e.g. attention deficit disorder, autistic disorders), cognitive disorders (e.g. delirium, dementia), schizophrenia, substance related disorders (e.g. addiction), eating disorders, and the like); channelopathies (e.g. epilepsy, migraine, and the like); lysosomal storage disorders (e.g. Tay-Sachs disease, Gaucher disease, Fabry disease, Pompe disease, Niemann-Pick disease, Mucopolysaccharidosis (MPS) & related diseases, and the like); autoimmune diseases of the CNS (e.g. Multiple Sclerosis, encephalomyelitis, paraneoplastic syndromes (e.g. cerebellar degeneration), autoimmune inner ear disease, opsoclonus myoclonus syndrome, and the like); cerebral infarction, stroke, and spinal cord injury.

In some approaches, the reprogrammed somatic cells, i.e. iNs, may be transplanted directly to an injured site to treat a neurological condition, see, e.g., Morizane et al., (2008), Cell Tissue Res., 331(1):323-326; Coutts and Keirstead (2008), Exp. Neurol., 209(2):368-377; Goswami and Rao (2007), Drugs, 10(10):713-719. For example, for the treatment of Parkinson's disease, neurons may be transplanted directly into the striate body of a subject with Parkinson's disease. As another example, for treatment of ALS, corticospinal motor neurons may be transplanted directly into the motor cortex of the subject with ALS. In other approaches, the cells derived by the methods of the invention are engineered to respond to cues that can target their migration into lesions for brain and spinal cord repair; see, e.g., Chen et al. (2007) Stem Cell Rev. 3(4):280-288.

The iNs may be administered in any physiologically acceptable medium. They may be provided prior to differentiation, i.e. they may be provided in an undifferentiated state and allowed to differentiate in vivo, or they may be allowed to differentiate for a period of time ex vivo and provided following differentiation. They may be provided alone or with a suitable substrate or matrix, e.g. to support their growth and/or organization in the tissue to which they are being transplanted. Usually, at least $1 \times 10^5$ cells will be administered, preferably $1 \times 10^6$ or more. The cells may be introduced to the subject via any of the following routes: parenteral, intravenous, intracranial, intraspinal, intraocular, or into spinal fluid. The cells may be introduced by injection, catheter, or the like. Examples of methods for local delivery, that is, delivery to the site of injury, include, e.g. through an Ommaya reservoir, e.g. for intrathecal delivery (see e.g. U.S. Pat. Nos. 5,222,982 and 5,385,582, incorporated herein by reference); by bolus injection, e.g. by a syringe, e.g. intravitreally or intracranially; by continuous infusion, e.g. by cannulation, e.g. with convection (see e.g. US Application No. 20070254842, incorporated here by reference); or by implanting a device upon which the cells have been reversably affixed (see e.g. US Application Nos. 20080081064 and 20090196903, incorporated herein by reference).

The number of administrations of treatment to a subject may vary. Introducing the iNs into the subject may be a one-time event; but in certain situations, such treatment may elicit improvement for a limited period of time and require an on-going series of repeated treatments. In other situations, multiple administrations of the iNs may be required before an effect is observed. The exact protocols depend upon the disease or condition, the stage of the disease and parameters of the individual subject being treated.

Additionally or alternatively, iNs produced by the above in vitro methods may be used as a basic research or drug discovery tool, for example to evaluate the phenotype of a genetic disease, e.g. to better understand the etiology of the disease, to identify target proteins for therapeutic treatment, to identify candidate agents with disease-modifying activity, i.e. an activity in modulating the survival or function of neurons in a subject suffering from a neurological disease or disorder, e.g. to identify an agent that will be efficacious in treating the subject. For example, a candidate agent may be added to a cell culture comprising iNs derived from the subject's somatic cells, and the effect of the candidate agent assessed by monitoring output parameters such as iN survival, the ability of the iNs to become depolarized, the extent to which the iNs form synapses, and the like, by methods described herein and in the art.

Parameters are quantifiable components of cells, particularly components that can be accurately measured, desirably in a high throughput system. A parameter can be any cell component or cell product including cell surface determinant, receptor, protein or conformational or posttranslational modification thereof, lipid, carbohydrate, organic or inorganic molecule, nucleic acid, e.g. mRNA, DNA, etc. or a portion derived from such a cell component or combinations thereof. While most parameters will provide a quantitative readout, in some instances a semi-quantitative or qualitative result will be acceptable. Readouts may include a single determined value, or may include mean, median value or the variance, etc. Characteristically a range of parameter readout values will be obtained for each parameter from a multiplicity of the same assays. Variability is expected and a range of values for each of the set of test parameters will be obtained using standard statistical methods with a common statistical method used to provide single values.

Candidate agents of interest for screening include known and unknown compounds that encompass numerous chemical classes, primarily organic molecules, which may include organometallic molecules, inorganic molecules, genetic sequences, etc. An important aspect of the invention is to evaluate candidate drugs, including toxicity testing; and the like.

Candidate agents include organic molecules comprising functional groups necessary for structural interactions, particularly hydrogen bonding, and typically include at least an amine, carbonyl, hydroxyl or carboxyl group, frequently at least two of the functional chemical groups. The candidate agents often comprise cyclical carbon or heterocyclic structures and/or aromatic or polyaromatic structures substituted with one or more of the above functional groups. Candidate agents are also found among biomolecules, including peptides, polynucleotides, saccharides, fatty acids, steroids, purines, pyrimidines, derivatives, structural analogs or combinations thereof. Included are pharmacologically active drugs, genetically active molecules, etc. Compounds of interest include chemotherapeutic agents, hormones or hormone antagonists, etc. Exemplary of pharmaceutical agents suitable for this invention are those described in, "The Pharmacological Basis of Therapeutics," Goodman and Gilman, McGraw-Hill, New York, N.Y., (1996), Ninth edition.

Compounds, including candidate agents, are obtained from a wide variety of sources including libraries of synthetic or natural compounds. For example, numerous means are available for random and directed synthesis of a wide variety of organic compounds, including biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Candidate agents are screened for biological activity by adding the agent to one or a plurality of cell samples, usually in conjunction with cells lacking the agent. The change in parameters in response to the agent is measured, and the result evaluated by comparison to reference cultures, e.g. in the presence and absence of the agent, obtained with other agents, etc.

The agents are conveniently added in solution, or readily soluble form, to the medium of cells in culture. The agents may be added in a flow-through system, as a stream, intermittent or continuous, or alternatively, adding a bolus of the compound, singly or incrementally, to an otherwise static solution. In a flow-through system, two fluids are used, where one is a physiologically neutral solution, and the other is the same solution with the test compound added. The first fluid is passed over the cells, followed by the second. In a single solution method, a bolus of the test compound is added to the volume of medium surrounding the cells. The overall concentrations of the components of the culture medium should not change significantly with the addition of the bolus, or between the two solutions in a flow through method.

A plurality of assays may be run in parallel with different agent concentrations to obtain a differential response to the various concentrations. As known in the art, determining the effective concentration of an agent typically uses a range of concentrations resulting from 1:10, or other log scale, dilutions. The concentrations may be further refined with a second series of dilutions, if necessary. Typically, one of these concentrations serves as a negative control, i.e. at zero concentration or below the level of detection of the agent or at or below the concentration of agent that does not give a detectable change in the phenotype.

In Vivo Methods of Conversion, and Uses for Cells Converted In Vivo

In some embodiments, a somatic cell is contacted in vivo with the NR system comprising NR factor(s), e.g. in a subject in need of neuron replacement therapy. Cells in vivo may be contacted with a SNTR system suitable for pharmaceutical use, i.e. a NR pharmaceutical composition, by any of a number of well-known methods in the art for the administration of polypeptides and nucleic acids to a subject. The NR pharmaceutical composition can be incorporated into a variety of formulations. More particularly, the NR pharmaceutical composition can be formulated into pharmaceutical compositions by combination with appropriate pharmaceutically acceptable carriers or diluents, and may be formulated into preparations in solid, semi-solid, liquid or gaseous forms, such as tablets, capsules, powders, granules, ointments, solutions, suppositories, injections, inhalants, gels, microspheres, and aerosols. As such, administration of the NR pharmaceutical composition can be achieved in various ways, including oral, buccal, rectal, parenteral, intraperitoneal, intradermal, transdermal, intracheal, etc., administration. The NR pharmaceutical composition may be systemic after administration or may be localized by the use of regional administration, intramural administration, or use of an implant that acts to retain the active dose at the site of implantation. The NR pharmaceutical composition may be formulated for immediate activity or they may be formulated for sustained release.

For some central nervous system conditions, it may be necessary to formulate the NR pharmaceutical composition, that is, the NR system comprising NR factor(s), to cross the blood brain barrier (BBB). One strategy for drug delivery through the blood brain barrier (BBB) entails disruption of the BBB, either by osmotic means such as mannitol or leukotrienes, or biochemically by the use of vasoactive substances such as bradykinin. A BBB disrupting agent can be co-administered with the therapeutic compositions of the invention when the compositions are administered by intravascular injection. Other strategies to go through the BBB may entail the use of endogenous transport systems, including caveoil-1 mediated transcytosis, carrier-mediated transporters such as glucose and amino acid carriers, receptor-mediated transcytosis for insulin or transferrin, and active efflux transporters such as p-glycoprotein. Active transport moieties may also be conjugated to the therapeutic compounds for use in the invention to facilitate transport across the endothelial wall of the blood vessel. Alternatively, drug delivery of the NR pharmaceutical composition behind the BBB may be by local delivery, for example by intrathecal delivery, e.g. through an Ommaya reservoir (see e.g. U.S. Pat. Nos. 5,222,982 and 5,385,582, incorporated herein by reference); by bolus injection, e.g. by a syringe, e.g. intravitreally or intracranially; by continuous infusion, e.g. by cannulation, e.g. with convection (see e.g. US Application No. 20070254842, incorporated here by reference); or by implanting a device upon which the NR pharmaceutical composition has been reversably affixed (see e.g. US Application Nos. 20080081064 and 20090196903, incorporated herein by reference).

The calculation of the effective amount or effective dose of the NR pharmaceutical composition to be administered is within the skill of one of ordinary skill in the art, and will be routine to those persons skilled in the art. Needless to say, the final amount to be administered will be dependent upon the route of administration and upon the nature of the disorder or condition that is to be treated.

For inclusion in a medicament, the NR pharmaceutical composition may be obtained from a suitable commercial source. As a general proposition, the total pharmaceutically effective amount of the compound administered parenterally per dose will be in a range that can be measured by a dose response curve.

The NR pharmaceutical composition to be used for therapeutic administration must be sterile. Sterility is readily accomplished by filtration through sterile filtration membranes (e.g., 0.2 µm membranes). Therapeutic compositions generally are placed into a container having a sterile access port, for example, an intravenous solution bag or vial having a stopper pierceable by a hypodermic injection needle. The NR pharmaceutical composition ordinarily will be stored in unit or multi-dose containers, for example, sealed ampules or vials, as an aqueous solution or as a lyophilized formulation for reconstitution. As an example of a lyophilized formulation, 10-mL vials are filled with 5 ml of sterile-filtered 1% (w/v) aqueous solution of compound, and the resulting mixture is lyophilized. The pharmaceutical composition comprising the lyophilized NR factor(s) is prepared by reconstituting the lyophilized compound, for example, by using bacteriostatic Water-for-Injection.

A NR system for pharmaceutical use, i.e. a NR pharmaceutical composition, can include, depending on the formulation desired, pharmaceutically-acceptable, non-toxic carriers of diluents, which are defined as vehicles commonly used to formulate pharmaceutical compositions for animal or human administration. The diluent is selected so as not to affect the biological activity of the combination. Examples of such diluents are distilled water, buffered water, physiological saline, PBS, Ringer's solution, dextrose solution, and Hank's solution. In addition, the NR pharmaceutical composition or formulation can include other carriers, adjuvants, or non-toxic, nontherapeutic, nonimmunogenic stabilizers, excipients and the like. The compositions can also include additional substances to approximate physiological conditions, such as pH adjusting and buffering agents, toxicity adjusting agents, wetting agents and detergents.

The composition can also include any of a variety of stabilizing agents, such as an antioxidant for example. When the pharmaceutical composition includes a polypeptide, the polypeptide can be complexed with various well-known compounds that enhance the in vivo stability of the polypeptide, or otherwise enhance its pharmacological properties (e.g., increase the half-life of the polypeptide, reduce its toxicity, enhance solubility or uptake). Examples of such modifications or complexing agents include sulfate, gluconate, citrate and phosphate. The polypeptides of a composition can also be complexed with molecules that enhance their in vivo attributes. Such molecules include, for example, carbohydrates, polyamines, amino acids, other peptides, ions (e.g., sodium, potassium, calcium, magnesium, manganese), and lipids.

Further guidance regarding formulations that are suitable for various types of administration can be found in Remington's Pharmaceutical Sciences, Mace Publishing Company, Philadelphia, Pa., 17th ed. (1985). For a brief review of methods for drug delivery, see, Langer, Science 249:1527-1533 (1990).

The NR pharmaceutical composition can be administered for prophylactic and/or therapeutic treatments. Toxicity and therapeutic efficacy of the active ingredient can be determined according to standard pharmaceutical procedures in cell cultures and/or experimental animals, including, for example, determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit large therapeutic indices are preferred.

The data obtained from cell culture and/or animal studies can be used in formulating a range of dosages for humans. The dosage of the active ingredient typically lines within a range of circulating concentrations that include the ED50 with low toxicity. The dosage can vary within this range depending upon the dosage form employed and the route of administration utilized.

The components used to formulate the pharmaceutical compositions are preferably of high purity and are substantially free of potentially harmful contaminants (e.g., at least National Food (NF) grade, generally at least analytical grade, and more typically at least pharmaceutical grade). Moreover, compositions intended for in vivo use are usually sterile. To the extent that a given compound must be synthesized prior to use, the resulting product is typically substantially free of any potentially toxic agents, particularly any endotoxins, which may be present during the synthesis or purification process. Compositions for parental administration are also sterile, substantially isotonic and made under GMP conditions.

The effective amount of a therapeutic composition to be given to a particular patient will depend on a variety of factors, several of which will differ from patient to patient. A competent clinician will be able to determine an effective amount of a therapeutic agent to administer to a patient to halt or reverse the progression the disease condition as required. Utilizing LD50 animal data, and other information available for the agent, a clinician can determine the maximum safe dose for an individual, depending on the route of administration. For instance, an intravenously administered dose may be more than an intrathecally administered dose, given the greater body of fluid into which the therapeutic composition is being administered. Similarly, compositions which are rapidly cleared from the body may be administered at higher doses, or in repeated doses, in order to maintain a therapeutic concentration. Utilizing ordinary skill, the competent clinician will be able to optimize the dosage of a particular therapeutic in the course of routine clinical trials.

Mammalian species that may be treated with the present methods include canines and felines; equines; bovines; ovines; etc. and primates, particularly humans. Animal models, particularly small mammals, e.g. murine, lagomorpha, etc. may be used for experimental investigations.

More particularly, the present invention finds use in the treatment of subjects, such as human patients, in need of neuron replacement therapy. Examples of such subjects would be subjects suffering from conditions associated with the loss of neurons or with aberrantly functioning neurons. Patients having diseases and disorders characterized by such conditions will benefit greatly by a treatment protocol of the pending claimed invention. Examples of such diseases, disorders and conditions include e.g., neurodegenerative diseases, neuropsychiatric disorders, channelopathies, lysosomal storage disorders, autoimmune diseases of the CNS, cerebral infarction, stroke, and spinal cord injury, as described previously.

An effective amount of a NR pharmaceutical composition is the amount that will result in an increase the number of neurons at the site of injury, and/or will result in measurable reduction in the rate of disease progression in vivo. For example, an effective amount of a NR pharmaceutical composition will inhibit the progression of symptoms e.g. loss of muscle control, loss of cognition, hearing loss, vision loss, etc. by at least about 5%, at least about 10%, at least about 20%, preferably from about 20% to about 50%, and even more preferably, by greater than 50% (e.g., from about 50% to about 100%) as compared to the appropriate control, the control typically being a subject not treated with the NR pharmaceutical composition. An agent is effective in vivo if administration of the agent at about 1 µg/kg to about 100 mg/kg body weight results in inhibition of symptoms within about 1 month to 3 months from the first administration of the pharmaceutical composition. In a specific aspect, body function may be improved relative to the amount of function observed at the start of therapy.

The methods of the present invention also find use in combined therapies, e.g. in with therapies that are already known in the art to provide relief from symptoms associated with the aforementioned diseases, disorders and conditions. The combined use of a NR pharmaceutical composition of the present invention and these other agents may have the advantages that the required dosages for the individual drugs is lower, and the effect of the different drugs complementary.

Astrocyte Reprogramming (AR) Factors and Systems

As discussed above, with the exception of the reprogramming factors and the reprogramming system used, the methods discussed herein also find use in converting non-astrocytic cells to astrocytes. For the conversion of non-astrocytic somatic cells to astrocytes, astrocyte reprogramming (AR) factors are used in place of NR factors. AR factors are biologically active factors that act on a cell to alter transcription so as to convert the cell into an astrocyte, i.e. an induced astrocyte (iA). AR factors are provided to somatic cells in the context of a AR system. Examples of AR factors include a Sox agent, a Tal agent, a Hes agent, an Id agent, and an Ascl agent.

The term Sox agent is used to refer to SOX (SRY (sex determining region Y)-box) polypeptides and the nucleic acids that encode them. Sox polypeptides are members of the SOX (SRY-related HMG-box) family of transcription factors involved in the regulation of embryonic development and in the determination of the cell fate. The terms "Sox gene product", "Sox polypeptide", and "Sox protein" are used interchangeably herein to refer to native sequence Sox polypeptides, Sox polypeptide variants, Sox polypeptide fragments and chimeric Sox polypeptides that can modulate transcription. Native sequence Sox polypeptides include the proteins Sox1 (GenBank Accession Nos. NM_005986.2 and NP_005977.2); Sox 2 (GenBank Accession Nos. NM_003106.2 and NP_003097.1); Sox3 (GenBank Accession Nos. NM_005634.2 and NP_005625.2); Sox4 (GenBank Accession Nos. NM_003107.2 and NP_003098.1); Sox5 (GenBank Accession Nos. NM_006940.4 and NP_008871.3 (isoform a), NM_152989.2 and NP_694534.1 (isoform b), and NM_178010.1 and NP_821078.1 (isoform c)); Sox6 (GenBank Accession Nos. NM_017508.2 and NP_059978.1 (isoform 1), NM_033326.3 and NP_201583.2 (isoform 2), NM_001145811.1 and NP_001139283.1 (isoform 3), and NM_001145819.1 and NP_001139291.1 (isoform 4)); Sox7 (GenBank Accession Nos. NM_031439.2 and NP_113627.1); Sox8 (GenBank Accession Nos. NM_014587.3 and NP_055402.2); Sox9 (GenBank Accession Nos. NM_000346.3 and NP_000337.1); Sox10 (GenBank Accession Nos. NM_006941.3 and NP_008872.1); Sox11 (GenBank Accession Nos. NM_003108.3 and NP_003099.1); Sox12 (also called Sox22; GenBank Accession Nos. NM_006943.2 and NP_008874.2); Sox13 (GenBank Accession Nos. NM_005686.2 and NP_005677.2); Sox14 (also called Sox28; GenBank Accession Nos. NM_004189.2 and NP_004180.1); Sox15 (also called Sox20, Sox26, and Sox27; GenBank Accession Nos. NM_006942.1 and NP_008873.1); Sox17 (GenBank Accession Nos. NM_022454.3 and NP_071899.1); Sox18 (GenBank Accession Nos. NM_018419.2 and NP_060889.1); Sox21 (also called Sox25; GenBank Accession Nos. NM_007084.2 and NP_009015.1); and Sox30 (GenBank Accession Nos. NM_178424.1 and NP_848511.1 (isoform a), and NM_007017.2 and NP_008948.1 (isoform b)). Sox polypeptides, e.g. those that are at least 50%, 55%, 60%, 65%, 70%, 75%, 80%, 85%, 90%, 91%, 92%, 95%, 97%, 99%, or are 100% identical to the sequence provided in the GenBank Accession Nos. above find use as reprogramming factors in the present invention, as do nucleic acids encoding these polypeptides or their transcriptionally active domains and vectors comprising these nucleic acids. In certain embodiments, the Sox agent is a Sox9 agent.

The term Tal agent is used to refer to Tal (T-cell acute lymphocytic leukemia) polypeptides and the nucleic acids that encode them. Tal polypeptides are basic helix-loop-helix transcription factors. The terms "Tal gene product", "Tal polypeptide", and "Tal protein" are used interchangeably herein to refer to native sequence Tal polypeptides, Tal polypeptide variants, Tal polypeptide fragments and chimeric Tal polypeptides that can modulate transcription. Native sequence Tal polypeptides include the proteins Tal1 (also called Scl and bHLHa17; GenBank Accession Nos. NM_003189.2 and NP_003180.1); and Tal2 (GenBank Accession Nos. NM_005421.2 and NP_005412.1). Tal polypeptides, e.g. those that are at least 50%, 55%, 60%, 65%, 70%, 75%, 80%, 85%, 90%, 91%, 92%, 95%, 97%, 99%, or are 100% identical to the sequence provided in the GenBank Accession Nos. above find use as reprogramming factors in the present invention, as do nucleic acids encoding these polypeptides or their transcriptionally active domains and vectors comprising these nucleic acids. In certain embodiments, the Tal agent is a Tal1 (Scl) agent.

The term Hes agent is used to refer to HES (Hairy and Enhancer of Split) polypeptides and the nucleic acids that encode them. HES polypeptides are basic helix loop helix transcription factors that act as a transcriptional repressors of other bHLH transcription factors. The terms "HES gene product", "HES polypeptide", and "HES protein" are used interchangeably herein to refer to native sequence HES polypeptides, HES polypeptide variants, HES polypeptide fragments and chimeric HES polypeptides that can modulate transcription. Native sequence HES polypeptides include the proteins Hes1 (GenBank Accession Nos. NM_005524.2 and NP_005515.1); Hes2 (GenBank Accession Nos. NM_019089.4 and NP_061962.2); Hes3 (GenBank Accession Nos. NM_001024598.2 and NP_001019769.1); Hes4 (GenBank Accession Nos. NM_001142467.1 and NP_001135939.1 (isoform 1), and NM_021170.3 and NP_066993.1 (isoform 2)); Hes5 (GenBank Accession Nos. NM_001010926.3 and NP_001010926.1); Hes6 (GenBank Accession Nos. NM_018645.4 and NP_061115.2 (isoform a), and NM_001142853.1 and NP_001136325.1 (isoform b)); and Hes7 (GenBank Accession Nos. kNM_001165967.1 and NP_001159439.1 (isoform 1), and NM_032580.3 and NP_115969.2 (isoform 2)). HES polypeptides, e.g. those that are at least 50%, 55%, 60%, 65%, 70%, 75%, 80%, 85%, 90%, 91%, 92%, 95%, 97%, 99%, or are 100% identical to the sequence provided in the GenBank Accession Nos. above find use as reprogramming factors in the present invention, as do nucleic acids encoding these polypeptides or their transcriptionally active domains and vectors comprising these nucleic acids. In certain embodiments, the HES agent is a Hes1 agent.

The term Id agent is used to refer to Id (Inhibitor of DNA binding) polypeptides and the nucleic acids that encode them. Id polypeptides are basic helix loop helix (bHLH) proteins that are capable of dimerizing with other bHLH proteins to inhibit these other bHLH proteins from binding DNA. The terms "Id gene product", "Id polypeptide", and "Id protein" are used interchangeably herein to refer to native sequence Id polypeptides, Id polypeptide variants, Id polypeptide fragments and chimeric Id polypeptides that can modulate transcription. Native sequence Id polypeptides include the proteins Id1 (GenBank Accession Nos. NM_002165.2 and NP_002156.2 (isoform a) and NM_181353.1 and NP_851998.1 (isoform b)); Id2 (GenBank Accession Nos. NM_002166.4 and NP_002157.2); Id3 (GenBank Accession Nos. NM_002167.3 and NP_002158.3); and Id4 (GenBank Accession Nos. NM_001546.2 and NP_001537.1). Id polypeptides, e.g. those that are at least 50%, 55%, 60%, 65%, 70%, 75%, 80%, 85%, 90%, 91%, 92%, 95%, 97%, 99%, or are 100% identical to the sequence provided in the GenBank Accession Nos. above find use as reprogramming factors in the present invention, as do nucleic acids encoding these polypeptides or their transcriptionally active domains and vectors comprising these nucleic acids. In certain embodiments, the Id agent is an Id1 agent.

Ascl agents are as described above, for NR factors. In certain embodiments, the Ascl agent that is a AR factor is an Ascl1 agent.

As with NR factors, in some embodiments, AR factors are provided as nuclear acting polypeptides. In some embodiments, AR factors are provided as nucleic acids encoding AR polypeptides, i.e. AR nucleic acids. Methods of preparing AR nuclear acting polypeptides and AR nucleic acids and of providing AR nuclear acting polypeptides and AR nucleic acids to the subject cells are as described above for NR nuclear acting polypeptides and NR nucleic acids.

As with NR factors, one or more AR factors may be provided to the cells. When more than one AR factors is provided, the AR factors may be provided individually or as a single composition, that is, as a premixed composition, of factors, simultaneously or sequentially, at the same molar ratio or at different molar ratios, once or multiple times in the course of culturing the cells.

As with NR system, in addition to the one or more AR factors, the AR system may include other reagents. Examples of such reagents include those described above for the NR system that are known in the art to promote cell reprogramming. Other reagents for optional inclusion in the AR system include those known in the art to promote the survival and differentiation of stem cells into astrocytes (see, e.g. Di Giorgio, F P (2007) Nat. Neurosci 19)5):608-14) and/or glial progenitors or astrocyte precursors into astrocytes (see, e.g. Christopherson, K S et al. (2005) Cell 120(3):421-433)

As with the NR system, reagents in the AR system may be provided in any culture media known in the art to promote cell survival.

The AR system is provided to non-astrocytic somatic cells or pluripotent cells as described above, so as to reprogram, i.e. convert, those cells into induced astrocytes. Non-astrocytic somatic cells include any somatic cell that would not give rise to an astrocyte in the absence of experimental manipulation. Examples of non-astrocytic somatic cells include differentiating or differentiated cells from ectodermal (e.g., keratinocytes), mesodermal (e.g., fibroblasts), or endodermal (e.g., pancreatic cells) lineages. The somatic cells may be, for example, pancreatic beta cells, oligodendrocytes, neurons, hepatocytes, hepatic stem cells, cardiomyocytes, skeletal muscle cells, smooth muscle cells, hematopoietic cells, osteoclasts, osteoblasts, pericytes, vascular endothelial cells, schwann cells, melanocytes and the like. They may be terminally differentiated cells, or they may be capable of giving rise to cells of a specific, non-astrocytic lineage, e.g. cardiac stem cells, hepatic stem cells, and the like. The somatic cells are readily identifiable as non-astrocytic by the absence of astrocyte-specific markers that are well-known in the art, as described above.

Induced astrocytes, be they induced in vitro and transplanted or induced in vivo, find use in treating subjects in need of astrocyte replacement therapy, e.g. subjects suffering from a neurological disease, disorder or condition associated with the loss of astrocytes or aberrantly functioning oligodendrocytes. Examples of such diseases would include Alzheimer's Disease and Amyotrophic Lateral Sclerosis.

May be I missed it, but iA cells could be of course also used in vitro for disease modeling (e.g. in coculture with wt neurons).

Oligodendrocyte Reprogramming (OR) Factors and Systems

As discussed above, with the exception of the reprogramming factors used and the reprogramming system used, the methods discussed herein for converting cells to neurons also find use in converting non-oligodendrocytic somatic cells to oligodendrocytes. Oligodendrocyte reprogramming (OR) factors are biologically active factors that act on a cell to alter transcription so as to convert the cell into an oligodendrocyte, i.e. an induced oligodendrocyte (iO). OR factors are provided to somatic cells or pluripotent cells in the context of an OR system. Examples of OR factors include a NRx2 agent, a MRF (Gm98) agent, an Olig agent, an Ascl1 agent, and a Sox agent.

The term NRx2 agent is used to refer to NRx2 (also called NK2, or NK2 transcription factor related, and TTF, for thyroid transcription factor) polypeptides and the nucleic acids that encode them. NRx2 polypeptides are homeodomain containing transcription factors. The terms "NRx2 gene product", "NRx2 polypeptide", and "NRx2 protein" are used interchangeably herein to refer to native sequence NRx2 polypeptides, NRx2 polypeptide variants, NRx2 polypeptide fragments and chimeric NRx2 polypeptides that can modulate transcription. Native sequence NRx2 polypeptides include the proteins NRx2-1 (GenBank Accession Nos. NM_001079668.2 and NP_001073136.1 (isoform 1) and NM_003317.3 and NP_003308.1 (isoform 2)); NRx2-2 (GenBank Accession Nos. NM_002509.2 and NP_002500.1); NRx2-3 (GenBank Accession Nos. NM_145285.2 and NP 660328.2); NRx2-4 (GenBank Accession Nos. NM_033176.1 and NP_149416.1); NRx2-5 (GenBank Accession Nos. NM_004387.3 and NP_004378.1 (isoform 1), NM_001166175.1 and NP_001159647.1 (isoform 2), and NM_001166176.1 and NP_001159648.1 (isoform 3); NRx2-6 (GenBank Accession Nos. NM_001136271.1 and NP_001129743.1); and NRx2-8 (also called NRx2-9, GenBank Accession Nos. NM_014360.2 and NP_055175.2) NRx2 polypeptides, e.g.

those that are at least 50%, 55%, 60%, 65%, 70%, 75%, 80%, 85%, 90%, 91%, 92%, 95%, 97%, 99%, or are 100% identical to the sequence provided in the GenBank Accession Nos. above find use as reprogramming factors in the present invention, as do nucleic acids encoding these polypeptides or their transcriptionally active domains and vectors comprising these nucleic acids. In certain embodiments, the NRx2 agent is a NRx2-2 agent.

The term MRF agent is used to refer to MRF (for myelin gene regulatory factor; or C11orf9, for chromosome 11 open reading frame 9; or Gm98) polypeptides and the nucleic acids that encode them. The terms "MRF gene product", "MRF polypeptide", and "MRF protein" are used interchangeably herein to refer to native sequence MRF polypeptides, MRF polypeptide variants, MRF polypeptide fragments and chimeric MRF polypeptides that can modulate transcription. Native sequence MRF polypeptides include the proteins encoded by GenBank Accession Nos. NM_013279.2 and NP_037411.1 (isoform 1) and NM_001127392.1 and NP_001120864.1 (isoform 2). MRF polypeptides, e.g. those that are at least 50%, 55%, 60%, 65%, 70%, 75%, 80%, 85%, 90%, 91%, 92%, 95%, 97%, 99%, or are 100% identical to the sequence provided in the GenBank Accession Nos. above find use as reprogramming factors in the present invention, as do nucleic acids encoding these polypeptides or their transcriptionally active domains and vectors comprising these nucleic acids.

Olig agents and Ascl agents are as described above for NR factors. In certain embodiments, the Olig agent that is a OR factor is an Olig1 or Olig 2 agent. In certain embodiments, the Ascl agent that is a OR factor is an Ascl1 agent.

Sox agents are as described above, for AR factors. In certain embodiments, the Sox agent that is an OR factor is a Sox10 agent.

As with NR factors, in some embodiments, OR factors are provided as nuclear acting polypeptides. In some embodiments, OR factors are provided as nucleic acids encoding OR polypeptides, i.e. OR nucleic acids. Methods of preparing OR nuclear acting polypeptides and OR nucleic acids and of providing OR nuclear acting polypeptides and OR nucleic acids to the subject cells are as described above for NR nuclear acting polypeptides and NR nucleic acids.

As with NR factors, one or more OR factors may be provided to the cells. When more than one OR factors is provided, the OR factors may be provided individually or as a single composition, that is, as a premixed composition, of factors, simultaneously or sequentially, at the same molar ratio or at different molar ratios, once or multiple times in the course of culturing the cells.

As with NR system, in addition to the one or more OR factors, the OR system may include other reagents. Examples of such reagents include those described above for the NR system that are known in the art to promote cell reprogramming. Other reagents for optional inclusion in the OR system include those known in the art to promote the survival and differentiation of stem cells into oligodendrocytes (see, e.g., Hu, B Y et al. (2009) Nat Protoc 4(11):1614-22; Parras, C M et al. (2007) J Neurosci 27(16):423-4242) and/or glial progenitors or oligodendrocyte precursors into oligodendrocytes (see, e.g., Dugas, J C et al. (2006) J Neurosci 26(43):10967-10983).

As with the NR system, reagents in the OR system may be provided in any culture media known in the art to promote cell survival.

The OR system is provided to non-oligodendrocytic somatic cells or pluripotent cells so as to reprogram, i.e. convert, those cells into induced oligodendrocytes. Non-oligodendrocytic somatic cells include any somatic cell that would not give rise to an oligodendrocyte in the absence of experimental manipulation. Examples of non-oligodendrocytic somatic cells include differentiating or differentiated cells from ectodermal (e.g., fibroblasts), mesodermal (e.g., myocytes), or endodermal (e.g., pancreatic cells) lineages. The somatic cells may be, for example, pancreatic beta cells, astroctyes, neurons, hepatocytes, hepatic stem cells, cardiomyocytes skeletal muscle cells, smooth muscle cells, hematopoietic cells, osteoclasts, osteoblasts, pericytes, vascular endothelial cells, and the like. They may be terminally differentiated cells, or they may be capable of giving rise to cells of a specific, non-oligodendrocytic lineage, e.g. cardiac stem cells, hepatic stem cells, and the like. The somatic cells are readily identifiable as non-oligodendrocytic by the absence of oligodendrocyte-specific markers that are well-known in the art, as described above.

Induced oligodendrocytes, be they induced in vitro and transplanted into a subject or induced in vivo, i.e. in the subject, find use in treating subjects in need of oligodendrocyte replacement therapy, e.g. subjects suffering from a neurological disease, disorder or condition associated with the loss of myelin, as from the loss of oligodendrocytes or aberrantly functioning oligodendrocytes. Examples of such diseases would include Multiple Sclerosis and Leukodystrophies.

Same here: disease modeling also possible (myelination disorders e.g. PMD or MS)

Neural Stem Cell Reprogramming (NSC)R Factors and Systems

As discussed above, with the exception of the reprogramming factors and the reprogramming systems used, the methods discussed herein for converting non-neuronal somatic cells into induced neurons also find use in converting postmitotic somatic cells of any cell lineage, or pluripotent stem cells, to neural stem cells (NSCs). NSC reprogramming (NSC)R factors are biologically active factors that act on a cell to alter transcription so as to convert the cell into a neural stem cell, i.e. an induced NSC (iNSC). (NSC)R factors are provided to somatic cells or pluripotent cells in the context of a (NSC)R system. Examples of (NSC)R factors include myc, Dlx, Klf, Lhx, Mef2, Nr2f, Pax, Rfx, NRx2, NRx6, FoxG, Sall, β-catenin, L3 mbtl, Ascl, Brn, Myt, Zic, Sox, Hes, and Id.

The term myc agent is used to refer to myc (also called v-myc myelocytomatosis viral oncogene homolog (avian)) polypeptides and the nucleic acids that encode them. myc polypeptides are transcription factors. The terms "myc gene product", "myc polypeptide", and "myc protein" are used interchangeably herein to refer to native sequence myc polypeptides, myc polypeptide variants, myc polypeptide fragments and chimeric myc polypeptides that can modulate transcription. Native sequence myc polypeptides include the proteins encoded by GenBank Accession Nos. NM_002467.4 and NP_002458.2. c-myc polypeptides, e.g. those that are at least 50%, 55%, 60%, 65%, 70%, 75%, 80%, 85%, 90%, 91%, 92%, 95%, 97%, 99%, or are 100% identical to the sequence provided in the GenBank Accession Nos. above find use as reprogramming factors in the present invention, as do nucleic acids encoding these polypeptides or their transcriptionally active domains and vectors comprising these nucleic acids.

The term Dlx agent is used to refer to Dlx (also called "distal-less homeobox") polypeptides and the nucleic acids that encode them. Dlx polypeptides are homeodomain containing transcription factors. The terms "Dlx gene product", "Dlx polypeptide", and "Dlx protein" are used interchangeably herein to refer to native sequence Dlx polypeptides, Dlx polypeptide variants, Dlx polypeptide fragments and chimeric Dlx polypeptides that can modulate transcription. Native sequence Dlx polypeptides include the proteins Dlx1 (GenBank Accession Nos. NM_178120.4 and NP_835221.2 (isoform 1), and NM_001038493.1 and NP_001033582.1 (isoform 2)); Dlx2 (GenBank Accession Nos. NM_004405.3 and NP_004396.1); Dlx3 (GenBank Accession Nos. NM_005220.2 and NP_005211.1); Dlx4 (also called Dlx7, Dlx8, and Dlx9; GenBank Accession Nos. NM_138281.2 and NP_612138.1 (isoform a), and NM_001934.2 and NP_001925.2 (isoform b)); Dlx5 (GenBank Accession Nos. NM_005221.5 and NP_005212.1); and Dlx6 (GenBank Accession Nos. NM_005222.2 and NP_005213.2). Dlx polypeptides, e.g. those that are at least 50%, 55%, 60%, 65%, 70%, 75%, 80%, 85%, 90%, 91%, 92%, 95%, 97%, 99%, or are 100% identical to the sequence provided in the GenBank Accession Nos. above find use as reprogramming factors in the present invention, as do nucleic acids encoding these polypeptides or their transcriptionally active domains and vectors comprising these nucleic acids. In certain embodiments, the Dlx agent is a Dlx1 agent.

The term Klf agent is used to refer to Klf (also called Kruppel like factor) polypeptides and the nucleic acids that encode them. Klf polypeptides are zinc-finger containing transcription factors. The terms "Klf gene product", "Klf polypeptide", and "Klf protein" are used interchangeably herein to refer to native sequence Klf polypeptides, Klf polypeptide variants, Klf polypeptide fragments and chimeric Klf polypeptides that can modulate transcription. Native sequence Klf polypeptides include the proteins Klf1 (GenBank Accession Nos. NM_006563.3 and NP_006554.1); Klf2 (GenBank Accession Nos. NM_016270.2 and NP_057354.1); Klf3 (GenBank Accession Nos. NM_016531.5 and NP_057615.3); Klf4 (GenBank Accession Nos. NM_004235.4 and NP_004226.3) Klf5 (GenBank Accession Nos. NM_001730.3 and NP_001721.2), Klf6 (GenBank Accession Nos. NM_001300.5 and NP_001291.3 (isoform a), NM_001160124.1 and NP_001153596.1 (isoform b), and NM_001160125.1 and NP_001153597.1 (isoform c)); Klf7 (GenBank Accession Nos. NM_003709.2 and NP_003700.1); Klf8 (GenBank Accession Nos. NM_007250.4 and NP_009181.2 (isoform 1), and NM_001159296.1 and NP_001152768.1 (isoform 2)); Klf9 (GenBank Accession Nos. NM_001206.2 and NP_001197.1); Klf10 (GenBank Accession Nos. NM_005655.2 and NP_005646.1 (isoform a) and NM_001032282.2 and NP_001027453.1 (isoform b)); Klf11 (GenBank Accession Nos. NM_003597.4 and NP_003588.1); Klf12 (GenBank Accession Nos. NM_007249.4 and NP_009180.3); Klf13 (GenBank Accession Nos. NM_015995.2 and NP_057079.2); Klf14 (GenBank Accession Nos. NM_138693.2 and NP_619638.1); Klf15 (GenBank Accession Nos. NM_014079.3 and NP_054798.1); Klf16 (GenBank Accession Nos. NM_031918.3 and NP_114124.1); and Klf17 (GenBank Accession Nos. NM_173484.3 and NP_775755.3). Klf polypeptides, e.g. those that are at least 50%, 55%, 60%, 65%, 70%, 75%, 80%, 85%, 90%, 91%, 92%, 95%, 97%, 99%, or are 100% identical to the sequence provided in the GenBank Accession Nos. above find use as reprogramming factors in the present invention, as do nucleic acids encoding these polypeptides or their transcriptionally active domains and vectors comprising these nucleic acids. In certain embodiments, the Klf agent is a Klf4 agent.

The term Lhx agent is used to refer to Lhx (also called LIM homeobox) polypeptides and the nucleic acids that encode them. Lhx polypeptides are homeodomain containing transcription factors with a LIM domain, a cysteine-rich zinc binding domain. The terms "Lhx gene product", "Lhx polypeptide", and "Lhx protein" are used interchangeably herein to refer to native sequence Lhx polypeptides, Lhx polypeptide variants, Lhx polypeptide fragments and chimeric Lhx polypeptides that can modulate transcription. Native sequence Lhx polypeptides include the proteins Lhx1 (also called LIM1; GenBank Accession Nos. NM_005568.2 and NP_005559.2); Lhx2 (GenBank Accession Nos. NM_004789.3 and NP_004780.3); Lhx3 (GenBank Accession Nos. NM_178138.3 and NP 835258.1 (isoform a), and NM_014564.2 and NP_055379.1 (isoform b)); Lhx4 (GenBank Accession Nos. NM_033343.2 and NP_203129.1); Lhx5 (GenBank Accession Nos. NM_022363.2 and NP_071758.1); Lhx6 (GenBank Accession Nos. NM_014368.3 and NP_055183.2 (isoform 1), and NM_199160.2 and NP_954629.2 (isoform 2)); Lhx7 (also called Lhx8; GenBank Accession Nos. NM_001001933.1 and NP_001001933.1); and Lhx9 (GenBank Accession Nos. NM_020204.2 and NP_064589.2 (isoform 1), and NM_001014434.1 and NP_001014434.1 (isoform 2)). Lhx polypeptides, e.g. those that are at least 50%, 55%, 60%, 65%, 70%, 75%, 80%, 85%, 90%, 91%, 92%, 95%, 97%, 99%, or are 100% identical to the sequence provided in the GenBank Accession Nos. above find use as reprogramming factors in the present invention, as do nucleic acids encoding these polypeptides or their transcriptionally active domains and vectors comprising these nucleic acids. In certain embodiments, the Lhx agent is a Lhx2 agent.

The term Mef2 agent is used to refer to Mef2 (also called myocyte enhancer factor 2) polypeptides and the nucleic acids that encode them. Mef2 polypeptides are members of the MADS gene family (so named for the yeast mating type-specific transcription factor MCM1, the plant homeotic genes 'agamous' and 'deficiens' and the human serum response factor SRF) of transcription factors. The terms "Mef2 gene product", "Mef2 polypeptide", and "Mef2 protein" are used interchangeably herein to refer to native sequence Mef2 polypeptides, Mef2 polypeptide variants, Mef2 polypeptide fragments and chimeric Mef2 polypeptides that can modulate transcription. Native sequence Mef2 polypeptides include the proteins Mef2a (GenBank Accession Nos. NM_005587.2 and NP_005578.2 (isoform 1), NM_001130926.1 and NP_001124398.1 (isoform 2), NM_001130927.1 and NP_001124399.1 (isoform 3), and NM_001130928.1 and NP_001124400.1 (isoform 4); Mef2b (GenBank Accession Nos. NM_001145785.1 and NP_001139257.1); Mef2c (GenBank Accession Nos. NM_002397.3 and NP_002388.2 (isoform 1) and NM_001131005.1 and NP_001124477.1 (isoform 2)); and Mef2d (GenBank Accession Nos. NM_005920.2 and NP_005911.1). Mef2 polypeptides, e.g. those that are at least 50%, 55%, 60%, 65%, 70%, 75%, 80%, 85%, 90%, 91%, 92%, 95%, 97%, 99%, or are 100% identical to the sequence provided in the GenBank Accession Nos. above find use as reprogramming factors in the present invention, as do nucleic acids encoding these polypeptides or their transcriptionally active domains and vectors comprising these nucleic acids. In certain embodiments, the Mef2 agent is a Mef2c agent.

The term Nr2f agent is used to refer to Nr2f (also called nuclear receptor subfamily 2, group F) polypeptides and the nucleic acids that encode them. Nr2f polypeptides are transcription factors. The terms "Nr2f gene product", "Nr2f polypeptide", and "Nr2f protein" are used interchangeably herein to refer to native sequence Nr2f polypeptides, Nr2f polypeptide variants, Nr2f polypeptide fragments and chimeric Nr2f polypeptides that can modulate transcription. Native sequence Nr2f polypeptides include the proteins Nr2f1 (also called COUP-TF1; GenBank Accession Nos. NM_005654.4 and NP_005645.1); and Nr2f2 (GenBank Accession Nos. NM_021005.3 and NP_066285.1 (isoform a), NM_001145155.1 and NP_001138627.1 (isoform b), and NM_001145156.1 and NP_001138628.1 (isoform c)). Nr2f polypeptides, e.g. those that are at least 50%, 55%, 60%, 65%, 70%, 75%, 80%, 85%, 90%, 91%, 92%, 95%, 97%, 99%, or are 100% identical to the sequence provided in the GenBank Accession Nos. above find use as reprogramming factors in the present invention, as do nucleic acids encoding these polypeptides or their transcriptionally active domains and vectors comprising these nucleic acids. In certain embodiments, the Nr2f agent is a Nr2f1 agent.

The term Pax agent is used to refer to Pax (also called Paired box) polypeptides and the nucleic acids that encode them. Pax polypeptides are paired-box containing transcription factors. The terms "Pax gene product", "Pax polypeptide", and "Pax protein" are used interchangeably herein to refer to native sequence Pax polypeptides, Pax polypeptide variants, Pax polypeptide fragments and chimeric Pax polypeptides that can modulate transcription. Native sequence Pax polypeptides include the proteins Pax1 (GenBank Accession Nos. NM_006192.3 and NP_006183.2); Pax2 (GenBank Accession Nos. NM_003987.3 and NP_003978.2 (isoform a), NM_000278.3 and NP_000269.2 (isoform b); NM_003988.3 and NP_003979.2 (isoform c); NM_003989.3 and NP_003980.2 (isoform d), and NM_003990.3 and NP_003981.2 (isoform e)); Pax3 (GenBank Accession Nos. NM_000438.4 and NP_000429.2); Pax4 (GenBank Accession Nos. NM_006193.2 and NP_006184.2); Pax5 (GenBank Accession Nos. NM_016734.1 and NP_057953.1); Pax6 (GenBank Accession Nos. NM_000280.3 and NP_000271.1); Pax7 (GenBank Accession Nos. NM_002584.2 and NP_002575.1); Pax8 (GenBank Accession Nos. NM_003466.3 and NP_003457.1); and Pax9 (GenBank Accession Nos. NM_006194.3 and NP_006185.1) Pax polypeptides, e.g. those that are at least 50%, 55%, 60%, 65%, 70%, 75%, 80%, 85%, 90%, 91%, 92%, 95%, 97%, 99%, or are 100% identical to the sequence provided in the GenBank Accession Nos. above find use as reprogramming factors in the present invention, as do nucleic acids encoding these polypeptides or their transcriptionally active domains and vectors comprising these nucleic acids. In certain embodiments, the Pax agent is a Pax6 agent.

The term Rfx agent is used to refer to Rfx (also called regulatory factor X (influences HLA class II expression)) polypeptides and the nucleic acids that encode them. Rfx polypeptides are transcription factors that contain a winged-helix DNA binding domain. The terms "Rfx gene product", "Rfx polypeptide", and "Rfx protein" are used interchangeably herein to refer to native sequence Rfx polypeptides, Rfx polypeptide variants, Rfx polypeptide fragments and chimeric Rfx polypeptides that can modulate transcription. Native sequence Rfx polypeptides include the proteins Rfx1 (GenBank Accession Nos. NM_002918.4 and NP_002909.4); Rfx2 (GenBank Accession Nos. NM_000635.3 and NP_000626.2 (isoform a) and NM_134433.2 and NP_602309.1 (isoform b)); Rfx3 (GenBank Accession Nos. NM_002919.2 and NP_002910.1 (isoform a), and NM_134428.1 and NP_602304.1 (isoform b)); Rfx4 (GenBank Accession Nos. NM_032491.4 and NP_115880.2 (isoform a), NM_002920.3 and NP_002911.2 (isoform b); and NM_213594.1 and NP_998759.1 (isoform c)); Rfx5 (GenBank Accession Nos. NM_000449.3 and NP_000440.1); Rfx6 (GenBank Accession Nos. NM_173560.2 and NP_775831.2); Rfx7 (GenBank Accession Nos. NM_022841.5 and NP_073752.5); and Rfx8 (GenBank Accession Nos. NM_001145664.1 and NP_001139136.1). Rfx polypeptides, e.g. those that are at least 50%, 55%, 60%, 65%, 70%, 75%, 80%, 85%, 90%, 91%, 92%, 95%, 97%, 99%, or are 100% identical to the sequence provided in the GenBank Accession Nos. above find use as reprogramming factors in the present invention, as do nucleic acids encoding these polypeptides or their transcriptionally active domains and vectors comprising these nucleic acids. In certain embodiments, the Rfx agent is a Rfx4 agent.

The term NRx6 agent is used to refer to NRx6 (also called NK6 homeobox) polypeptides and the nucleic acids that encode them. NRx6 polypeptides are homeodomain containing transcription factors. The terms "NRx6 gene product", "NRx6 polypeptide", and "NRx6 protein" are used interchangeably herein to refer to native sequence NRx6 polypeptides, NRx6 polypeptide variants, NRx6 polypeptide fragments and chimeric NRx6 polypeptides that can modulate transcription. Native sequence NRx6 polypeptides include the proteins NRx6-1 (GenBank Accession Nos. NM_006168.2→NP_006159.2); NRx6-2 (NM_177400.2→NP_796374.1); and NRx6-3 (NM_152568.2→NP_689781.1). NRx6 polypeptides, e.g. those that are at least 50%, 55%, 60%, 65%, 70%, 75%, 80%, 85%, 90%, 91%, 92%, 95%, 97%, 99%, or are 100% identical to the sequence provided in the GenBank Accession Nos. above find use as reprogramming factors in the present invention, as do nucleic acids encoding these polypeptides or their transcriptionally active domains and vectors comprising these nucleic acids. In certain embodiments, the NRx6 agent is a NRx6-1 or an NRx6-2 agent.

The term FoxG agent is used to refer to FoxG (also called forkhead box G) polypeptides and the nucleic acids that encode them. FoxG1 polypeptides are members of the forkhead family of transcription factors, and contain a forkhead domain. The terms "FoxG gene product", "FoxG polypeptide", and "FoxG protein" are used interchangeably herein to refer to native sequence FoxG polypeptides, FoxG polypeptide variants, FoxG polypeptide fragments and chimeric FoxG polypeptides that can modulate transcription. Native sequence FoxG polypeptides include the proteins FoxG1, encoded by GenBank Accession Nos. NM_005249.3 and NP_005240.3. FoxG polypeptides, e.g. those that are at least 50%, 55%, 60%, 65%, 70%, 75%, 80%, 85%, 90%, 91%, 92%, 95%, 97%, 99%, or are 100% identical to the sequence provided in the GenBank Accession Nos. above find use as reprogramming factors in the present invention, as do nucleic acids encoding these polypeptides or their transcriptionally active domains and vectors comprising these nucleic acids. In certain embodiments, the FoxG agent is a FoxG1 agent.

The term Sall agent is used to refer to Sall (also called Sal-like) polypeptides and the nucleic acids that encode them. Sall polypeptides are C2H2 zinc finger-containing transcription factors. The terms "Sall gene product", "Sall polypeptide", and "Sall protein" are used interchangeably herein to refer to native sequence Sall polypeptides, Sall polypeptide variants, Sall polypeptide fragments and chimeric Sall polypeptides that can modulate transcription. Native sequence Sall polypeptides include the proteins Sall1 (GenBank Accession Nos. NM_002968.2 and NP_002959.2 (isoform 1), and NM_001127892.1 and NP_001121364.1 (isoform 2)); Sall2 (GenBank Accession Nos.

NM_005407.1 and NP_005398.1); Sall3 (GenBank Accession Nos. NM_171999.2 and NP 741996.2); and Sall4 (GenBank Accession Nos. NM_020436.3 and NP_065169.1). Sall polypeptides, e.g. those that are at least 50%, 55%, 60%, 65%, 70%, 75%, 80%, 85%, 90%, 91%, 92%, 95%, 97%, 99%, or are 100% identical to the sequence provided in the GenBank Accession Nos. above find use as reprogramming factors in the present invention, as do nucleic acids encoding these polypeptides or their transcriptionally active domains and vectors comprising these nucleic acids. In certain embodiments, the Sall agent is a Sall3 agent.

The term β-catenin agent is used to refer to β-catenin polypeptides and the nucleic acids that encode them. The terms "β-catenin gene product", "β-catenin polypeptide", and "β-catenin protein" are used interchangeably herein to refer to native sequence β-catenin polypeptides, β-catenin polypeptide variants, β-catenin polypeptide fragments and chimeric β-catenin polypeptides that can modulate transcription. Native sequence β-catenin polypeptides include the proteins encoded by GenBank Accession Nos. NM_001098209.1 and NP_001091679.1. β-catenin polypeptides, e.g. those that are at least 50%, 55%, 60%, 65%, 70%, 75%, 80%, 85%, 90%, 91%, 92%, 95%, 97%, 99%, or are 100% identical to the sequence provided in the GenBank Accession Nos. above find use as reprogramming factors in the present invention, as do nucleic acids encoding these polypeptides or their transcriptionally active domains and vectors comprising these nucleic acids.

The term L3 mbtl agent is used to refer to L3 mbtl (for l(3) mbt-like (*Drosophila*)) polypeptides and the nucleic acids that encode them. L3 mbtl polypeptides are transcription factors that localize to condensed chromosomes in mitotic cells. The terms "L3 mbtl gene product", "L3 mbtl polypeptide", and "L3 mbtl protein" are used interchangeably herein to refer to native sequence L3 mbtl polypeptides, L3 mbtl polypeptide variants, L3 mbtl polypeptide fragments and chimeric L3 mbtl polypeptides that can modulate transcription. Native sequence L3 mbtl polypeptides include the proteins L3 mbtl1 (GenBank Accession Nos. NM_015478.5 and NP_056293.4 (isoform 1), and NM_032107.3 and NP_115479.3 (isoform 2)); L3 mbtl2 (GenBank Accession Nos. NM_031488.4 and NP_113676.2); L3 mbtl3 (GenBank Accession Nos. NM_032438.1 and NP_115814.1 (isoform a), and NM_001007102.1 and NP_001007103.1 (isoform b)); and L3 mbtl4 (GenBank Accession Nos. NM_173464.3 and NP_775735.2). L3 mbtl polypeptides, e.g. those that are at least 50%, 55%, 60%, 65%, 70%, 75%, 80%, 85%, 90%, 91%, 92%, 95%, 97%, 99%, or are 100% identical to the sequence provided in the GenBank Accession Nos. above find use as reprogramming factors in the present invention, as do nucleic acids encoding these polypeptides or their transcriptionally active domains and vectors comprising these nucleic acids. In certain embodiments, the L3 mbtl agent is a L3 mbtl1 agent.

Ascl, Brn, Myt, and Zic agents are as described above for NR factors. In certain embodiments, the Ascl agent that is a (NSC)R factor is an Ascl1 agent. In certain embodiments, the Brn agent that is a (NSC)R factor is an Brn2 or Brn4 agent. In certain embodiments, the Myt agent that is a (NSC)R factor is a Myt1 agent. In certain embodiments, the Zic agent that is a (NSC)R factor is a Zic1 agent.

Sox, Hes, and Id agents are as described above for AR factors. In certain embodiments, the Sox agent that is a (NSC)R factor is a Sox2 agent. In certain embodiments, the Hes agent that is a (NSC)R factor is a Hes1 or Hes5 agent. In certain embodiments, the Id agent that is a (NSC)R factor is an Id1 or Id4 agent.

NRx2 agents are as described above for OR factors. In certain embodiments, the NRx2 agent that is a (NSC)R factor is an NRx2-2 agent.

As with NR factors, in some embodiments, (NSC)R factor(s) are provided as nuclear acting polypeptides. In some embodiments, (NSC)R factors are provided as nucleic acids encoding (NSC)R polypeptides, i.e. (NSC)R nucleic acids. Methods of preparing (NSC)R nuclear acting polypeptides and (NSC)R nucleic acids and of providing (NSC)R nuclear acting polypeptides and (NSC)R nucleic acids to the subject cells are as described above for NR nuclear acting polypeptides and NR nucleic acids.

As with NR factors, one or more (NSC)R factors may be provided to the cells. When more than one (NSC)R factors is provided, the (NSC)R factors may be provided individually or as a single composition, that is, as a premixed composition, of factors, simultaneously or sequentially, at the same molar ratio or at different molar ratios, once or multiple times in the course of culturing the cells.

As with NR system, in addition to the one or more (NSC)R factors, the (NSC)R system may include other reagents. Examples of such reagents include those described above for the NR system that are known in the art to promote cell reprogramming. Other reagents for optional inclusion in the (NSC)R system include those known in the art to promote the survival and proliferation of neural stem cells, e.g. EGF, FGF2, and the like.

As with the NR system, reagents in the (NSC)R system may be provided in any culture media known in the art to promote cell survival and proliferation and neural stem cells, e.g. DMEM/F12.

One example of a (NSC)R system for use in the present methods is a system comprising DMEM/F12, 25 μg/ml insulin, 50 μg/ml transferrin, 30 nM sodium selenite, 20 nM progesterone (Sigma), 100 nM putrescine (Sigma), 10 ng/ml FGF2 (R&D Systems), 10 ng/ml EGF, and penicillin/streptomycin (see, e.g. Wernig M. et al. (2002) J. Neurosci Research 69:918-924). Daily additions of fibroblast growth factor-2 direct neural stem cells to become neuronal progenitor cells, and terminal differentiation into neurons may be induced by FGF2 withdrawal (Okabe S. et al. (1996) Mech Dev 59:89-102). Alternatively, daily additions of 10 ng/ml FGF2 and 10 ng/ml platelet-derived growth factor (PDGF)-AA (R&D Systems) direct neural stem cells to become glial progenitors, after which terminal differentiation into astrocytes and oligodendrocytes may be induced by growth factor withdrawal (for details of glial differentiation protocols, see, e.g. Brustle, O. et al. (1999) Science 285:754-756).

The (NSC)R system is provided to non-neural somatic cells or pluripotent cells so as to reprogram, i.e. convert, those cells into induced neural stem cells (iNSCs). Non-neural somatic cells include any somatic cell that would not give rise to a neuron in the absence of experimental manipulation. Examples of non-neural somatic cells include differentiating or differentiated cells from ectodermal (e.g., fibroblasts), mesodermal (e.g., myocytes), or endodermal (e.g., pancreatic cells) lineages. The somatic cells may be, for example, pancreatic beta cells, astroctyes, oligodendrocytes, hepatocytes, hepatic stem cells, cardiomyocytes skeletal muscle cells, smooth muscle cells, hematopoietic cells, osteoclasts, osteoblasts, pericytes, vascular endothelial cells, and the like. They may be terminally differentiated cells, or they may be capable of giving rise to cells of a specific, non-neural lineage, e.g. cardiac stem cells, hepatic stem cells, and the like. The somatic cells are readily identifiable as non-neural by the absence of neural-specific markers that are well-known in the art, as described above.

Induced neural stem cells, be they induced in vitro and transplanted into a subject or induced in vivo, i.e. in the subject, find use in treating subjects in need of neuronal replacement therapy, e.g. subjects suffering from a neurological disease, disorder or condition as discussed above.

Screening Methods.

The methods described herein also provide a useful system for screening candidate agents for activity in modulating cell conversion into somatic cells of a neural lineage, e.g. neurons, astrocytes, oligodendryocytes, or progenitor cells thereof. In screening assays for biologically active agents, cells, usually cultures of cells, are contacted with a candidate agent of interest in the presence of the cell reprogramming system or an incomplete cell reprogramming system, and the effect of the candidate agent is assessed by monitoring output parameters such as the level of expression of genes specific for the desired cell type, i.e. neuron, astrocyte, oligodendrocyte, or neural stem cell, as is known in the art, or the ability of the cells that are induced to function like the desired cell type, e.g. to propagate an action potential (for neurons), to promote synapse formation (for astrocytes), to produce myelin (for oligodendryocytes), to exit mitosis and differentiate into neurons, astroctyes, and/or oligodendrocytes (for neural stem cells); etc. as is known in the art.

For example, agents can be screened for an activity in promoting reprogramming of cells to a neuronal cell fate. For such a screen, a candidate agent may be added to a cell culture comprising candidate cells and a NR system or an incomplete NR system, where an observed increase in the level of RNA or protein of a neuronal gene, e.g. a 1.5-fold, a 2-fold, a 3-fold or more increase in the amount of RNA or protein from a neuronal-specific gene, e.g., Tau, Beta-III-Tubulin (encoding the protein Tuj1), MAP2, and the like, over that observed in the culture absent the candidate agent would be an indication that the candidate agent was an agent that promotes reprogramming to a neuronal fate. Reciprocally, an observed decrease in the level of RNA or protein of a neuronal gene, e.g. a 1.5-fold, a 2-fold, a 3-fold or more decrease in the amount of RNA or protein from a neuronal-specific gene, e.g., Tau, Tuji, MAP2, as compared to that observed in the culture absent the candidate agent would be an indication that the candidate agent was an agent that suppresses reprogramming to a neuronal fate. Incomplete NR systems, e.g. a NR system lacking one or more factors, or comprising sub-optimal levels of one or more factors, and the like, may be used in place of a complete NR system to increase the sensitivity of the screen.

As another example, agents can be screened for an activity in promoting the development of a neuron, e.g. the development of synapses by a neuron derived from a methods of the invention. In such a case, a candidate agent may be added to a cell culture comprising newly-induced neurons, e.g. neurons that were induced with a NR system 3 days, 4 days, 5 days, 6 days, 7 days or 10 days or more prior to contacting with the candidate agent. In some embodiments, the induced neurons are purified/isolated from the NR system-contacted culture and replated prior to contacting with the candidate agent, e.g. by methods described above for enriching for iN cells. In some embodiments, the induced neurons are contacted with the candidate agent in the context of the NR system, e.g. 2 days, 3 days, 5 days, 7 days or 10 days or more after the initial contact with the NR system. For example, in a screen of candidate agents that modulate synapse development, an observed increase in the spontaneous and rhythmic network activity at a holding potential of −70 mV, in the number of excitatory (EPSC) and inhibitory (IPSC) postsynaptic currents evoked, or in the number of synapsin-positive puncta surrounding MAP-2 positive dendrites as observed by immunohistochemistry, e.g. a 1.5-fold, a 2-fold, a 3-fold or more increase in these parameters, over that observed in the culture absent the candidate agent would be an indication that the candidate agent was an agent that promotes synapse formation. Reciprocally, an observed decrease in the spontaneous and rhythmic network activity at a holding potential of −70 mV, in the number of excitatory (EPSC) and inhibitory (IPSC) postsynaptic currents evoked, or in the number of synapsin-positive puncta surrounding MAP-2 positive dendrites as observed by immunohistochemistry, e.g. a 1.5-fold, a 2-fold, a 3-fold or more decrease in these parameters, as compared to that observed in the culture absent the candidate agent would be an indication that the candidate agent was an agent that suppresses synapse formation.

As discussed above with regard to uses for iNs produced by in vitro methods in screening candidate agents for those with an activity in modulating the survival or activity of neurons in a subject suffering from a neurological disease or disorder, candidate agents of interest for screening include known and unknown compounds that encompass numerous chemical classes, primarily organic molecules, which may include organometallic molecules, inorganic molecules, genetic sequences, etc. An important aspect of the invention is to evaluate candidate drugs, including toxicity testing; and the like.

Also as discussed above, compounds, including candidate agents, may be obtained from a wide variety of sources including libraries of synthetic or natural compounds. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Also as discussed above, candidate agents are screened for biological activity by adding the agent to one or a plurality of cell samples, usually in conjunction with cells lacking the agent. The change in parameters in response to the agent is measured, and the result evaluated by comparison to reference cultures, e.g. in the presence and absence of the agent, obtained with other agents, etc. As discussed above, the agents are conveniently added in solution, or readily soluble form, to the medium of cells in culture. The agents may be added in a flow-through system, as a stream, intermittent or continuous, or alternatively, adding a bolus of the compound, singly or incrementally, to an otherwise static solution.

A plurality of assays may be run in parallel with different agent concentrations to obtain a differential response to the various concentrations. As known in the art, determining the effective concentration of an agent typically uses a range of concentrations resulting from 1:10, or other log scale, dilutions. The concentrations may be further refined with a second series of dilutions, if necessary. Typically, one of these concentrations serves as a negative control, i.e. at zero concentration or below the level of detection of the agent or at or below the concentration of agent that does not give a detectable change in the phenotype.

Various methods can be utilized for quantifying the chosen parameters. For example, a convention method of measuring the presence or amount of a selected marker is to label a molecule with a detectable moiety, which may be fluorescent, luminescent, radioactive, enzymatically active, etc., particularly a molecule specific for binding to the parameter with high affinity. Fluorescent moieties are readily available for labeling virtually any biomolecule, structure, or cell type. Immunofluorescent moieties can be directed to bind not only to specific proteins but also specific conformations, cleavage products, or site modifications like phosphorylation. Individual peptides and proteins can be engineered to autofluoresce, e.g. by expressing them as green fluorescent protein chimeras inside cells (for a review see Jones et al. (1999) Trends Biotechnol. 17(12):477-81).

Kits may be provided, where the kit will comprise one or more factors to promote the conversion of cells into cells of a neural lineage. A combination of interest may include one or more NR, AR, OR or (NSC)R polypeptides or vectors comprising nucleic acids encoding those polypeptides and one or more other reagents of the NR, AR OR, or (NSC)R systems, respectively. Kits may further include cells or reagents suitable for isolating and culturing cells in preparation for conversion; reagents suitable for culturing neurons, astrocytes, oligodendrocytes, or neural stem cells following contacting with the NR, AR, OR, or (NSC)R system, respectively; and reagents useful for determining the expression of neuron-specific, astrocyte-specific, oligodendryocyte-specific, or neural stem cell-specific genes in the contacted cells, e.g. to determine effective doses of the NR/AR/OR/(NSC)R system. Kits may also include tubes, buffers, etc., and instructions for use.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Induction of Neuronal Cells from Mouse Fibroblasts

Materials and Methods

Embryonic Fibroblast Isolation.

Homozygous TauEGFP knock-in mice (Tucker, K. L., et al. (2001) Nat Neurosci 4, 29-37) were purchased from the Jackson Laboratories and bred with C57B16 mice (Taconic) to generate TauEGFP heterozygous embryos. Balb/c mice were purchased from Taconic. Rosa26-rtTA mice were obtained from Rudolf Jaenisch (Beard, C., et al. (2006) Genesis 44, 23-8). MEFs were isolated from E14.5 embryos under a dissection microscope (Leica). The head, vertebral column (containing the spinal cord), dorsal root ganglia, and all internal organs were removed and discarded to ensure the removal of all cells with neurogenic potential from the cultures. The remaining tissue was manually dissociated and incubated in 0.25% Trypsin (Sigma) for 10-15 minutes to create a single cell suspension. The cells from each embryo were plated onto a 15 cm tissue culture dish in MEF media (Dulbecco's Modified Eagle Medium (Invitrogen) containing 10% Fetal Bovine Serum (FBS) (Hyclone), beta-mercaptoethanol (Sigma-Aldrich), non-essential amino acids, sodium pyruvate, and penicillin/streptomycin (all from Invitrogen). Cells were grown at 37° C. for 4-7 days until confluent, and then split once before being frozen. After thawing, cells were cultured on 15 cm plates and allowed to become confluent before being split onto plates for infections using 0.25% Trypsin. Postnatal tail tip fibroblasts were prepared by removing the bottom third of tail from 3-day-old pups using surgical scissors. Cells were rinsed in ethanol, washed with HBSS (Sigma), and then dissociated using scissors and 0.25% Trypsin. Tail tip fibroblasts were cultured in MEF media until confluent and passaged once before being pooled together and frozen down for further use.

Cell Culture, Molecular Cloning and Infections.

We had three criteria for identifying candidates with neuron-inducing activity: (i) we reasoned that cell-fate inducing factors should be enriched in the gene category of transcriptional regulators. (ii) We included factors previously involved in reprogramming to pluripotency (Klf4, c-Myc, and Sox2). (iii) We searched for genes specifically expressed in neural tissues. Those were selected based on published expression arrays of MEFs, ES cells and neural progenitor cells retrieved from the Gene Expression Omnibus database GSE8024 and the EST Profile function of NCBI's Unigene database. cDNAs for the factors included in the nineteen factor pool were cloned into lentiviral constructs under the control of the tetracycline operator (Wernig, M. et al. (2008) Nat Biotechnol 26, 916-24). Replication-incompetent, VSVg-coated lentiviral particles were packaged in 293T cells as described (Wernig, M. et al. (2008) Nat Biotechnol 26, 916-24). Passage three TauEGFP and Balb/c MEFs were infected in MEF media containing polybrene (8 µg/mL). After 16-20 hours in media containing lentivirus, the cells were switched into fresh MEF media containing doxycycline (2 µg/mL) to activate expression of the transduced genes. After 48 hours in MEF media with doxycycline (Sigma), the media was replaced with N3 media 22 containing doxycycline. The media was changed every 2-3 days for the duration of the culture period. For BrdU experiments, 10 µM BrdU was added to the culture media and was maintained throughout media changes until the cells were fixed.

Immunofluorescence, RT-PCR and Flow Cytometry.

Neuronal cells were defined as cells, which stained positive for Tuj1 and had a process at least 3 times longer than the cell body. For immunofluorescence staining, cells were washed with PBS and then fixed with 4% paraformaldehyde for 10 minutes at room temperature (RT). Cells were then incubated in 0.2% Triton X-100 (Sigma) in PBS for 5 minutes at RT. After washing twice with PBS, cells were blocked in a solution of PBS containing 4% BSA, 1% FBS for 30 minutes at RT. Primary and secondary antibodies were diluted in a solution of PBS containing 4% BSA and 1% FBS. Fields of cells for staining were outlined with a PAP pen (DAKO). Primary and secondary antibodies were typically applied for 1 hour and 30 minutes, respectively. Cells were washed three times with PBS between primary and secondary staining. For anti-BrdU staining, cells were treated with 2N HCl in PBS for 10 minutes and washed twice with PBS before permeablization with TritonX-100 (Sigma). The following antibodies were used for our analysis: goat anti-ChAT (Millipore, 1:100), rabbit anti-GABA (Sigma, 1:4000), rabbit-GFAP (DAKO, 1:4000), mouse anti-MAP2 (Sigma, 1:500), mouse anti-NeuN (Millipore, 1:100), mouse anti-Peripherin (Sigma, 1:100), mouse anti-Sox2 (R&D Systems, 1:50), rabbit anti-Serotonin (Biogenesis, 1:1000), rabbit anti-Tuj1 (Covance, 1:1000), mouse anti-Tuj1 (Covance, 1:1000), goat anti-Brn2 (Santa Cruz Biotechnology, 1:100), mouse anti-BrdU (Becton-Dickinson, 1:3.5), mouse anti-Calretinin (DAKO, 1:100), sheep anti-Tyrosine Hydroxylase (Pel-Freez, 1:1000), E028 rabbit anti-synapsin (gift from Thomas Südhof, 1:500), guinea pig anti-vGLUT1 (Millipore, 1:2000), mouse anti-GAD6 (Developmental Studies Hybridoma Bank (DSHB), 1:500), mouse anti-Pax3 (DSHB, 1:250), mouse anti-Pax6 (DSHB, 1:50), mouse anti-Pax7 (DSHB, 1:250), mouse anti-NRx2.2 (DSHB, 1:100), mouse anti-Olig1 (NeuroMab, 1:100). Fitc-, and Cy3-conjugated secondary antibodies were obtained from Jackson Immunoresearch. Alexa-488, Alexa-546 and Alexa-633-conjugated secondary antibodies were obtained from Invitrogen. TauEGFP expressing cells were analyzed and sorted on a FACS Aria 2 (Becton Dickinson). Flow cytometry data was analyzed using Flowjo (Tree Star). For RT-PCR analysis, RNA was isolated using Trizol (Invitrogen) following the manufacturer's instructions, treated with DNAse (NEB) and 1.5 µg was reverse-transcribed with Superscript II (Invitrogen). PCR was performed using the following primers Sox1 (F-TCGAGCCCTTCT-CACTTGTT, R-TTGATGCATTTTGGGGGTAT), Sox10 (F-GAACTGGGCAAGGTCAAGAA, R-CGCTTGT-CACTTTCGTTCAG), β-Actin (F-CGTGGGCCGC-CCTAGGCACCA, R-CTTAGGGTTCAGGGGGGC). PCR products were analyzed on a 1% gel.

Efficiency Calculation.

The following method was used to calculate the efficiency of neuronal induction. The total number of Tuj1+ cells with a neuronal morphology, defined as a cell with a circular, three dimensional appearance and a thin process extending at least three times the length of the cell body, were quantified twelve days after infection. This estimate was based on the average number of iN cells present in 30 randomly selected 20× visual fields. The area of a 20× visual field was then measured, and we used this estimated density of iN cells to determine the total number of neurons present in the entire dish. We then divided this number by the number of cells plated before infection to get a percentage of the starting population of cells that adopted neuron-like characteristics.

Cortical Cultures.

Primary cortical neurons were isolated from newborn wildtype mice as described in Maximov, A., et al. (2007) J Neurosci Methods 161, 75-87, with modifications. Briefly, cortices were dissociated by papain (10 U/ml, with 1 µM $Ca^{2+}$, and 0.5 µM EGTA) digestions and plated on Matrigel coated circle glass coverslips (ø11 mm). The neurons were cultured in vitro in MEM (Invitrogen) supplemented with B27 (Invitrogen), glucose, transferrin, FBS and Ara-C (Sigma).

Glial Cell Isolation.

Forebrains were dissected from postnatal day five wild-type mice and were manually dissociated into ~0.5 $mm^2$ pieces in a total of 2 mL of HBSS. 500 µL of 2.5% Trypsin and 1% DNase were added and dissociated tissue was incubated at 37° for 15 minutes. Solution was mixed every 5 minutes. The supernatant was then transferred into 1.5 mL of Fetal bovine serum (FBS). 4 ml of HBSS, 500 µA 2.5% Trypsin, and 500 µA DNase were again added to the remaining dissociated tissue and incubated at 37° for 15 minutes, mixing every 5 minutes. The supernatant was again removed and added to the FBS-containing solution. Using a pipette, the remaining tissue was further dissociated and passed through a 70 µM nylon mesh filter (BD Biosciences) into the FBS-containing solution. The cell mixture was then spun at 1000 rpm for 5 minutes and resuspended in MEF media. Glial cells were passaged three times before culturing with MEF or TTF-derived iN cells. Contaminating neurons in p3 glial cell cultures could not be detected when stained for either Tuj1 or MAP2.

Electrophysiology.

Recordings were performed from MEF- and tail cell-derived iN cells at 8, 12 and 20 days after viral infection, or 7-13 days after co-culturing with cortical neurons. Spontaneous or evoked synaptic responses were recorded in the whole-cell voltage-clamp mode. Evoked synaptic responses were triggered by 1 ms current injection through a local extracellular electrode (FHC concentric bipolar electrode, Catalogue No. CBAEC75) with a Model 2100 Isolated Pulse Stimulator (A-M Systems, Inc.), and recorded in whole-cell mode using a Multiclamp 700B amplifier (Molecular Devices, Inc.) (Maximov, A. & Sudhof, T. C. (2005) Neuron 48, 547-54). Data were digitized at 10 kHz with a 2 kHz low-pass filter. The whole-cell pipette solution for synaptic current recordings contained: 135 mM CsCl, 10 mM HEPES, 1 mM EGTA, 4 mM Mg-ATP, 0.4 mM $Na_4GTP$, and 10 mM QX-314, pH 7.4. The bath solution contained (in mM): 140 mM NaCl, 5 mM KCl, 2 mM $CaCl_2$, 0.8 mM $MgCl_2$, 10 mM HEPES, and 10 mM glucose, pH 7.4. IPSCs were pharmacologically isolated by addition of 50 µM D-AP5 and 20 µM CNQX to the bath solution. EPSCs were pharmacologically isolated by addition of 30 µM picrotoxin and 50 µM D-APV. Data were analyzed using Clampfit 10.02 (Axon Instruments, Inc). Action potentials (APs) were recorded with current-clamp whole-cell configuration. The pipette solution for current clamp experiments contained (in mM) 123 mM K-gluconate, 10 mM KCl, 1 mM $MgCl_2$, 10 mM HEPES, 1 mM EGTA, 0.1 mM $CaCl_2$, 1 mM $K_2ATP$, 0.2 mM $Na_4GTP$, and 4 mM glucose, pH adjusted to 7.2 with KOH. Membrane potentials were kept around −65 to −70 mV, and step currents were injected to elicit action potential. Whole-cell currents including sodium currents, potassium currents were recorded at a holding potential of −70 mV, voltage steps ranging from −80 mV to +90 mV were delivered at 10 mV increments.

Results

A Screen for Neuronal Fate-Inducing Transcription Factors.

Reasoning that multiple transcription factors would likely be required to reprogram fibroblasts to a neuronal fate, we cloned a total of nineteen genes that are specifically expressed in neural tissues, play important roles in neural development, or have been implicated in epigenetic reprogramming (Table 1).

TABLE 1

Transcription factors screened for neuron-inducing activity in MEFs.

| Gene Name | Gene Bank |
| --- | --- |
| Ascl1 | NM_008553 |
| Brn2 | NM_008899 |
| Brn4 | NM_008901 |
| c-myc | NM_010849 |
| Dlx1 | NM_010053 |
| Hes5 | NM_010419 |
| Id1 | NM_010495 |
| Id4 | NM_031166 |
| Klf4 | NM_010637 |
| Lhx2 | NM_010710 |
| Mef2c | NM_025282 |
| Myt1l | NM_001093775 |
| NeuroD1 | NM_010894 |
| Nhlh1 | NM_010916 |
| Nr2f1 | NM_010151 |
| Olig2 | NM_016967 |
| Pax6 | NM_013627 |
| Sox2 | NM_011443 |
| Zic 1 | NM_009573 |

A pool of lentiviruses containing all nineteen genes (19F pool) was prepared to infect mouse embryonic fibroblasts (MEFs) from TauEGFP knock-in mice, which express EGFP specifically in neurons (Tucker, K. L., et al. (2001) Nat Neurosci 4, 29-37; Wernig, M. et al. (2002) J Neurosci Res 69, 918-24) (see FIG. 1a for experimental outline). Great care was taken to exclude neural tissue for the MEF isolation, and we were unable to detect evidence for the presence of neurons or neural progenitor cells in these cultures using immunofluorescence, fluorescence activated cell sorting (FACS), and RT-PCR analyses (FIG. 6). However, uninfected MEFs did contain rare Tuj1-positive, TauEGFP-negative cells with fibroblast-like morphology, indicative of weak Tuj1 (i.e. β-III-tubulin) expression in non-neuronal cells (FIG. 1b,c; FIG. 6a). In contrast, 32 days after infection with the 19F pool, we detected Tuj1-positive cells with typical neuronal morphologies and bright TauEGFP fluorescence (FIG. 1d,e). Thus, some combination(s) of the genes in the 19F pool was capable of converting MEFs into induced neuronal (iN) cells.

Figure 7:
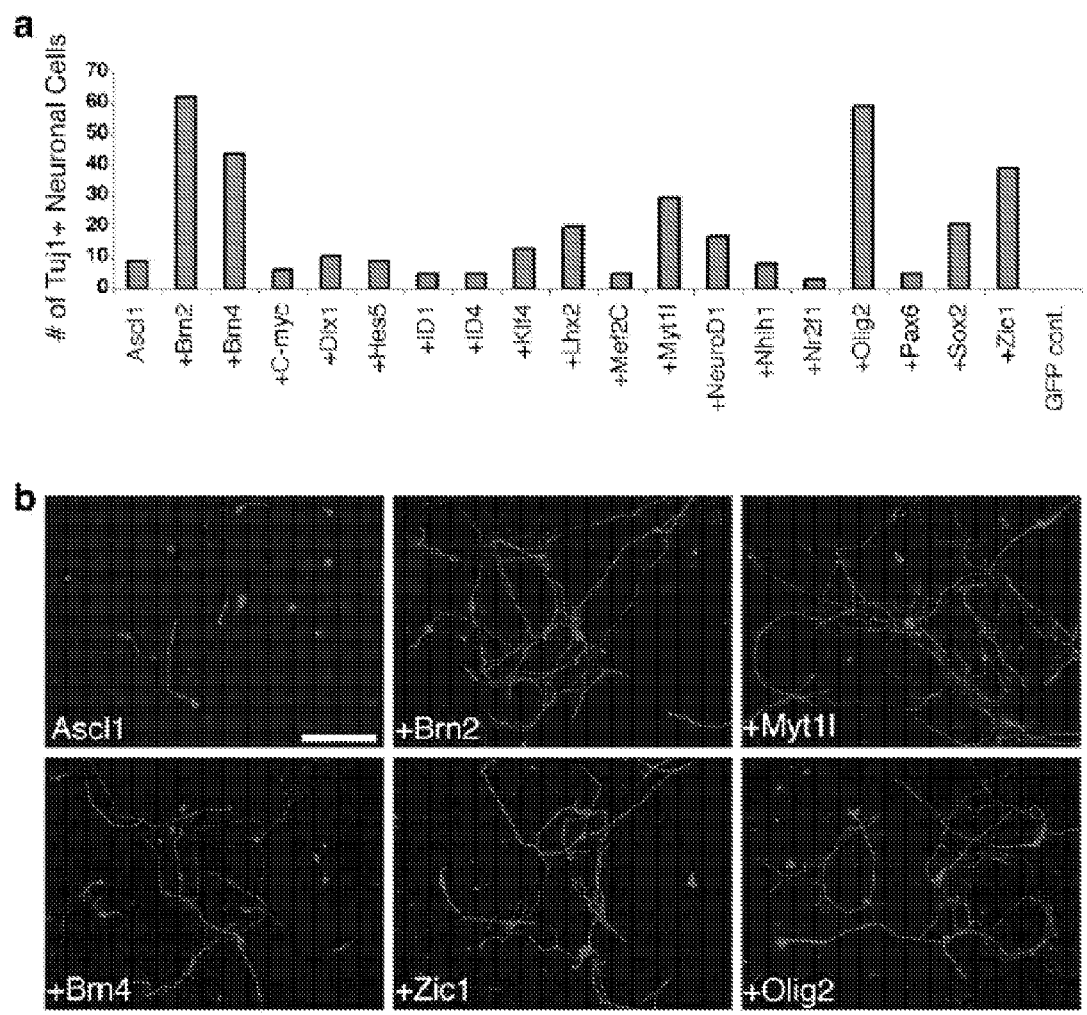
FIG. 7. Screen for enhancers of Ascl1-induced conversion. a, The effect of 18 transcription factors in combination with Ascl1 on neuronal induction 13 days post infection. Shown are the average numbers of Tuj1-positive cells with a process three times longer than the cell body derived from two randomly selected, low magnification visual fields. b, Representative Tuj1-positive cells 13 days after infection with Ascl1 alone or in combination with the indicated genes. Note the increased complexity of the neurites in the Ascl1+Myt1I condition.
Figure 8:
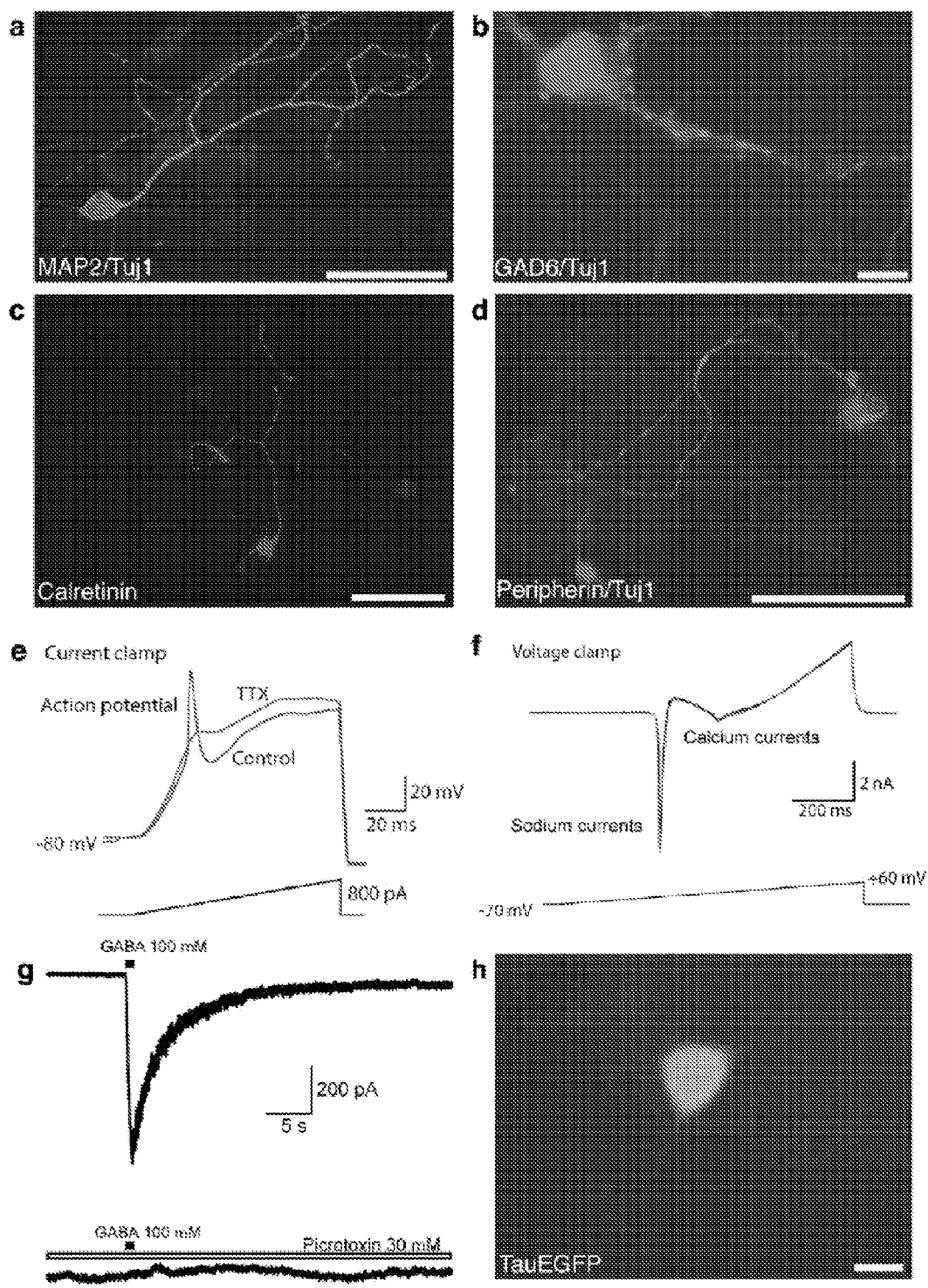
FIG. 8. Further immunohistochemical and electrophysiological characterization of 5F-iN cells. a, iN cells derived from Balb/c MEFs stained for MAP2 (red) and Tuj1 (green). b,c, At day 22 post-infection TauEGFP MEF-derived 5F iN cells rarely express GAD6. (b) Calretinin (red,c) and Tuj1 (green,c). d, An iN cell derived from Rosa26-rtTA TTFs that expressed the peripheral neuron marker peripherin (red) and Tuj1 (green). e, Representative traces of an action potential (AP) elicited using a ramp protocol (insert) from a TauEGFP MEF-derived iN cell at 8 days post infection. AP was abolished after application of TTX (both traces are from the same cell). f, Superimposed whole cell currents recorded by using a ramp protocol (insert) revealing fast-inactivating sodium current and inward calcium currents. g, TauEGFP MEF-derived iN cells respond to exogenous application of 100 µM GABA through a picosprizer. Lower panel showing that the GABA induced current response could be blocked by application of 30 µM picrotoxin. h, TauEGFP-expressing 5F iN cell observed in a MEF culture 5 days post infection. Scale bars=10 µm (b,h) and 100 µm (a,c,d).
Figure 10:
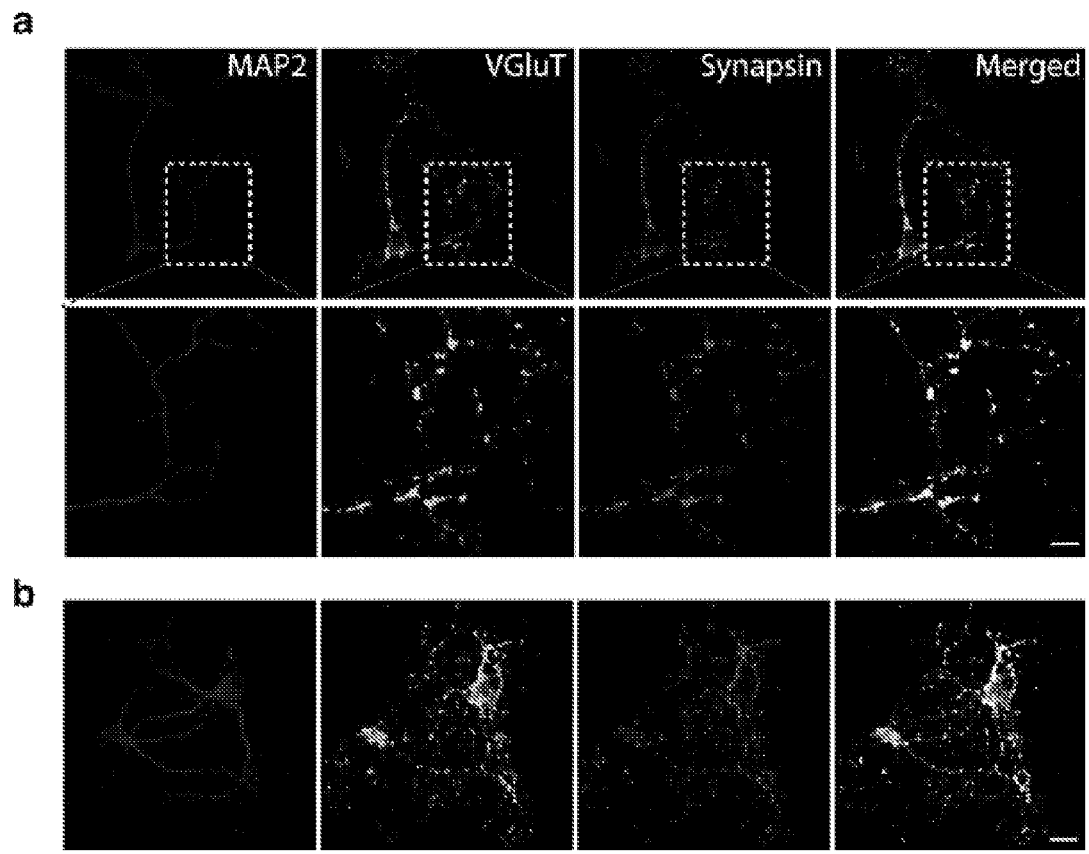
FIG. 10. Immunofluorescence of 5F-iN cells co-cultured with glial cells. a-b, MEF-derived 5F-iN cells on glia express markers of glutamatergic neurons. Immunostaining for vGLUT1, MAP2, and synapsin. The second row in b is a close-up of the outlined region in the first row. Scale Bars=10 µm (upper panel a, b), 3 µm (lower panel, a).

We next set out to narrow down the number of transcription factors required for generation of iN cells. Given their important roles in neuronal cell fate determination (Lee, J. E. et al. (1995) Science 268, 836-44; Guillemot, F. et al. (1993) Cell 75, 463-76; Farah, M. H. et al. (2000) Development 127, 693-702; Guillemot, F. (2005) Curr Opin Cell Biol 17, 639-47), we first tested the bHLH transcription factors Ascl1 (also known as Mash1), Ngn2 and Neurod1 individually. Surprisingly, we observed occasional Tuj1-, TauEGFP-positive cells exhibiting a simple mono- or bipolar morphology after infection with only Ascl1 (FIG. 7b), Ngn2 or NeuroD. However, 19F-iN cells exhibited more complex morphologies (compare to FIG. 1d,e). We therefore tested the neuron-inducing activity of Ascl1 in combination with each of the remaining eighteen candidate genes (FIG. 7a). Five genes (Brn2, Brn4, Myt1l, Zic1, and Olig2) substantially potentiated the neuron-inducing activity of Ascl1 (FIG. 7a-b). Importantly, none of these five genes generated iN cells when tested individually (data not shown). Next, we tested whether combinatorial expression of these factors with Ascl1 could further increase the induction of neuron-like cells by infecting TauEGFP MEFs with a pool of Brn2, Myt1I, Zic1, Olig2, and Ascl1 viruses (5F pool). Given its close similarity to Brn2, we did not include Brn4 in the 5F pool. Twelve days after infection, we detected a frequent Tuj1-positive iN cells with highly complex morphologies (FIG. 1f). These 5F-iN cells also expressed the pan-neuronal markers MAP2, NeuN, and synapsin (FIG. 1i-j, n). Similar results were obtained with iN cells derived from Balb/c MEFs (FIG. 8a)

Functional and Phenotypic Characterization of 5-Factor iN Cells.

To explore whether iN cells have functional membrane properties similar to neurons, we performed patch-clamp recordings of TauEGFP-positive cells on days 8, 12, and 20 after infection (see Tables 2, 3, 5-8, 10, 12-15, and 17-20 for detailed results). Action potentials could be elicited by depolarizing the membrane in current clamp mode the majority of the iN cells analyzed (85.1%, n=47) (FIG. 1k-l). Six cells (14.2%, n=42) exhibited spontaneous action potentials, some as early as eight days after transduction (FIG. 1m). These action potentials could be blocked by tetradotoxin (TTX), a specific inhibitor of Na+ ion channels (FIG. 8e). Moreover, in voltage-clamp mode we observed both fast, inactivating inward and outward currents, which likely correspond to opening of voltage-dependent K+- and Na+-channels, respectively, with a possible contribution of Ca2+-channels to the whole cell currents (FIG. 1l, FIG. 8f). The resting membrane potentials (RMP) ranged between −30 and −69 mV with an average of ~−55 mV on day 20 (n=12, FIG. 3c, Table 2). Additionally, we asked whether these cells possessed functional ligand-gated ion channels. iN cells responded to exogenous application of GABA, and this response could be blocked by the GABA receptor antagonist picrotoxin (FIG. 8g). Thus, MEF-derived iN cells appear to exhibit the functional membrane properties of neurons and possess ligand-gated GABA-receptors.

We then sought to characterize the neurotransmitter phenotype of iN cells. After 21 days of culture in minimal neuronal media, we detected vGLUT1-positive puncta outlining MAP2-positive neurites of some cells, indicating the presence of excitatory, glutamatergic neurons (FIG. 1o). In addition, we found iN cells labeled with antibodies against GABA, the major inhibitory neurotransmitter in brain (FIG. 1p). Some iN cells (9 out of ~500) contained the Ca2+-binding protein calretinin, a marker for cortical interneurons and other neuronal subtypes (FIG. 8c). No expression of tyrosine hydroxylase (TH), choline acetyltransferase (ChAT) or serotonin (5HT) was detected. The majority of iN cells were negative for peripherin, an intermediate filament characteristic of peripheral neurons (Escurat, M., et al. (1990) J Neurosci 10, 764-84).

Functional Neurons from Tail Fibroblasts.

Figure 2:
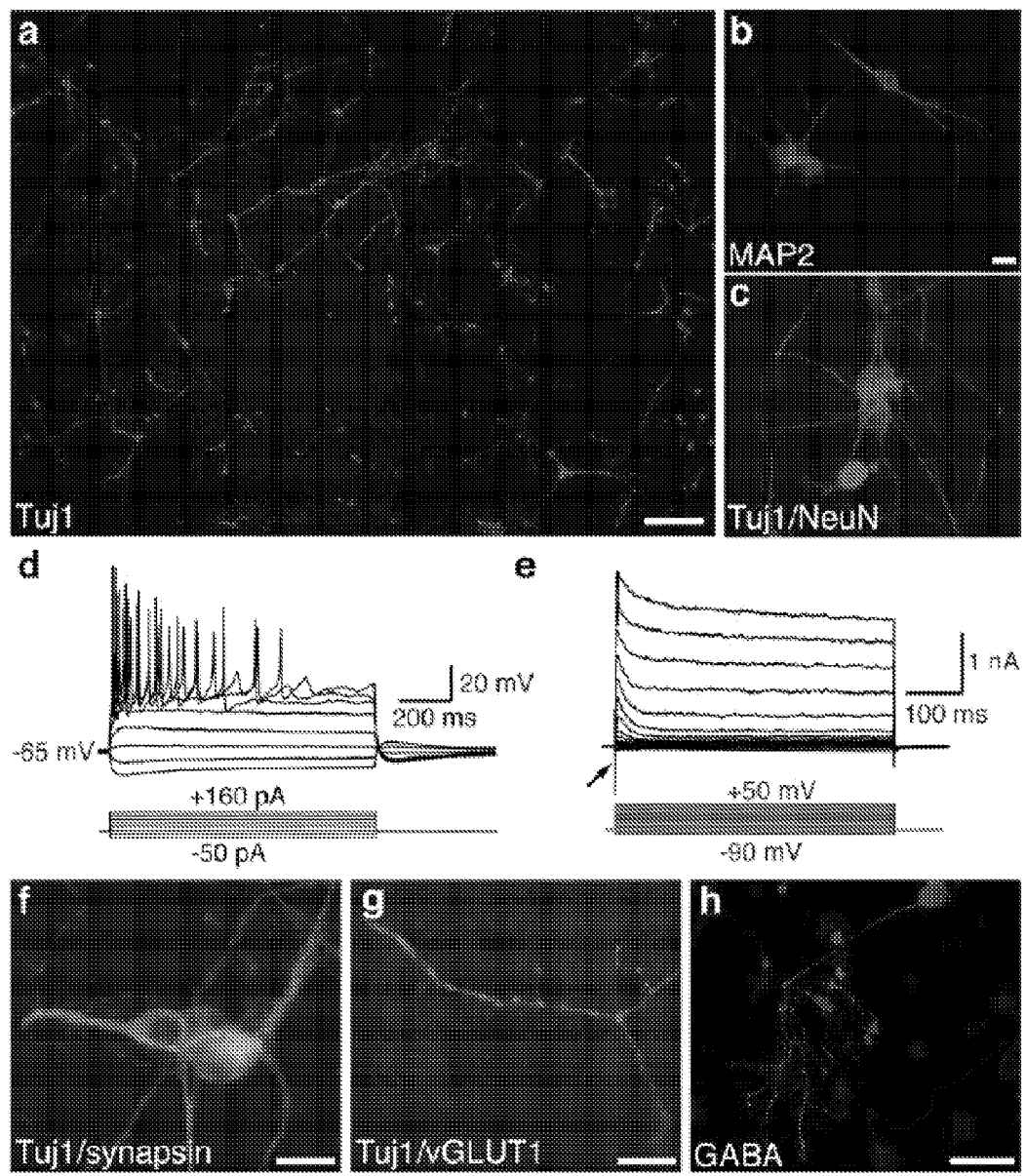
FIG. 2. Efficient induction of neurons from perinatal tail-tip fibroblasts. a, Tuj1-stained tail-tip fibroblast 13 days after infection 5F pool. b-c, TTF-iNs express the pan-neuronal markers MAP2 (b) and NeuN (c). d, Representative traces showing action potentials elicited at day 13 post infection. Nine of eleven cells recorded exhibited APs. e, Whole cell currents recorded in voltage-clamp mode. Inward fast inactivating sodium currents (arrow) and outward currents can be observed. f-h, 21 days after infection TTF-iN cells express synapsin (red, f), vGLUT1 (red, g) and GABA (h). c, f, and g are overlay images with the indicated marker (red) and Tuj1 (green). Scale bars=20 μm (b,f,g), 100 μm (h), 200 μm (a).

To evaluate whether iN cells could also be derived from postnatal cells, we isolated tail-tip fibroblasts (TTFs) from three-day-old TauEGFP and Rosa26-rtTA mice. Similar to our MEF cultures, we could not detect preexisting neurons, glia, or neural progenitor cells (FIG. 6a). Twelve days after infecting TTFs with the 5F pool, Tuj1-positive iN cells with a complex, neuronal morphology could be readily detected (FIG. 2a). TTF-iN cells expressed the pan-neuronal markers NeuN, MAP2, and synapsin (FIG. 2b-c, f). Electrophysiological recordings twelve days after infection demonstrated an average RMP of ~−57 mV (range: −35 to −70 mV, n=11), firing of APs (81.8%, n=11) (FIG. 2d), and expression of functional voltage-gated membrane channel proteins (FIG. 2e, and Tables 4, 6, 9, 11, and 16). We were also able to detect vGLUT1- as well as GABA-positive cells (FIG. 2g-h). Despite extensive screening (>1,000 iN cells analyzed), we were unable to detect tyrosine hydroxylase, choline-acetyltransferase, or serotonin expression. Individual iN cells exhibited peripherin-positive filaments (FIG. 8d).

TABLE 2

Electrophysiological parameters recorded from (MEF)-derived 5 factor (5F)-iN cells: Passive membrane properties.

|  | Average | SEM | n | P value (student t test) |
|---|---|---|---|---|
| Resting Membrane potentials (mV) | | | | |
| Day 8 | −30.8 | 3.2 | 16 | D8 vs. D12 0.000166; D7 Vs. D20: 0.000004 |
| Day 12 | −47.7 | 2.8 | 18 | D12 vs. D21: 0.0833 |
| Day 20 | −55.4 | 5.3 | 12 | |
| Membrane Input Resistance (GΩ) | | | | |
| Day 8 | 1.40 | 0.20 | 17 | D8 vs. D12: 000638; D8 vs. D20: 001962 |
| Day 12 | 0.60 | 0.10 | 21 | D12 vs. D20: 0343235 |
| Day 20 | 0.55 | 0.07 | 14 | |
| Membrane Capacitance (pF) | | | | |
| Day 8 | 27.9 | 2.8 | 18 | D8 vs. D12: 0.774473; D8 vs. D20: 0.020507 |
| Day 12 | 28.9 | 2.5 | 21 | D12 vs. D20: 0.016909 |
| Day 20 | 44.6 | 6.9 | 14 | |

TABLE 3

Electrophysiological parameters recorded from MEF-derived 5 factor (5F)-iN cells: Active membrane properties.

Spontaneous action potential firing and Induced Action potentials (AP)

|  | spontaneous | induced | No. of total recordings |
| --- | --- | --- | --- |
| Day 8 | 1 | 14 | 17 |
| Day 12 | 3 | 14 | 18 |
| Day 20 | 2 | 12 | 7 (spontaneous), 12 (induced) |

AP height (mV)

|  | Average | SEM | n | P value (student t test) |
| --- | --- | --- | --- | --- |
| Day 8 | 84.5 | 4.5 | 6 | D8 vs. D12: 0.5612; D8 vs. D20: 0.03558 |
| Day 12 | 81.3 | 3.0 | 14 | D12 vs. D20: 0.001843 |
| Day 20 | 94.9 | 2.3 | 12 | |

Note:
AP height was measured from baseline. APs were analyzed when first appeared during step depolarization. 7 cells at D8 are not included due to different protocol used; 1 cell at 7 days has clear AP but with distorted shape and thus not included.

AP threshold (mV)

|  | Average | SEM | n | P value (student t test) |
| --- | --- | --- | --- | --- |
| Day 8 | −25.2 | 1.5 | 6 | D8 vs. D12: 0.093417; D8 vs. D 20: 0.031866 |
| Day 12 | −29.0 | 1.3 | 14 | D12 vs. D20: 0.436939 |
| Day 20 | −30.5 | 1.4 | 12 | |

Note:
AP threshold was measured from the beginning of the upstroke of the action potential.

Maximal sodium current (NA)

|  | Average | SEM | n | P value (student t test) |
| --- | --- | --- | --- | --- |
| Day 8 | 700.2 | 257.2 | 5 | D8 vs. D12: 0.534945; D8 vs. D20: 0.091192 |
| Day 12 | 532.7 | 105.2 | 6 | D12 vs. D20: 0.050369 |
| Day 20 | 3615.0 | 1287.6 | 7 | |

Note:
Maximal sodium current were measured at voltage clamp mode using step depolarization protocol.

TABLE 4

Electrophysiological parameters recorded from TTF-derived 5 factor (5F)-iN cells: Passive and active membrane properties on day 12.

|  | Average | SEM | n |
| --- | --- | --- | --- |
| Resting membrane potential (mV) | −57.2 | 7.2 | 11 |
| Membrane input resistance (GΩ) | 0.3 | 0.0 | 11 |
| Membrane Capacitance (pF) | 26.1 | 1.4 | 11 |
| AP | Observed in 9 out of 11 cells, 2 of them fire repetitively | | |

TABLE 5

Electrophysiological parameters recorded from MEF-derived BAM-iN cells: Passive and active membrane properties (co-cultured with glia).

|  | Average | SEM | n |
| --- | --- | --- | --- |
| Membrane input resistance (GΩ) | 0.9 | 0.1 | 16 |
| Membrane Capacitance (pF) | 33.9 | 3.9 | 16 |
| AP | Not assayed due to use CsCl internal solutions. | | |

TABLE 6

Electrophysiological parameters recorded from TTF-derived BAM-iN cells: Passive and active membrane properties (co-cultured with glia).

|  | Average | SEM | n |
| --- | --- | --- | --- |
| Membrane input resistance (GΩ) | 0.5 | 0.1 | 12 |
| Membrane Capacitance (pF) | 35.4 | 5.3 | 12 |
| AP | Not assayed due to use CsCl internal solutions. | | |

TABLE 7

Electrophysiological parameters recorded from MEF-derived 5F-iN cells: Synaptic functions (co-cultured with glia).

|  | Average | SEM | n | No. of total recordings |
| --- | --- | --- | --- | --- |
| AMPA EPSCS | 229.6 | 75.2 | 8 | 11 |
| NMDA EPSCS | 743.9 | 224.8 | 9 | 11 |

TABLE 7-continued

Electrophysiological parameters recorded from MEF-derived 5F-iN cells: Synaptic functions (co-cultured with glia).

|  | Average | SEM | n | No. of total recordings |
|---|---|---|---|---|
| Spontaneous PSCs | observed in 5 cells |  |  | 11 |
| IPSCs | No obvious events observed, 11 recordings without blockers, 4 with APV + CNQX |  |  |  |

Note:
AMPA EPSCs were recorded at Vh of −70 mV; NMDA EPSCs were recorded at +60 mV and measured at 50 ms after stimulation. Spontaneous PSCs were recorded in the absence of blockers.

TABLE 8

Electrophysiological parameters recorded from MEF-derived 5F-iN cells: Synaptic integrations (co-cultured with cortical neurons).

|  | Average | SEM | n | No. of total recordings |
|---|---|---|---|---|
| IPSC Amplitude (pA) | 1228.2 | 275.1 | 13 | 15 |
| AMPA EPSC Amplitude (pA) | 94.7 | 21.5 | 8 | 9 |
| NMDA EPSC Amplitude (pA) | 283.4 | 89.4 | 9 | 9 |
| Spontaneous PSCs | observed in 6 cells |  |  | 6 |
| Evoked PSCs | compond PSCs observed in 6 cells |  |  | 6 |
| Spontaneous IPSCs | observed in 13 cells |  |  | 15 |
| Spontaneous EPSCS | observed in 4 cells |  |  | 9 |

Note:
PSCs were recorded without blockers; IPSC: in APV and CNQX; EPSC: in picrotoxin.

TABLE 9

Electrophysiological parameters recorded from TTF-derived 5F-iN cells: Synaptic integrations (co-cultured with cortical neurons).

| Spontaneous PSCs | observed in 2 out of 3 cells recorded |
|---|---|
| Evoked PSCs | compound evoked PSCs observed in 2 out of 3 cells |

Note:
No blockers were added to these recordings.

TABLE 10

Electrophysiological parameters recorded from MEF-derived BAM-iN cells: Synaptic function (co-cultured with cortical glia).

|  | Average | SEM | n | No. of total recordings |
|---|---|---|---|---|
| AMPA EPSC Amplitude (pA) | 41.7 | 11.9 | 9 | 16 |
| NMDA EPSC Amplitude (pA) | 130 | 33.8 | 11 | 16 |
| Spontaneous PSCs | observed in 3 cells |  |  | 16 |
| IPSC Amplitude (pA) | not detected |  |  | 16 |

Note:
AMPA EPSCs were recorded at Vh of −70 mV; NMDA EPSCs were recorded at +60 mV and measured at 50 ms after stimulation.

TABLE 11

Electrophysiological parameters recorded from TTF-derived BAM-iN cells: Synaptic function (co-cultured with glia).

|  | Average | SEM | n | No. of total recordings |
|---|---|---|---|---|
| AMPA EPSC Amplitude (pA) | 82.8 | 27.3 | 5 | 12 |
| NMDA EPSC Amplitude (pA) | 208.7 | 75.0 | 6 | 12 |
| Spontaneous PSCs | observed in 3 cells |  |  | 12 |
| IPSC Amplitude (pA) | not detected |  |  | 12 |

Note:
AMPA EPSCs were recorded at Vh of −70 mV; NMDA EPSCs were recorded at +60 mV and measured at 50 ms after stimulation.

TABLE 12

Electrophysiological parameters recorded from MEFs infected with Ascl1, Brn2, Myt1l: Membrane properties on Day 12.

|  | Average | SEM | n | P value (student t test) |
|---|---|---|---|---|
| Membrane properties of MEFs infected with Ascl 1, Brn2, Myt1l: Day 12 | | | | |
| Ascl1 | −48.6 | 3.4 | 11 | A vs AB: 0.729261; A. vs. AM: 0.318123; A vs. 3F: 0.378688 |
| Ascl1 + Brn2 | −47.3 | 1.8 | 12 | AB vs. AM: 0.08692; AB vs. 3F: 0.125888 |
| Ascl1 + Myt1l | −52.9 | 2.6 | 12 | AM vs. 3F: 0.885015 |
| BAM | −52.4 | 2.6 | 13 |  |
| Membrane Input Resistance (mΩ) | | | | |
| Ascl1 | 0.95 | 0.14 | 11 | A vs AB: 0.192394; A. vs. AM: 0.074357; A vs. 3F: 0.951576 |
| Ascl1 + Brn2 | 1.31 | 0.22 | 12 | AB vs. AM: 0.010736; AB vs. 3F: 0.144018 |
| Ascl1 + Myt1l | 0.64 | 0.09 | 12 | AM vs. 3F: 0.019898 |
| BAM | 0.96 | 0.09 | 13 |  |
| Membrane Capacitance (pF) | | | | |
| Ascl1 | 18.7 | 1.1 | 11 | A vs AB: 0.60362; A vs AM: 0.243535; A vs. ABM: 0.01028 |
| Ascl1 + Brn2 | 19.8 | 1.7 | 12 | AB vs. AM: 0.534332; AB vs. ABM: 0.025714 |
| Ascl1 + Myt1l | 21.5 | 2.0 | 12 | AM vs. ABM: 0.076441 |
| BAM | 28.1 | 2.9 | 13 |  |

Spontaneous AP filing and induced AP

|  | spontaneous | induced | No. of total recordings |
|---|---|---|---|
| Ascl1 | 0 | 9 | 11 |
| Ascl1 + Brn2 | 0 | 12 | 12 |
| Ascl1 + Myt1l | 1 | 11 | 12 |
| BAM | 3 | 13 | 13 |

TABLE 13

Resting membrane potentials, membrane input resistances and membrane capacities of MEF-derived 5F-iN cells on Day 8. RMP: resting membrane potential; Rm: membrane input resistance; Cm: membrane capacitance. Note that in some cases, different internal solutions were used, which did not allow for the measurement of RMP.

|  | RMP (mV) | Rm (GΩ) | Cm (pF) |
|---|---|---|---|
| MEF-derived 5F-iN cells: Day 8 | | | |
| Cell 1 | −38 | 2.80 | 29 |
| Cell 2 | −34 | 2.10 | 13 |
| Cell 3 | −34 | 0.46 | 23 |
| Cell 4 | −30 | 1.10 | 30 |
| Cell 5 | −20 |  |  |
| Cell 6 | −20 | 0.96 | 32 |
| Cell 7 | −20 | 1.50 | 28 |

TABLE 13-continued

Resting membrane potentials, membrane input resistances and membrane capacities of MEF-derived 5F-iN cells on Day 8. RMP: resting membrane potential; Rm: membrane input resistance; Cm: membrane capacitance. Note that in some cases, different internal solutions were used, which did not allow for the measurement of RMP.

| | RMP (mV) | Rm (GΩ) | Cm (pF) |
|---|---|---|---|
| | MEF-derived 5F-iN cells: Day 8 | | |
| Cell 8 | −16 | 3.70 | 24 |
| Cell 9 | | 2.70 | 46 |
| Cell 10 | −45 | 0.41 | 39 |
| Cell 11 | −30 | 1.60 | 22 |
| Cell 12 | −50 | 0.65 | 17 |
| Cell 13 | −33 | 2.00 | 12 |
| Cell 14 | −45 | 0.74 | 31 |
| Cell 15 | −28 | 1.80 | 29 |
| Cell 16 | −16 | 0.85 | 25 |
| Cell 17 | −35 | 1.60 | 26 |
| Cell 18 | −40 | 0.49 | 47 |
| Cell 19 | −16 | 1.00 | 33 |

Note:
Cell 1 Rs is 40 Mohm, not included in the quantitations.
Cell5 parameter not recorded fully, also not included in the final analysis

TABLE 14

Resting membrane potentials, membrane input resistances and membrane capacities of MEF-derived 5F-iN cells on Day 12.

| Cell 1 | −30 | 0.42 | 25 |
|---|---|---|---|
| Cell 2 | −57 | 0.45 | 42 |
| Cell 3 | −65 | 0.38 | 32 |
| Cell 4 | −60 | 0.74 | 53 |
| Cell 5 | −46 | 0.86 | 22 |
| Cell 6 | −35 | 0.89 | 27 |
| Cell 7 | −27 | 1.10 | 25 |
| Cell 8 | | 1.10 | 19 |
| Cell 9 | | 0.95 | 21 |
| Cell 10 | | 0.62 | 19 |
| Cell 11 | −49 | 0.59 | 22 |
| Cell 12 | −65 | 0.13 | 26 |
| Cell 13 | −45 | 0.49 | 34 |
| Cell 14 | −47 | 0.49 | 53 |
| Cell 15 | −45 | 0.56 | 37 |
| Cell 16 | −56 | 0.50 | 27 |
| Cell 17 | −43 | 0.62 | 32 |
| Cell 18 | −26 | 0.36 | 22 |
| Cell 19 | −50 | 0.82 | 18 |
| Cell 20 | −55 | 0.63 | 29 |
| Cell 21 | −57 | 0.74 | 21 |

Rmp: resting membrane potential;
Rm: membrane input resistance;
Cm: membrane capacitance.
Note
that in some cases, different internal solutions were used, which did not allow for the measurement of RMP.

TABLE 15

Resting membrane potentials, membrane input resistances and membrane capacities of MEF-derived 5F-iN cells on Day 20.

| | RMP (mV) | Rm (GΩ) | Cm (pF) |
|---|---|---|---|
| | MEF-derived 5F-iN cells: Day 20 | | |
| Cell 1 | | 0.90 | 45 |
| Cell 2 | | 0.48 | 40 |
| Cell 3 | −49 | 0.71 | 17 |
| Cell 4 | −64 | 0.50 | 39 |
| Cell 5 | −60 | 0.25 | 103 |
| Cell 6 | −30 | 0.74 | 22 |

TABLE 15-continued

Resting membrane potentials, membrane input resistances and membrane capacities of MEF-derived 5F-iN cells on Day 20.

| | RMP (mV) | Rm (GΩ) | Cm (pF) |
|---|---|---|---|
| | MEF-derived 5F-iN cells: Day 20 | | |
| Cell 7 | −47 | 0.19 | 65 |
| Cell 8 | −61 | 0.24 | 87 |
| Cell 9 | −57 | 0.32 | 45 |
| Cell 10 | −52 | 0.67 | 30 |
| Cell 11 | −68 | 0.90 | 28 |
| Cell 12 | −56 | 0.65 | 24 |
| Cell 13 | −52 | 0.96 | 20 |
| Cell 14 | −69 | 0.26 | 58 |

Rmp: resting membrane potential;
Rm: membrane input resistance;
Cm: membrane capacitance.
Note
that in some cases, different internal solutions were used, which did not allow for the measurement of RMP.

TABLE 16

Resting membrane potentials, membrane input resistances and membrane capacities of TTF-derived 5F-iN cells on Day 12.
TTF-derived 5F-iNs cells: Day 12

| Cell 1 | −62 | 0.27 | 22 |
|---|---|---|---|
| Cell 2 | −69 | 0.24 | 32 |
| Cell 3 | −55 | 0.42 | 35 |
| Cell 4 | −40 | 0.00 | 20 |
| Cell 5 | −35 | 0.21 | 29 |
| Cell 6 | −70 | 0.39 | 23 |
| Cell 7 | −62 | 0.16 | 27 |
| Cell 8 | −48 | 0.14 | 21 |
| Cell 9 | −64 | 0.24 | 26 |
| Cell 10 | −64 | 0.49 | 27 |
| Cell 11 | −60 | 0.31 | 25 |

Rmp: resting membrane potential;
Rm: membrane input resistance;
Cm: membrane capacitance.
Note
that in some cases, different internal solutions were used, which did not allow for the measurement of RMP.

TABLE 17

Resting membrane potentials, membrane input resistances and membrane capacities of MEF-derived Ascl1-iN cells on Day 12.
MEF-derived Ascl1-iN cells: Day 12

| Cell 1 | −50 | 0.70 | 21 |
|---|---|---|---|
| Cell 2 | −45 | 0.60 | 23 |
| Cell 3 | −55 | 0.56 | 15 |
| Cell 4 | −55 | 0.49 | 21 |
| Cell 5 | −43 | 1.20 | 23 |
| Cell 6 | −30 | 2.00 | 22 |
| Cell 7 | −60 | 0.45 | 17 |
| Cell 8 | −54 | 1.20 | 13 |
| Cell 9 | −67 | 1.20 | 18 |
| Cell 10 | −43 | 1.20 | 13 |
| Cell 11 | −33 | 0.86 | 19 |

Rmp: resting membrane potential;
Rm: membrane input resistance;
Cm: membrane capacitance.
Note
that in some cases, different internal solutions were used, which did not allow for the measurement of RMP.

TABLE 18

Resting membrane potentials, membrane input resistances and membrane capacities of MEF-derived Ascl1 + Brn2-iN cells on Day 12.

| | RMP (mV) | Rm (GΩ) | Cm (pF) |
|---|---|---|---|
| MEF-derived Ascl1 + Brn2-iN cells: Day 12 | | | |
| Cell 1 | −58 | 1.20 | 9 |
| Cell 2 | −35 | 3.30 | 17 |
| Cell 3 | −43 | 1.80 | 21 |
| Cell 4 | −48 | 0.42 | 15 |
| Cell 5 | −55 | 0.95 | 23 |
| Cell 6 | −40 | 0 43 | 23 |
| Cell 7 | −50 | 1.20 | 21 |
| Cell 8 | −48 | 1.60 | 12 |
| Cell 9 | −49 | 0.96 | 20 |
| Cell 10 | −49 | 0.90 | 32 |
| Cell 11 | −48 | 1.80 | 19 |
| Cell 12 | −45 | 1.20 | 25 |

Rmp: resting membrane potential;
Rm: membrane input resistance;
Cm: membrane capacitance.
Note
that in some cases, different internal solutions were used, which did not allow for the measurement of RMP.

TABLE 19

Resting membrane potentials, membrane input resistances and membrane capacities of MEF-derived Ascl1 + Myt1l-iN cells on Day 12.
MEF-derived Ascl1 + Myt1l-iN cells: Day 12

| Cell 1 | −49 | 0.63 | 15 |
|---|---|---|---|
| Cell 2 | −59 | 0.47 | 21 |
| Cell 3 | −62 | 0.85 | 22 |
| Cell 4 | −57 | 0.34 | 21 |
| Cell 5 | −40 | 1.30 | 11 |
| Cell 6 | −65 | 0.73 | 24 |
| Cell 7 | −54 | 0.63 | 13 |
| Cell 8 | −64 | 0.34 | 30 |
| Cell 9 | −41 | 0.53 | 25 |
| Cell 10 | −43 | 0.55 | 21 |
| Cell 11 | −47 | 1.10 | 18 |
| Cell 12 | −54 | 0.23 | 35 |

Rmp: resting membrane potential;
Rm: membrane input resistance;
Cm: membrane capacitance.
Note
that in some cases, different internal solutions were used, which did not allow for the measurement of RMP.

TABLE 20

Resting membrane potentials, membrane input resistances and membrane capacities of MEF-derived Ascl1 + Brn2 + Myt1l-iN cells on Day 12.
MEF-derived Ascl1 + Brn2 + Myt1l-iN cells: Day 12

| Cell 1 | −42 | 1.10 | 18 |
|---|---|---|---|
| Cell 2 | −60 | 0.62 | 20 |
| Cell 3 | −52 | 0.36 | 46 |
| Cell 4 | −61 | 1.40 | 21 |
| Cell 5 | −64 | 1.20 | 32 |
| Cell 6 | −66 | 1.10 | 30 |
| Cell 7 | −57 | 0.73 | 49 |
| Cell 8 | −59 | 0.51 | 31 |
| Cell 9 | −50 | 1.10 | 19 |
| Cell 10 | −42 | 1.00 | 36 |
| Cell 11 | −45 | 1.00 | 16 |
| Cell 12 | −40 | 0.96 | 25 |
| Cell 13 | −43 | 1.40 | 21 |

Rmp: resting membrane potential;
Rm: membrane input resistance;
Cm: membrane capacitance.

Neuronal Conversion is Rapid and Efficient.

Figure 3:
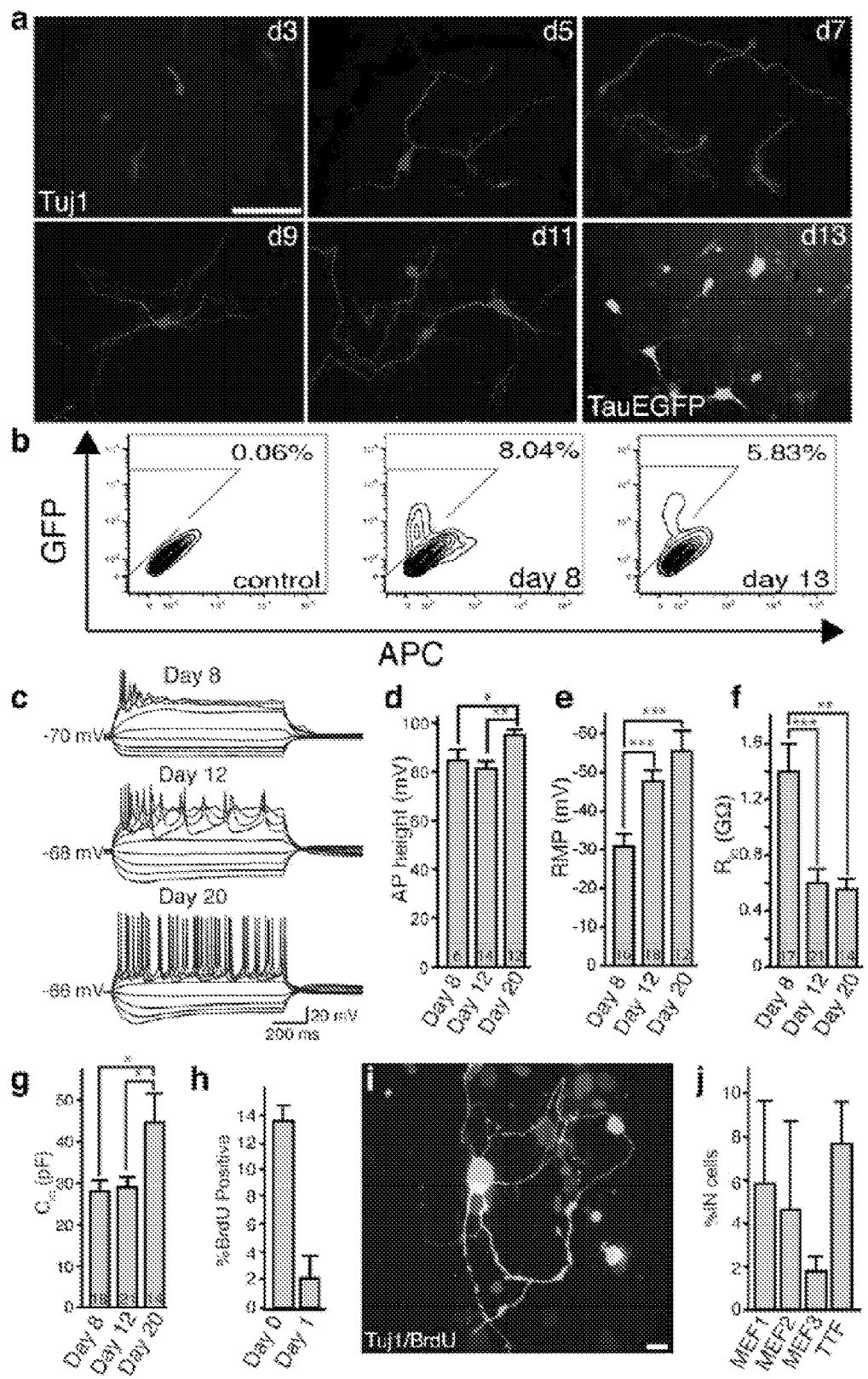
FIG. 3. The 5F pool-induced conversion is rapid and efficient. a, Tuj1-positive iN cells (red) exhibit morphological maturation over time after viral infections. At day 13, TauEGFP expression outlines neuronal processes. b, FACS analysis of TauEGFP expression 8 and 13 days post infection. Control=Uninfected TauEGFP MEFs. c, Representative traces showing action potentials elicited from MEF-iN cells at days 8, 12, and 20 post infection. Cells were maintained at a potential of ~−65 to −70 mV. Step current injection protocols were used from −50 to +70 pA. Scale bars apply to all traces. d-g, Quantification of membrane properties in MEF-iN cells at 8, 12, and 20 days post infection. Numbers in the bars represent the numbers of recorded cells. Data are presented as mean±S.E.M. * $p<0.05$;  $p<0.01$; * $p<0.001$ (Student's t-test). AP: Action Potentials; RMP: Resting Membrane Potentials; Rin: Membrane input resistances; Cm: Membrane Capacitance. AP heights were measured from the baseline. h, BrdU-positive iN cells following BrdU treatment from day 0-13 or day 1-13 after transgene induction. i, Example of a Tuj1 (green) positive cell not labeled with BrdU (red) when added at day 0 after addition of doxycycline. Data are presented as mean±S.D. j, Efficiency estimates for iN cell generation 13 days after infection (see methods). Every bar represents an independent experiment. Doxycycline was added to 48 hours after plating in MEF experiment #1 and after 24 hours in MEF experiments #2, #3. Error bars=±1 S.D. of cell counts. Scale Bars=10 μm (j), 100 μm (a).

Next, we assessed the kinetics and efficiency of 5F-induced neuronal conversion. In MEFs, Tuj1-positive cells with immature neuron-like morphology were found as early as three days after infection (FIG. 3a). After five days, neuronal cells with long, branching processes were readily detected, and over time increasingly complex morphologies were evident, suggesting an active process of maturation in newly formed iN cells (FIG. 3a). Similarly, we detected TauEGFP expression as early as day five (FIG. 8h) The fraction of TauEGFP-positive cells remained similar at eight and thirteen days post-infection, as determined by FACS analysis suggesting no de-novo generation of iN cells after day 8 (FIG. 3b). Electrophysiological parameters such as action potential height, resting membrane potential, membrane input resistance, and membrane capacitance also showed signs of maturation over time (FIG. 3c-g, Tables 2-20).

To estimate the conversion efficiency, we first determined how many of the MEF-derived iN cells divided after induction of the viral transgenes by treating the cells with BrdU throughout the duration of the culture period and beginning one day after gene induction. The results showed that the vast majority of iN cells became postmitotic by 24 hours after transgene activation (FIG. 3h-i). This allowed us to roughly estimate the conversion efficiency of our method by quantifying the total number of Tuj1-positive iN cells in the entire dish on day twelve, and dividing this number by the number of plated cells (see methods). Using this method, the efficiency ranged from 1.8-7.7% in MEF and TTF-iN cells (FIG. 3j) presumably due to slight variations in titers of the viruses. These calculations might be an underestimation of the true conversion rate because not all cells receive the necessary complement of viral transgenes.

iN Cells form Functional Synaptic Contacts.

Figure 4:
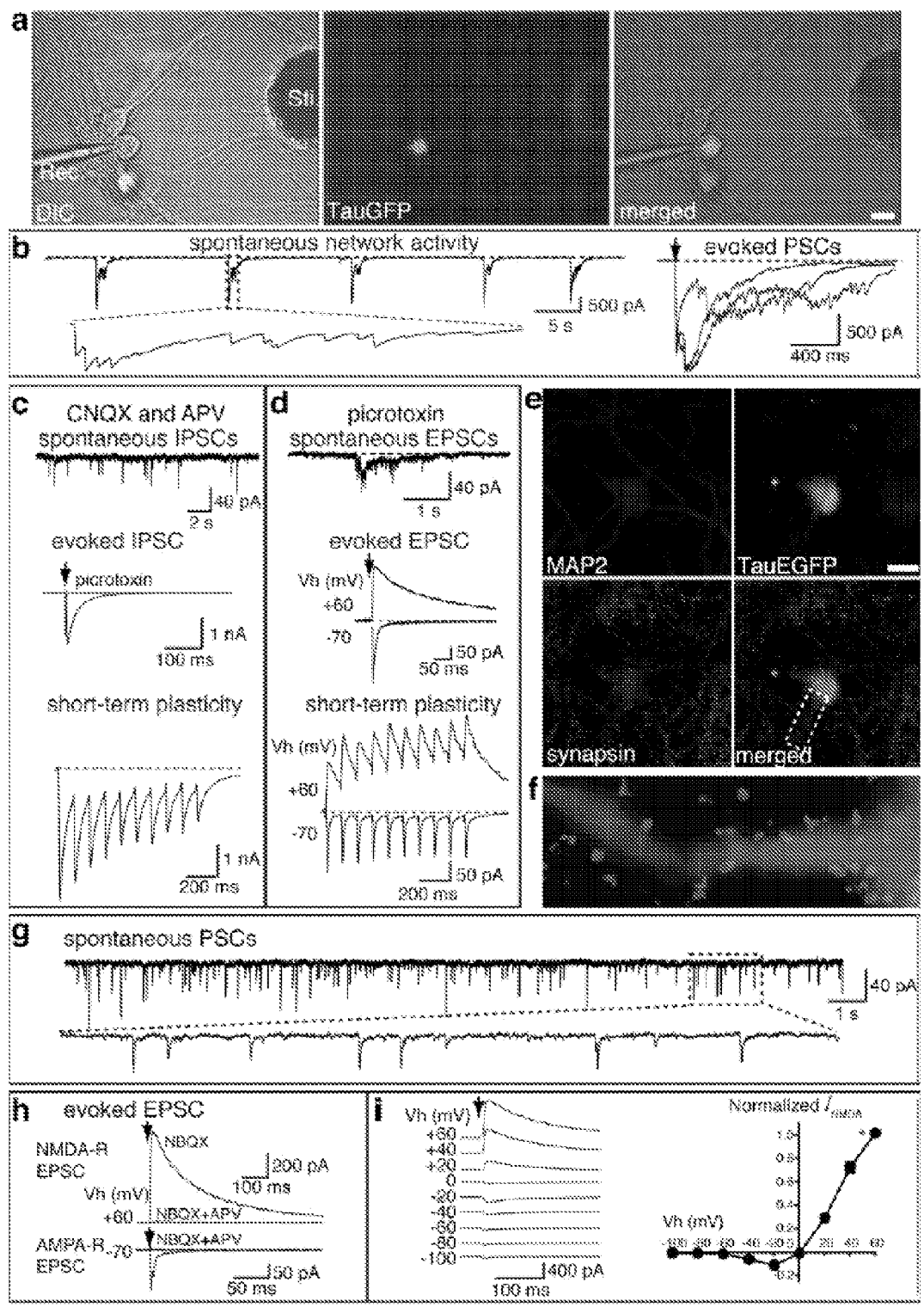
FIG. 4. MEF-derived iN cells exhibit functional synaptic properties. TauEGFP-positive iN cells were FACS purified 7-8 days post infection of MEFs and plated on cortical neuronal cultures (7 days in vitro, a-f) or on monolayer glial cultures (g-i). Electrophysiological recordings were performed 7-10 days after sorting. a, Recording electrode (Rec.) patched onto an TauEGFP-positive cell (middle panel) with a stimulation electrode (Sti.). right panel, merged picture of DIC and fluorescence images showing the recorded cell is TauEGFP positive. b, Representative traces of spontaneous synaptic network activities and representative evoked postsynaptic currents (PSCs) following stimulation. c, In the presence of 20 μM CNQX and 50 μM D-APV, upper panel shows a representative trace of spontaneous IPSCs. Evoked IPSC could be elicited (middle panel) and blocked by the addition of picrotoxin. When a train of 10 stimulations was applied at 10 Hz, evoked IPSCs exhibit depression (lower panel). d, In the presence of 30 μM picrotoxin, excitatory synaptic activities from EGFP-positive cells were observed. Spontaneous-(upper panel), and evoked-(middle panel) EPSCs. At a holding potential of −70 mV, AMPA receptor (R)-mediated EPSCs were monitored. When holding potential were set at +60 mV, both AMPA R- and NMDA R-mediated EPSCs could be recorded. Lower panel shows the short-term synaptic plasticity of both AMPA R- and NMDA R-mediated synaptic activities. e, Example of a TauEGFP-positive iN cell expressing MAP2 among cortical neurons. f, High magnification of area marked with dotted lines in e.g, Representative spontaneous postsynaptic currents (PSCs) recorded from MEF-iN cells co-cultured with glia. h, Representative traces of evoked EPSCs. NMDA-R-mediated EPSCs in the presence of 10 μM NBQX were recorded at holding potential (Vh) of +60 mV. Application of D-APV blocked the response. AMPA-R-mediated EPSCs were recorded at Vh of −70 mV. AMPA-R-evoked response is blocked by NBQX and APV. i, Current-voltage (I-V) relationship of NMDA-R-mediated EPSCs, left panel; representative traces of evoked EPSCs at different Vh as indicated. Right panel shows the summarized I-V relationship. NMDA-R EPSC amplitudes (INMDA) are normalized to EPSCs at Vh of +60 mV (indicated by *, n=5). NMDA-R EPSCs show ratifications at negative holding potentials, presumably because of the blockade of NMDA-R by $Mg^{2+}$. Scale bars=10 μm (a,d).

Since iN cells exhibit the membrane properties of neurons, we next wanted to assess whether iN cells have the capacity to form functional synapses. To accomplish this we used two independent methods. First, we determined whether iN cells were capable of synaptically integrating into preexisting neural networks. We employed FACS to purify TauEGFP-positive iN cells seven days after infection and re-plated the 5F-iN cells onto neonatal cortical neurons that had been cultured for seven days in vitro. One week after re-plating, we performed patch-clamp recordings from TauEGFP-positive iN cells and observed spontaneous and rhythmic network activity typical of cortical neurons in culture (FIG. 4a-b). Both excitatory and inhibitory postsynaptic currents (EPSCs and IPSCs) could be evoked following electrical stimulation delivered from a concentric electrode placed 100-150 μm away from the patched iN cells, (FIG. 4b-d). In the presence of the AMPA and NMDA receptor channel blockers CNQX and D-APV, spontaneous IPSCs were reliably detected (FIG. 4c, upper panel). Evoked IPSCs could be blocked by further addition of picrotoxin (FIG. 4c, middle panel). Similarly, at a holding potential of −70 mV and in the presence of picrotoxin, fast-decaying EPSCs mediated by AMPA-receptors could be evoced (FIG. 4d, middle panel). Conversely, at a holding potential of +60 mV (which relieves the voltage-dependent blockade of $Mg^{2+}$ to NMDA-receptors), slow-decaying NMDA-receptor mediated EPSCs could be recorded (FIG. 4d, middle panel).

Moreover, synaptic responses recorded from iN cells showed signs of short-term synaptic plasticity, such as depression of IPSCs and facilitation of EPSCs during a high frequency stimulus train (FIG. 4c-d, lower panels). The presence of synaptic contacts between iN cells and cortical neurons was independently corroborated by the immunocytochemical detection of synapsin-positive puncta surrounding MAP2-positive dendrites originating from EGFP-positive cells (FIG. 4e-f). We were also able to observe synaptic responses in similar experiments performed with iN cells derived from TTFs, (FIG. 9). These data demonstrate that iN cells can form functional postsynaptic compartments and receive synaptic inputs from cortical neurons.

Next we asked whether iN cells were capable of forming synapses with each other.

To address this question we plated FACS-sorted TauEGFP-positive, MEF-derived 5F-iN cells eight days after infection onto a monolayer culture of primary astrocytes, which are thought to play an essential role in synaptogenesis (Christopherson, K. S. et al. (2005) Cell 120, 421-33; Wu, H. et al. (2007) Proc Natl Acad Sci USA 104, 13821-6). Importantly, we confirmed that these cultures were free of preexisting Tuj1 or MAP2-positive neurons. Patch clamp recordings at 12-17 days after sorting indicated the presence of spontaneous post synaptic currents in (5/11 cells) (FIG. 4g). Upon extracellular stimulation, evoked EPSCs could be elicited in a majority of the cells (9/11 cells, FIG. 4h). Similar to iN cells cultured with primary cortical neurons, we were able to record both NMDA receptor mediated (9/11 cells) and AMPA receptor-mediated EPSCs (8/11 cells; FIG. 4h-i). Interestingly, we were unable to detect obvious IPSCs in a total of fifteen recorded 5F-iN cells. These data indicate that iN cells are capable of forming functional synapses with each other, and that the majority of iN cells exhibit an excitatory phenotype.

Optimal Factor Combination for Neuronal Conversion.

Figure 5:
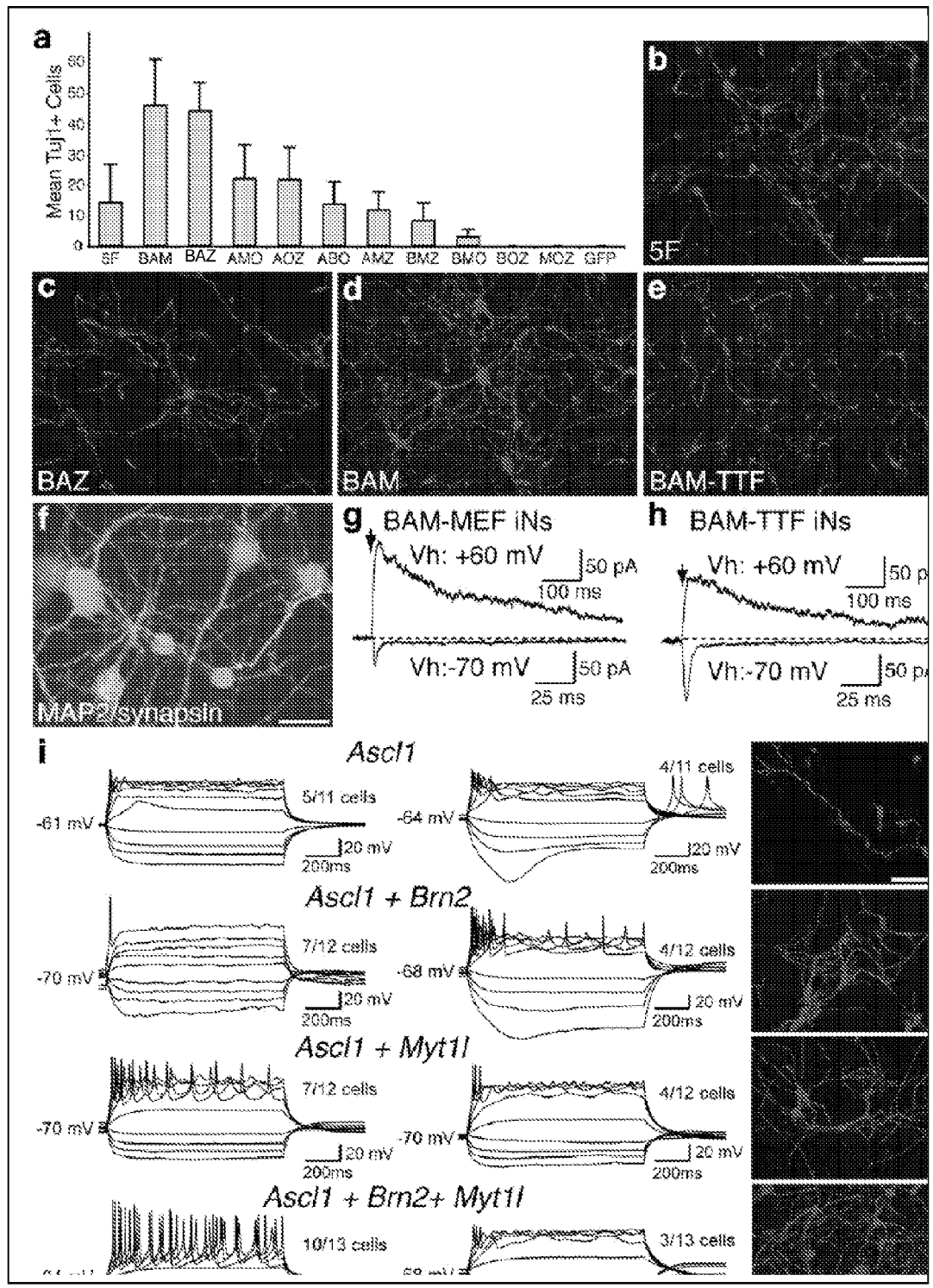
FIG. 5. Defining a minimal pool for efficient induction of functional iN cells. a, Quantification of Tuj1-positive iN cells from TauEGFP MEFs infected with different 3-factor combinations of the five genes. Each gene is represented by the first letter in its name. Averages from 30 randomly selected visual fields are shown (error bars=±S.D.) b-d, Representative images of Tuj1 staining of MEFs infected with the 5F (b), Ascl1+Brn2+Zic1 (ABZ) (c) and Ascl1+Brn2+Myt1L (BAM) (d) pools. e, Tuj1 staining of perinatal TTF-iN cells 13 days after infection with the BAM pool. f, BAM-induced MEF-iN cells express MAP2 (green) and synapsin (red) 22 days after infection. g, Representative traces of synaptic responses recorded from MEF-derived BAM (3F)-iN cells co-cultured with glia after isolation by FACs. Vh: holding potential. At Vh of −70 mV, AMPA R-mediated EPSCs were recorded; at Vh of +60 mV, NMDA R-mediated EPSCs were revealed. h, Synaptic responses recorded from TTF-derived 3F-iN cells. Scale bars in (h) apply to traces in (g). i, Representative traces of action potentials elicited from MEF-derived iN cells transduced with the indicated gene combinations, recorded 12 days after infection. Cells were maintained at a resting membrane potential of ~65 to −70 mV. Step current injection protocols were used from −50 to +70 pA. Traces in each subgroup (left or right panels) represent subpopulations of neurons with similar responses. Numbers indicate the fraction of cells from each group that were qualitatively similar to the traces shown. Right panels: representative images of Tuj1 staining after recordings from each condition. Scale bars=20 μm (f) and 100 μm (b,i).
Figure 11:
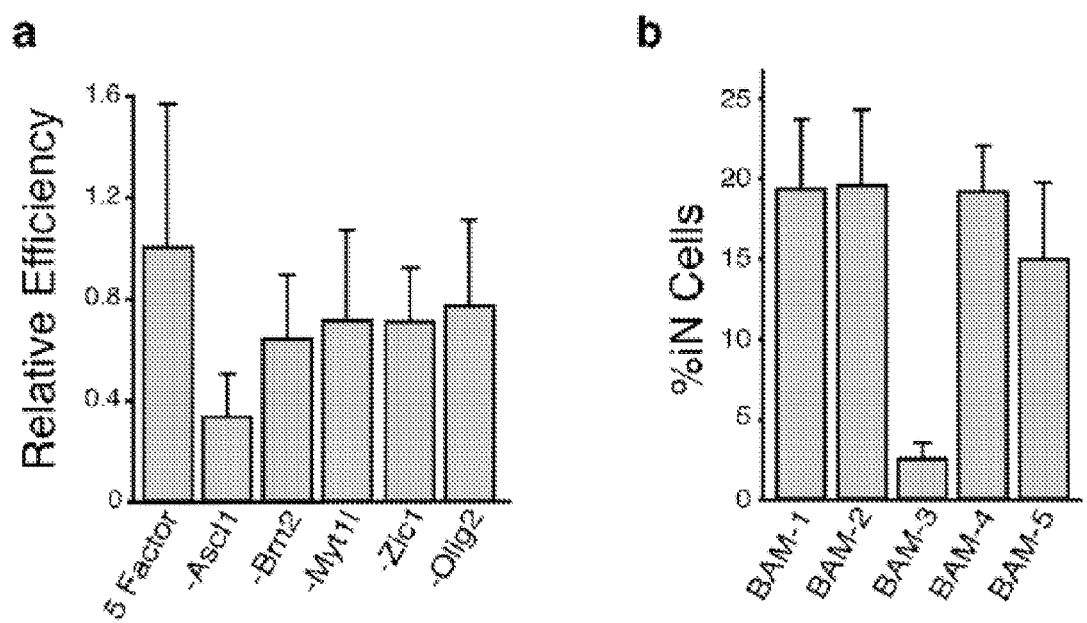
FIG. 11. Additional neuronal induction efficiency estimates. a, Effect of removing single genes from the 5F pool. The average number of Tuj1-positive neuronal cells visible in a 20× field is normalized to the 5F condition. b, Reproducibility of BAM-iN cell generation. Each bar represents an independent experiment. % iN cells is calculated from the number of plated cells (see methods). The low efficiency in BAM-3 is likely due to suboptimal lentiviral titer, however, the iN cells that are present in this condition still exhibit mature neuronal morphologies. Error bar=S.D.
Figure 12:
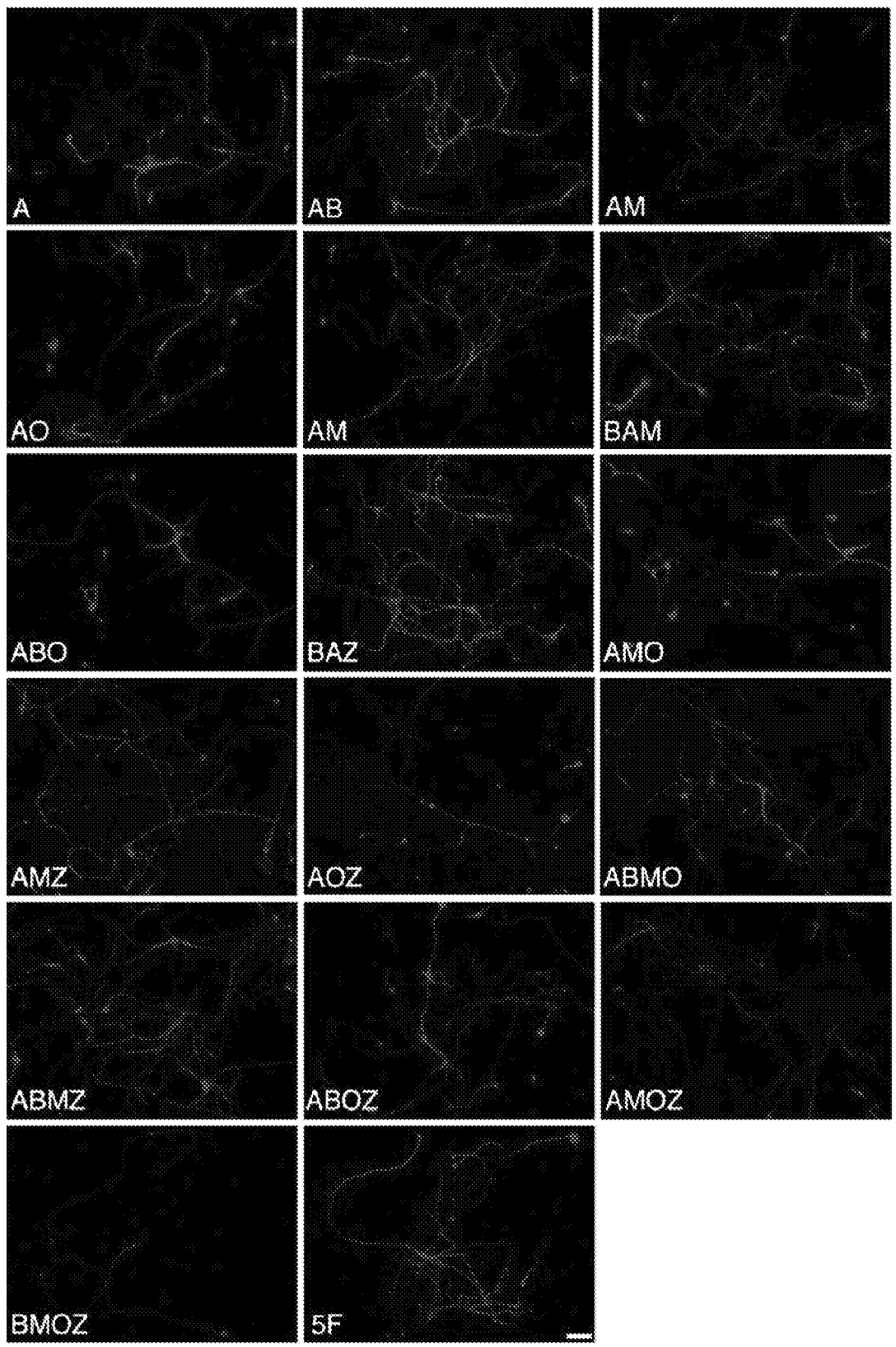
FIG. 12. Representative images from 1 to 5 factor infections. Tuj1 stainings of iN cells induced by the indicated 1 to 5 factor combinations of the genes Ascl1 (A), Brn2 (B), Myt1L (M), Olig2 (O) and Zic1 (Z) 12 days after infection. Total virus is kept constant between different factor combinations. Scale bar=50 µm.

As stated earlier, Ascl1 was the only gene from the 5F pool that was sufficient to induce neuron-like cells in MEFs. We next attempted to determine the relative contribution of each of the five genes by removing each gene from the pool and assessing the efficiency of iN cell generation. Surprisingly, only the omission of Ascl1 had a dramatic effect on induction efficiency (FIG. 11a). Thus, we tested the effects of removing two genes at a time by evaluating all possible three gene combinations. Our results indicated that either Ascl1 or both Brn2 and Myt1I must be present in order to generate iN cells (FIG. 5a). The most efficient conversions were achieved when Ascl1 and Brn2 were combined with either Myt1I (BAM pool) or Zic1 (BAZ pool). The efficiencies in these conditions were two to threefold higher than the 5F pool when the total amount of virus was kept constant (FIG. 5a-d). In this experiment the BAM-iN cells appeared to have a more complex morphology than the BAZ cells (FIG. 5c-d, FIG. 12). Therefore, we focused our further analysis on the BAM pool.

Figure 13:
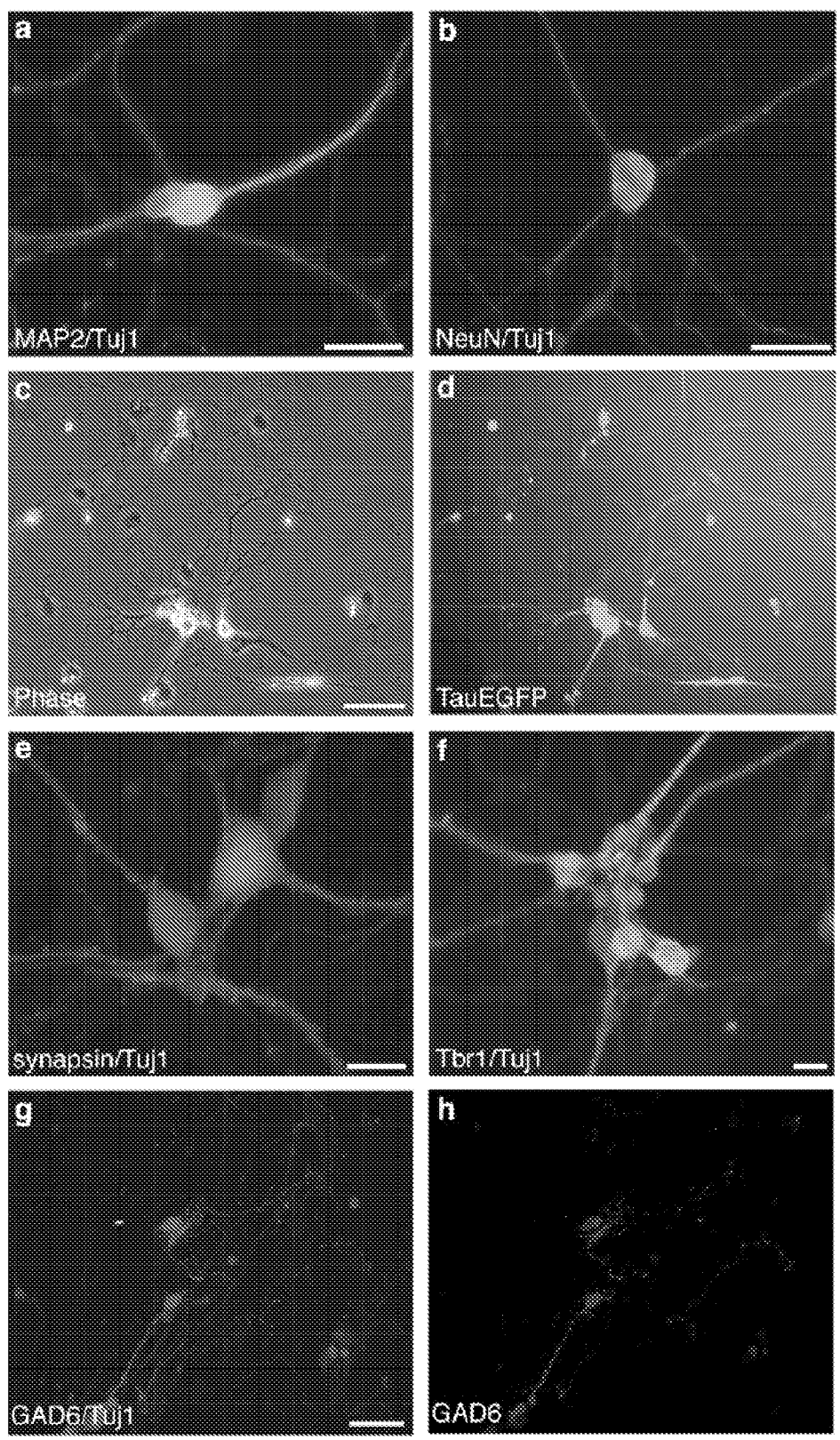
FIG. 13. Additional characterization of BAM-iN cells. a-b, Day 12 TTF-derived BAM iN cells express the pan-neuronal markers MAP2 (a, red) and NeuN (b, red) c-d, Day 21 TTF-derived BAM iN cells exhibit mature neuronal morphologies and express TauEGFP. e, Day 21 TTF-derived BAM-iN cells exhibit punctate synapsin staining. f, MEF-derived BAM iN cells express Tbr1, a marker of cortical neurons 22 days after infection. g-h, A MEF-derived BAM-iN cell expressing GAD6 (g, red, h) and Tuj1 (g, green). Scale bars=20 µm (a,b), 50 µm (c,g), 10 µm (e,f).
Figure 14:
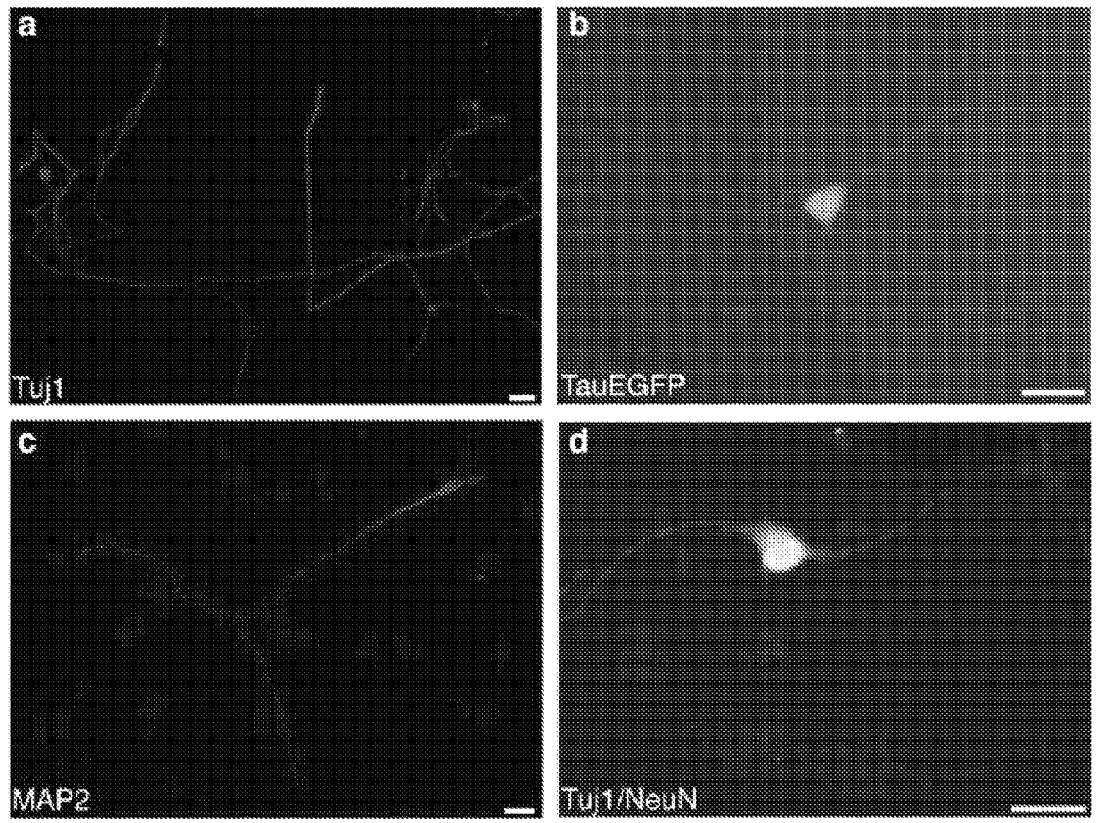
FIG. 14. BAM-iN cells derived from adult TTF. BAM iN cells derived from TTF isolated from a six-week-old TauEGFP mouse express Tuj1 (a, d, green), TauEGFP (b), MAP2 (c) and NeuN (d, red). Scale bars=20 µm (a-d).

MEF-derived BAM-iN cells expressed the pan-neuronal markers MAP2 and synapsin (FIG. 5f). The BAM-pool was capable of efficiently generating iN cells from perinatal tail tip fibroblasts (FIG. 5e, FIG. 13a-e). After infecting tail tip fibroblasts from adult mice with these three factors, we could detect neuronal cells expressing TauEGFP, Tuj1, NeuN and MAP2 (FIG. 14). Importantly, when co-cultured with astrocytes, both MEF and perinatal tail-tip fibroblast-derived BAM-iN cells were capable of forming functional synapses as determined by the presence of both NMDA- and AMPA-receptor mediated EPSCs (FIG. 5g-h). Similar to 5F-iN cells, no IPSCs were detected in MEF-derived (n=16) or tail-derived (n=12) BAM-iN cells. This functional evidence suggests that a majority of BAM-iN cells are excitatory. Indeed, 53% (111/211 cells) of MEF BAM-iN cells expressed Tbr1, a marker of excitatory cortical neurons, whereas less than 1% (3/~500 cells) were GAD-positive (FIG. 13f).

Our results left open the possibility that one or two factors might be able to induce functional neuronal properties in MEFs. Thus, we tested smaller subsets of the BAM pool to determine their functionality. In many Ascl1-induced cells, current injection elicited action potentials, but their properties appeared to be immature, consistent with their simple neurite morphology (FIG. 5i, FIG. 7b). MEFs infected with Ascl1 and Brn2 or Myt1I generated more mature action potentials and displayed more complex neuronal morphologies. In contrast, the majority of BAM-iN cells exhibited repetitive action potentials with more mature characteristics, and displayed the most complex neuronal morphologies. Thus, it appears likely that Ascl1 alone is sufficient to induce some neuronal traits, such as expression of functional voltage-dependent channel proteins that are necessary for the generation of APs, but that co-infection of additional factors will facilitate neuronal conversion and maturation.

DISCUSSION

Here we show that expression of three transcription factors can rapidly and efficiently convert mouse fibroblasts into functional neurons (iN cells). While the single factor Ascl1 was sufficient to induce immature neuronal features, the additional expression of Brn2 and Myt1I generated mature iN cells with efficiencies of up to 19.5% (FIG. 11b). Three factor iN cells displayed functional neuronal properties such as the generation of trains of action potentials and synapse formation. These transcription factors were identified from a total of nineteen candidates that we selected because of their specific expression in neural cell types or their roles in reprogramming to pluripotency (see methods)

Despite the heterogeneity of embryonic and tail-tip fibroblast cultures, the highly efficient nature of this process effectively rules out the possibility that directed differentiation of rare stem or precursor cells with neurogenic potential can explain our observations.

High expression levels of strong neural cell-fate determining transcription factors can activate salient features of the neuronal transcriptional program. Auto-regulatory feed-back and feed-forward activation of downstream transcriptional regulators may then reinforce the expression of important cell fate determining genes and help to further stabilize the induced transcriptional program. Robust changes in transcriptional activity could also lead to genome-wide adjustments of repressive and active epigenetic features such as DNA methylation, histone modifications, and changes of chromatin remodeling complexes that further stabilize the new transcriptional network (Zhou, Q. & Melton, D. A. (2008) Cell Stem Cell 3, 382-8; Jaenisch, R. & Young, R. (2008) Cell 132, 567-82). It is possible that certain subpopulations of cells are "primed" to respond to these factors, depending on their preexisting transcriptional or epigenetic states (Yamanaka, S. (2009) Nature 460, 49-52).

iN cells represent an alternative to generate patient-specific neurons. The generation of iN cells is fast, efficient, and devoid of pluripotent stem cells. Therefore, iN cells provide a novel and powerful reagent for studying cellular identity and plasticity, modeling neurological disease, discovering novel drugs, and developing novel regenerative medicine-based therapies.

Example 2

Induced Oligodendrocyte Production 10 candidate genes were screened for oligodendrocytes induction: Ascl1; NRx6-1 Myt1; Zfp536; NRx2-2; Olig2; Olig1; Sox10; NRx6-2; MRF. EGFP was induced as an aid to visualization. All ten transcription factors, all of which are known to play a role in oligodendrocyte specification or differentiation, were screened in wild-type mouse embryonic fibroblasts (MEFs). Strikingly, when all ten genes were combined, we observed cells with characteristic oligodendrocyte morphology after 12 days of transgene expression. These cells also expressed the oligodendrocyte specific surface marker O4, which marks terminally differentiating OPCs and. In parallel, we examined the effect of removing groups of genes from this initial pool of ten, and we were able to derive oligodendrocytes from some pools of six genes. These data indicate that combination(s) of the ten transcription factors can induce oligodendrocyte-like cells from embryonic fibroblast cultures.

Example 3

Neural Progenitor Cell Induction

Six factors were tested for induction of neural progenitor cells: Sox2, Lhx2, FoxG1, Id4, Rfx4, and Zic1. Colonies form after infection with a combination of the 6 NSC reprogramming factors showing a morphology similar to a neurosphere, as it would appear after expansion of brain-derived neural stem cells. A large fraction of the cells in that colony express endogenous Sox2 as judged from EGFP fluorescence originating from the Sox2:EGFP allele knocked into the Sox2 locus. About 3 weeks after infection with the NSCR factors a large number of neural stem cell marker genes are induced.

Example 4

Induction of Neural Cells from Hepatocytes

Hepatocytes are the principal cell type in the liver accounting for ~70% of the mass of the adult organ. Expression profiling suggests that hepatocytes are a relatively homogeneous cell population despite functional differences depending on histoanatomical location. First, we evaluated whether iN cells can be derived from primary liver cells. To that end, we established cell cultures of livers from postnatal days 2-5 wild-type mice and TauEGFP knock-in mice which express EGFP under the control of a promoter specific for neurons. Four days after isolation the hepatic cultures showed a typical epithelial morphology and expressed hepatocyte markers such as albumin, α-fetoprotein and α-anti-trypsin. One week post explant a typical culture was composed of 50-70% albumin-positive hepatocytes, 16% myeloid cells (MAC-1 positive), 2% Kupffer cells (F4/80 positive) and 2% endothelial cells (platelet/endothelial cell adhesion molecule 1 PECAM1-positive). The remaining cells that eluded our characterization presumably represent immature hepatocytes, bile duct cells, various epithelial progenitor cells, more immature hematopoietic cells, pericytes and liver fibroblasts. Absence of neuronal or neural progenitor cell markers such as Sox2, Brn2, MAP2, and NeuN in the culture was confirmed by immunofluorescence. The rare (≤1/5000) Tuj1-positive cells were always characterized by round and flat morphology. EGFP signal from TauEGFP reporter was not detectable at any time in the culture by flow cytometry and fluorescence microscopy.

After one passage, the hepatocyte cultures were infected with doxycycline (dox)-inducible lentiviruses containing the cDNAs of Ascl1 (A), Brn2 (B) and Myt1I (M) in all possible combinations (A, B, M, AB, AM, BM and BAM). To induce the transgenes, dox was added to the media one day after infection. Hepatocyte culture media was changed to a basic neuronal media (N3) in the presence of dox after another two days. Thirteen days after dox induction, TauEGFPpositive cells with a complex neuronal morphology were readily detected in the wells that received all three factors (BAM); all other factor combinations produced practically no neuronal cells. Thus, in contrast to fibroblasts, liver cells require all three factors to induce neuronal morphologies. Immunofluorescence confirmed that all TauEGFP-positive cells generated by the BAM factors were also Tuj1-positive, i.e. expressed neuronal microtubules.

Three weeks after dox induction, the cells expressed the additional pan-neuronal markers PSA-NCAM, NeuN, MAP2, and synapsin, similar to our previously reported fibroblast iN cells. A fraction (35/200 Tuj1-positive cells) of the cells also expressed vesicular glutamate transporter 1 (vGLUT1). In contrast, no GAD67-positive cells were detected (0/200 Tuj1-positive cells). To further characterize liver-derived iN cells we purified TauEGFP-positive iN cells from liver preparations by fluorescence activated cell sorting (FACS) 21 days after dox induction. We then extracted total RNA from both sorted cells and uninfected liver cultures and performed quantitative PCR expression analysis. In TauEGFP-positive population all transcripts characterizing the starting cell population (albumin, MAC-1, F4/80 and PECAM-1) were significantly down regulated, whereas neuronal transcripts such as Tuj1, synapsin, vGLUT1 were up regulated. No GAD67 transcripts were detectable in EGFP-sorted cells. This indicates that—similar to fibroblasts iN cells—the majority of mature liver-derived iN cells are excitatory and only few if any are inhibitory.

To unambiguously identify hepatocytes from primary liver cultures we employed a Cre-LoxP lineage tracing system. We used transgenic mice expressing Cre recombinase under the control of the albumin promoter and enhancer (Albumin-Cre). Importantly, this allele has been characterized extensively and shown to be specific to hepatocytes in both fetal and adult mice. Albumin-Cre mice were crossed with ROSA26-mTmG reporter mice which express membranous tdTomato before and membranous EGFP after Cre-mediated recombination. In double transgenic mice, hepatocytes are permanently labeled with EGFP whereas the non-hepatocytes express tdTomato. As expected, the EGFP fluorescence was confined to epithelial cells in freshly isolated liver cultures from these mice and cultures were composed of ~80% EGFP-positive and ~20% tdTomato-positive cells. However, this ratio declined to 60% EGFP-/40% tdTomato-positive cells after one week in culture, implying that hepatocytes were lost and/or other cells outgrew the hepatocytes.

Next, we derived liver-iN cells from these cultures by infecting them with the three BAM factors as described above. Thirteen days after dox induction we detected both red and green fluorescent cells with neuronal morphologies. Subsequent analysis showed that EGFP-positive cells with complex morphology also expressed the neuronal markers Tuj1 and PSA-NCAM. Similar results were obtained using an independent reporter allele (ROSA26-Bgeo) where expression of β-galactosidase is induced after Cre-mediated recombination. Fourteen days after infection Xgal staining identified numerous three-dimensional cells with long complex processes. These experiments demonstrate that iN cells can be derived from terminally differentiated hepatocytes.

To gain insight into the process of hepatocyte-derived (Hep)-iN cell generation, we evaluated the cell division frequency after induction of the BAM transgenes in liver cultures by a 5-bromodeoxyuridine (BrdU) incorporation assay. When BrdU was present from the day of infection (i.e. one day before dox) throughout the time of iN generation, 12% of the Tuj1-positive cells at day 13 incorporated BrdU. However, when BrdU treatment was begun on the day of transgene induction (dox addition) only 1% of the Tuj1-positive cells were BrdU-positive suggesting that the vast majority of hepatocytes generated iN cells without undergoing cell division.

Next, we wanted to address the reprogramming kinetics from hepatocytes to iN cells. Toward this end, we generated transgenic mice containing the TauEGFP allele together with Albumin-Cre and a ROSA26-tdTomato reporter. In this lineage tracing system albumin-positive hepatocytes and their progeny constitutively express tdTomato. We established primary hepatocyte cultures from these mice and as expected thirteen days after transduction with the BAM factors we were able to identify Tau-EGFP/tdTomato-double positive cells with neuronal morphology. The TauEGFP fluorescence allowed us to monitor neuronal gene induction in live cells during the conversion process. Cultures were analyzed by flow cytometry at days 1, 3, 7 and 13 after dox. Simultaneously, MEFs and tail tip fibroblasts (TTFs) derived from TauEGFP mice were infected as control. The EGFP-positive fraction was determined in tdTomato-positive and tdTomato-negative subpopulations. Surprisingly, as early as one day after transgene induction, a small but distinct fraction of hepatocytes expressed TauEGFP already. The frequency of EGFP-positive cells steadily increased over time with similar kinetic for hepatocytes and fibroblasts.

Given that the fraction of EGFP-positive cells is strongly influenced by survival and proliferation of non-converted cells in the neural media we estimated the actual conversion efficiency by determining the total number of TauEGFP-positive cells in the wells at the various time points. This value was then expressed as percentage of the total number of hepatocytes present at day 0 of infection. This ratio should represent a good approximation of the conversion efficiency as we had previously determined that over 99% of hepatocytes converting to iN cells do not proliferate. Taking into account that the infection rate was ≥98% in MEFs, TTFs and non-hepatocyte liver cells but only 30% in hepatocytes the efficiencies of converting hepatocytes were similar to the postnatal fibroblasts (ca. 6% after two weeks) but lower than embryonic fibroblasts (ca. 20% after two weeks).

We finally asked whether Hep-iN cells possess functional neuronal properties. To this end, we performed patch-clamp recordings on both Albumin-Cre/ROSA26-mTmG and Albumin-Cre/ROSA26-tdTomato/TauEGFP Hep-iN cells 21 days after dox induction. Hep-iN cells were identified as EGFP-positive cells in the first case and as tdTomato positive cells in the second. The average resting membrane potential of the Hep-iN cells was −55.8±2.1 mV (n=10). Moreover, spontaneous action potential firing was detected in the cells (n=10). Also, all analyzed Hep-iN cells showed action potentials when depolarized by current injections.

When whole-cell currents were recorded, fast inactivation sodium current and outward potassium currents could be revealed. These results show that Hep-iN possess the membrane properties typical of primary neurons.

In summary, we show that albumin-expressing hepatocytes can be converted into functional iN cells by the three factors Ascl1, Brn2 and Myt1l. Remarkably, the same three iN cell factors can induce neuronal cells from completely different donor cell types, as it has also been observed for iPS cell reprogramming. The neuronal conversion efficiencies and dynamics of hepatocytes were surprisingly similar to postnatal fibroblasts suggesting that the age of donor cells may have a bigger impact on reprogramming kinetics than the cell of origin. However, hepatocytes differ from fibroblasts in that combinations of fewer factors have only little effect on induction of neuronal traits. Our findings show that iN cells generation is not limited to fibroblasts and can be extended to a defined endoderm-derived cell type. This shows that potentially any cell type that can be cultured in vitro may be able to be converted into iN cells using the same factors.

Materials and Methods

Hepatocyte culture. Disaggregated mouse liver cells were isolated by an adaptation of the two step collagenase perfusion technique. Liver was extirpated 2 to 5 days after birth, incised, washed with Kreb's Ringer Buffer 0.1 mM EDTA, minced and digested in Kreb's Ringer Buffer 0.15 mM $CaCl_2$, 0.54 mg/ml of collagenase type I (Sigma C0130) 40 min at 37° C. After two wash in Kreb's Ringer Buffer primary hepatocytes were centrifuged at 100 g 3 mins and plated on Collagen coated plates in hepatocytes plating media consisting of DMEM (Invitrogen) supplemented with bovine serum albumin (2.0 g/l), glucose (2.0 g/l), galactose (2.0 g/l), ornithine (0.1 g/l), proline (0.030 g/l), nicotinamide (0.610 g/l), Znc12 (0.025 mg/l), $ZnSO_4:7H_2O$ (0.750 mg/l), $CuSO_4:5H_2O$ (0.20 mg/l), $MnSO_4$ (0.025 mg/l), glutamine (5.0 mM), insulin (5.0 mg/l), human transferring (5.0 mg/l), selenium (5.0 µg/l), dexamethasone (10-7 M), penicillin (100 mg/l), streptomycin (100 mg/l), and 10% calf serum. After 4 hrs media was changed with hepatocyte culturing media, consisting of hepatocytes plating media 0% calf serum, HGF (40 ng/ml) and EGF (20 ng/ml).

Lentivirus preparation and infection. TetO-FUW-based lentiviruses were prepared as previously described with some modification for hepatocytes. Briefly, 293T/17 cells were seeded at $5 \times 10^6$ per 100 mm plate in DMEM containing 10% Calf Serum. On the next day, 10 µg of lentiviral vectors together with 5 µg of PMDL, 2.5 µg of VSVg and 2.5 µg of RSV were introduced into 293T/17 cells using calcium-phosphate precipitation. After 16 hour, the medium was replaced with 4 ml. On the next day, virus-containing supernatant was recovered, filtered through 0.45 µm cellulose acetate filter (Whatman), and spun at 16500 rpm for 1 h at 4C. Pellet was resuspended in hepatocyte culturing media in a volume 100 times smaller than the starting supernatant and stored at −80C. Three to five days after establishing the primary culture cells were detached by trypsin and seeded on collagen-coated plates at the density of 50 k cells/$cm^2$ in hepatocyte plating media. One day after medium was changed to the hepatocyte culturing media containing 100 µl/ml of concentrate lentivirus supplemented with polybrene at the final concentration of 8 µg/ml. Doxycycline (2 mg/ml) was added 16 hrs later and media was switched to N3 48 hours later.

Immunofluorescence, RT-PCR, and flow cytometry. Neuronal cells were defined as cells that stained positive for Tuj1 and had a process at least three times longer than the cell body. For immunofluorescence staining, cells were washed with PBS and then fixed with 4% paraformaldehyde for 10 min at room temperature. Cells were then incubated in 0.2% Triton X-100 (Sigma) in PBS for 5 min at room temperature. After washing twice with PBS, cells were blocked in a solution of PBS containing 4% BSA, 1% FBS for 30 min at room temperature.

Primary and secondary antibodies were diluted in a solution of PBS containing 4% BSA and 1% FBS. Fields of cells for staining were outlined with a PAP pen (DAKO). Primary and secondary antibodies were typically applied for 1 h and 30 min, respectively. Cells were washed three times with PBS between primary and secondary staining. For anti-BrdU staining, cells were treated with 2 N HCl in PBS for 10 min and washed twice with PBS before permeabilization with Triton X-100 (Sigma). The following antibodies were used for our analysis: goat anti-albumin (Bethyl, 1:200), rat anti PECAM-1 (Becton Dickinson, 1:400) mouse anti-MAP2 (Sigma, 1:500), mouse anti-NeuN (Millipore, 1:100), rabbit anti-Tuj1 (Covance, 1:1,000), mouse anti-Tuj1 (Covance, 1:1,000), mouse anti-BrdU (Becton Dickinson, 1:50), E028 rabbit anti-synapsin (gift from T. Südhof, 1:500), guinea-pig anti-vGLUT1 (Millipore, 1:2,000), anti-mouse PSA-NCAM (DSHB, 1:20). FITC- and Cy3-conjugated secondary antibodies were obtained from Jackson Immunoresearch. Alexa-488, Alexa-555, and Alexa-350 conjugated secondary antibodies were obtained from Invitrogen.

TauEGFP-expressing cells were analysed and sorted on a FACS Aria II and flow cytometry data were analysed using FACSDiva Software (Becton Dickinson). The following antibodies were used for flow cytometry staining of the liver cells: APC conjugated rat anti MAC-1 (eBioscience) at 1:400 dilution, FITC conjugated mouse anti-F4/80 (ebioscience) at 1:100 diluition.

RNA isolation, reverse transcription and quantitative real-time PCR analysis. Total RNA was isolated using the Qiagen RNAeasy kit according to the manufacturer's instruction (Qiagen). Concentration and purity of the RNA was determined by OD260/280 reading. Two hundred nanograms of total RNA were reverse transcribed using SuperScript® First-Strand Synthesis System (Invitrogen). Resulting cDNA was diluted 1:10 and real-time polymerase chain reaction (PCR) was performed using the 7900HT Real-Time PCR System (Applied Biosystems).

Amplification reactions were carried out in a 10 μL volume using SYBR Green I dye and the following amplification conditions: 50° C. for 2 minutes and 95° C. for 10 minutes (95° C., 15 seconds; 60° C., 1 minute) for 40 cycles. Primers used are reported in Table S1. The mRNA/cDNA abundance of each gene was calculated relative to the expression of a housekeeping gene, GAPDH (glyceraldehyde-3-phosphate-dehydrogenase).

X-gal staining. Cells were washed with PBS and fixed in the plate with 1% glutaraldehyde for 5 minutes. Plates were stained with a solution containing 0.04% of X-gal/DMSO, 1 mM of MgCl2, 3 mM of K4[Fe(CN)6], and 3 mM of K3[Fe(CN)6] in PBS at 37° C. for 12 hours.

Electrophysiology. Cells were analyzed at indicated time points after dox induction. Action potentials were recorded with current-clamp whole-cell configuration. The pipette solution for current-clamp experiments contained (in mM) 123 K-gluconate, 10 KCl, 1 MgCl2, 10 HEPES, 1 EGTA, 0.1 CaCl2, 1 K2ATP, 0.2 Na4GTP and 4 glucose, pH adjusted to 7.2 with KOH. Membrane potentials were kept around −65 to −70 mV, and step currents were injected to elicit action potentials. For voltage-clamp experiments, the internal solution contained (in mM) CsCl 135, HEPES 10, EGTA 1, Mg-ATP 4, Na4GTP 0.4, and QX-314 10, pH7.4. The bath solution contained (in mM): NaCl 140, KCl 5, CaCl2 2, MgCl2 2, HEPES 10, and glucose 10, pH7.4. Whole-cell currents including Na+ and K+ currents were recorded at a holding potential of −70 mV, voltage steps ranging from −80 mV to +90 mV were delivered at 10 mV increments.

Mice. We first crossed heterozygous Albumin-Cre knock-in mice with homozygous mTmG mice (Gt(ROSA)26Sortm4(ACTB-tdTomato,-EGFP)Luo/J.) (Jackson Laboratory) or with ROSA26-Bgeo heterozygous mice. Secondly we crossed homozygous TauEGFP knock-in mice (Jackson Laboratory) with ROSA26-tdTomato homozygous mice (B6; 129S6-Gt(ROSA)26Sortm9(CAG-tdTomato)Hze/J) (Jackson Laboratory). Obtained ROSA26-tdTomato/TauEGFP heterozygous mice were then crossed with Albumin-Cre knock-in mice.

Example 5

Induction of Neuronal Cells from Human Fibroblasts

Cell lineage fates are considered stable once determined during embryonic development. However, experimental manipulations such as somatic cell nuclear transfer, cell fusion, or expression of lineage-specific factors can induce cell fate changes in diverse somatic cell types. As shown above, forced expression of a combination of three transcription factors, Brn2 (also known as Pou3f2), Ascl1, and Myt1l can rapidly and efficiently convert fibroblasts into functional neuron-like cells termed induced neuronal (iN) cells. It is shown herein that the same three factors can induce functional neurons from human pluripotent stem cells in a surprisingly rapid and efficient manner. Neuronal cells with functional properties were observed as early as 6 days after gene transduction, which is a substantial acceleration over current differentiation strategies. When combined with the basic helix-loop-helix transcription factor NeuroD1, the three factors could also convert primary human fetal fibroblasts into functional iN cells. Importantly, fibroblast-derived iN cells were able to generate repetitive action potentials and to form synaptic contacts with primary cortical neurons 4 to 5 weeks after transduction. These data demonstrate that human non-neural somatic cells as well as pluripotent stem cells can be directly converted into functional neurons by lineage-determining transcription factors, allowing robust generation of human neurons for in vitro studies and applications in regenerative medicine.

Here, we show that (i) iN cell reprogramming factors greatly enhance and accelerate the induction of functional neurons from human ES cells and (ii) that iN cells can be derived from primary human fetal fibroblasts.

Figure 15:
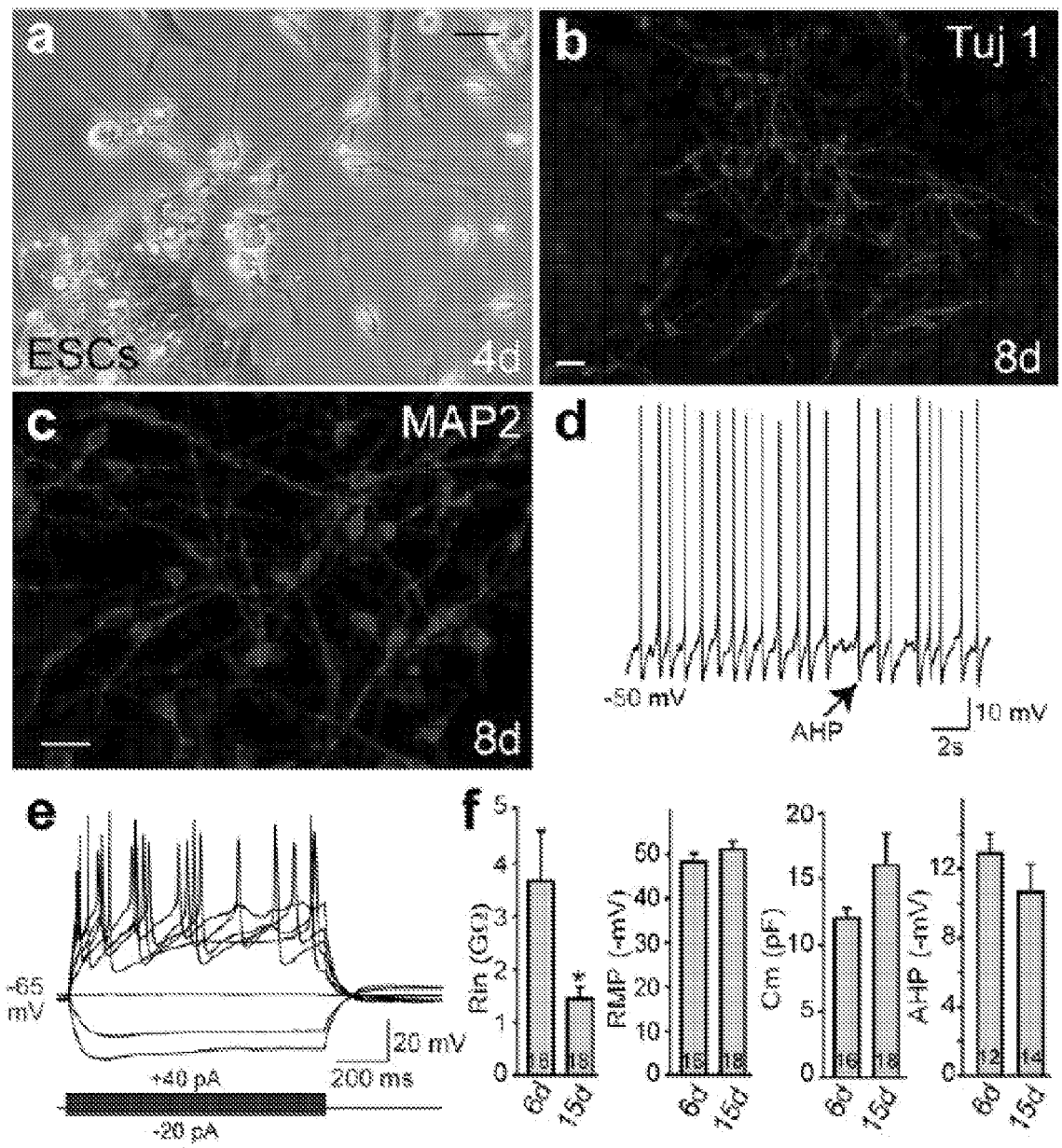
FIG. 15. Rapid generation of functional neurons from human ES cells. a, Biopolar neuronal morphologies 4 days after dox treatments and 5 days after infection of human ES cells with Brn2, Ascl1, Myt1I (BAM), and EGFP. b-c, Eight days after induction, BAM-ES cells displayed complex neuronal morphologies and expressed the pan-neuronal markers Tuj1 (b) and MAP2 (c). d, Spontaneous trains of action potentials of a human ES-iN cell six days after induction of BAM factors. Arrow indicates pronounced after hyperpolarization potential (AHP). e, Whole cell recordings from human ES-derived neuronal like cells. Representative traces of action potentials in response to step current injections 15 days after induction. Membrane potential was maintained at around −63 mV. f, Quantification of intrinsic membrane properties; membrane input resistance (Rin), resting membrane potential (RMP), capacitance (Cm), and after hyperpolarization potentials (AHP). Scale bars: 10 µm (a,b,c). * p<0.05, Student t-test.

We infected undifferentiated human ES cells (H9 line 33) with the three iN cell factors Brn2, Ascl1, and Myt1l (BAM) encoded in doxycycline (dox)-inducible lentiviral vectors in chemically-defined N3 media 34 together with an EGFP virus to help visualize the cells. One day after infection, we activated the transgenes by the addition of dox. After 24 h, the majority of ES cells were EGFP positive. To inhibit the growth of uninfected ES cells, we added 4 μM Cytosine β-D-arabinofuranoside (Ara-C) to the media 48 h after dox. Over the course of the following days the cells underwent dramatic morphological changes. Surprisingly, as early as three days after dox treatment, we observed bi- and multipolar neuron-like cells surrounding nearly all ES cell colonies (FIG. 15a). By day 8, cells with more mature neuronal morphologies that expressed β-III-tubulin (Tuj1) and MAP2 were present throughout the plate (FIG. 15b,c). Thus, forced expression of the BAM factors had induced neuronal differentiation from human ES cells in an unexpectedly rapid manner. In contrast, after infection with EGFP virus alone, no neuronal cells were generated during the same timeframe, as the majority of the ES cells had died due to Ara-C treatment.

We then performed electrophysiological recordings to evaluate the functional properties of these neuronal cells. We dissociated BAM-ES cultures 3-4 days after dox, and replated them onto a monolayer culture of primary mouse glia. After another 3-4 days (i.e. as early as 6 days after induction), neuronal cells already exhibited passive and active membrane properties resembling immature neurons. Some cells fired series of action potentials spontaneously (FIG. 15d). Upon current injection, the cells generated single or repetitive action potentials (FIG. 15e). At day 15 after induction, the average membrane potential of neuronal cells was −51 mV and the membrane capacitance was ~16 pF (FIG. 15f. Moreover, prominent after-hyperpolarization potentials (AHPs) were observed in these cells (FIG. 15d and f). Thus, the BAM factors rapidly induced cells with morphological, biochemical and functional properties of neurons from human ES cells which we termed ES-iN cells to distinguish them from ES cell-derived neurons generated using conventional differentiation protocols.

Finally, we determined whether fewer of the three factors were sufficient to induce neurons in similar efficiencies and infected human ES cells with the single factors and all the two-factor combinations. Eight days after gene induction, ES cells were fixed and stained for MAP2. We found that Ascl1 was sufficient to induce pan-neuronal markers but the addition of Brn2 or Myt1l generated more complex morphologies, however the BAM pool remained the most effective condition, consistent with our observations in mouse.

We then sought to explore whether transcription factor-mediated neuronal induction can also be applied to human somatic cells. We obtained the human fetal lung fibroblast cell line IMR90 and also derived primary human fetal fibroblasts (HFFs) from the distal portion of a lower extremity of a gestation week 9 fetus. We confirmed that the primary cultures did not contain cells with neural character by screening for a panel of neuronal, glial and neural precursor cell markers (see Methods). Seven to 10 days after infection with the BAM factors and EGFP, cells exhibiting neuronal morphologies were readily detectable, and immunofluoresence analysis performed 21 days after infection indicated the expression of the pan-neuronal marker Tuj1. However, the induction of neuronal cells appeared inefficient, and most cells exhibited immature morphologies. Electrophysiological recordings showed that in these fibroblast-BAM-iN cells only action potential-like responses could be elicited by depolarization but no mature action potentials. In contrast, cells infected with the EGFP virus alone did not induce any neuron-like morphologies up to 3 weeks post infection. Thus, the BAM factors induced some neuronal features but appeared to be insufficient to generate fully functional neurons from human fetal fibroblasts. This suggests that other factor combinations may be required for the conversion of human fibroblasts into neurons.

Figure 16:
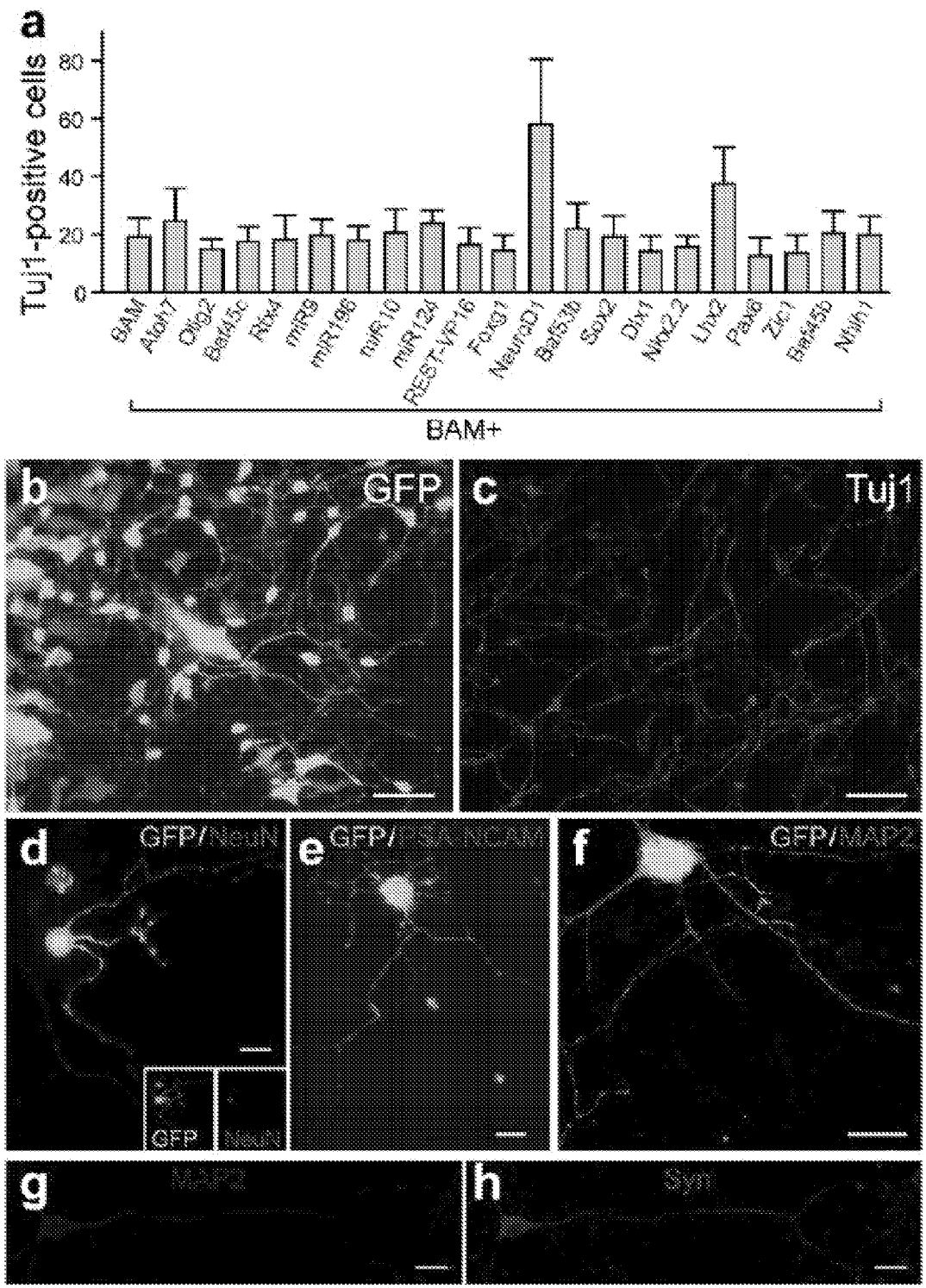
FIG. 16. NeuroD1 increases reprogramming efficiency in primary human fetal fibroblasts. a, Frequency of Tuj1-positive cells per 20-field displaying neuronal morphologies after infection of HFF with BAM factors on combination with the indicated candidate factors. Each well (3.8 cm² surface area) of the 12 well-plates contained 125,000 cells at the plating stage. b-f, Fourteen days after infection, BAM+NeuroD1 iN cells exhibited stereotypical neuronal morphologies (b) and expressed the pan-neuronal markers Tuj1 (c), NeuN (d), PSA-NCAM (e) and MAP2 (f). g-h, A fibroblast-derived iN cell labeled with antibodies against MAP2 (g) and synapsin (h) 4 weeks after infection and co-cultured with primary astrocytes. No neuronal cells were seen in parallel pure astrocyte cultures from the same preparation. Scale bars: 100 µm (b, c), 10 µm (d-h).

We therefore screened additional factors in combination with the BAM pool, and determined the frequency of Tuj1-positive cells displaying a neuronal morphology. Strikingly, NeuroD1, another basic helix-loop-helix factor, improved the efficiency of generating Tuj1-positive neuronal cells by more than two-fold when analyzed 21 days after infection (FIG. 16a). The LIM homeodomain transcription factor Lhx2 also slightly improved the efficiency. Independent experiments confirmed the beneficial effect of NeuroD1, but the effect of Lhx2 remained marginal (data not shown). The BAM+NeuroD1 (BAMN) iN cells exhibited neuronal morphologies 2 weeks after infection and expressed various pan-neuronal markers such as Tuj1, MAP2, PSA-NCAM, and NeuN (FIG. 16b-f). However, the vast majority of cells were negative for synapsin, a marker of more mature neurons. When cultured in the presence of primary astrocytes and in media conditions facilitating synapse formation, a few cells began to express synapsin 4 weeks after infection (FIGS. 16g and h).

Figure 17:
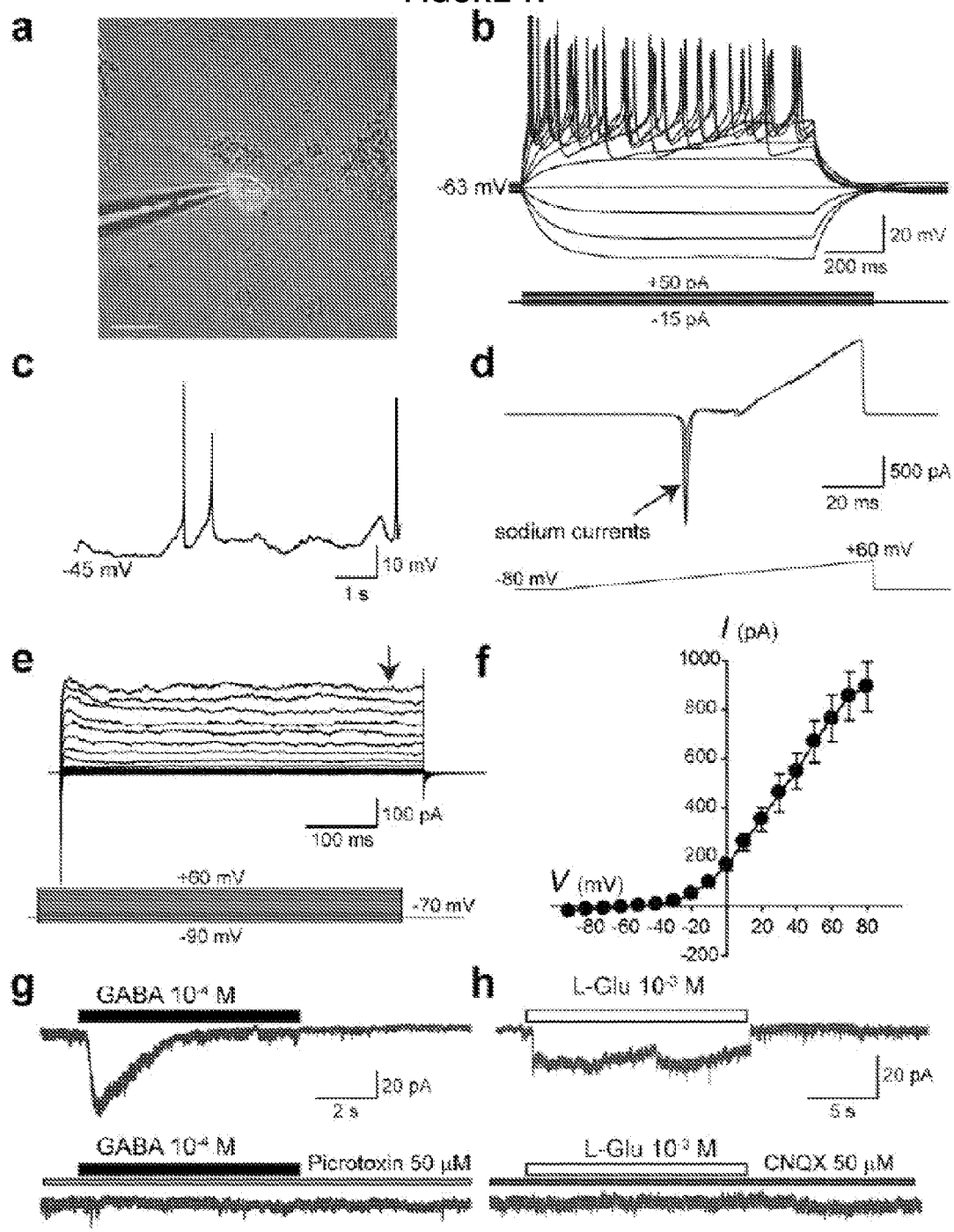
FIG. 17. Membrane properties of HFF-iN cells. a, Patch clamp recording was conducted on HFF-iN cells identified by EGFP fluorescence and DIC microcopy. b, Representative traces of membrane potentials in response to step current injections (low panel) from an HFF-iN cells 19 days after infection. Membrane potential was maintained at −63 mV. c, Spontaneous action potentials recorded from an iN cell 25 days after infection. d, Representative traces of membrane currents recorded following application of a 100 ms ramp protocol from −80 mV to +60 mV (lower panel). Fast activating and inactivating Na+ currents were prominent. Three traces are shown superimposed from the same cell as shown in (c). e, Representative traces of whole-cell currents measured in voltage-clamp mode. Cell was held at −70 mV, voltage was increased stepwise from −90 mV to +60 mV in 10 mV intervals. f, Current-voltage relationship of outward whole-cell currents recorded from iN cells. Currents were measured at 50 ms before the end of the pulse (arrow indicated in e). Cells were held at −70 mV, 500 ms durations of voltage steps from −90 mV to +80 mV, at 10 mV intervals, were applied (n=3). g, Inward current response following application of $10^{-4}$M GABA from a pipette using a picospritzer (n=4); lower trace shows that application of picrotoxin, a specific antagonist of $GABA_A$ receptors, blocks the GABA-induced current response. The internal solution contained ~135 mM Cl explaining the inward current response. Cells were held at −70 mV. h, Inward current responses following application of $10^{-3}$M L-glutamate from a pipette using a picospritzer (n=4). Lower panel indicates that glutamate induced current response could be blocked by CNQX, a specific antagonist of AMPA receptors. Cells were held at −70 mV. Scale bar in (a) represents 10 µm.

We next asked if these BAMN HFF-iN cells exhibit functional properties similar to human neurons. Neuronal cells were identified by morphology using EGFP fluorescence and differential interference contrast microscopy (FIG. 17a). Whole-cell recordings were performed 14 to 35 days after infection. The average resting membrane potential of these neuronal like cells was ~−52 mV (n=41) at 2 to 4 weeks after induction. Strikingly, when cells were step depolarized, they fired repetitive action potentials (FIG. 17b). In some cases, spontaneous action potentials were also observed (FIG. 17c). We then examined the whole-cell currents in voltage-clamp mode and recorded fast-activating and inactivating Na+ currents as well as outward currents, representing Na+- and K+ currents, respectively (FIG. 17d-f). These data indicate that the BAMN pool can convert primary human fibroblast cultures into cells with active membrane properties similar to neurons.

Figure 18:
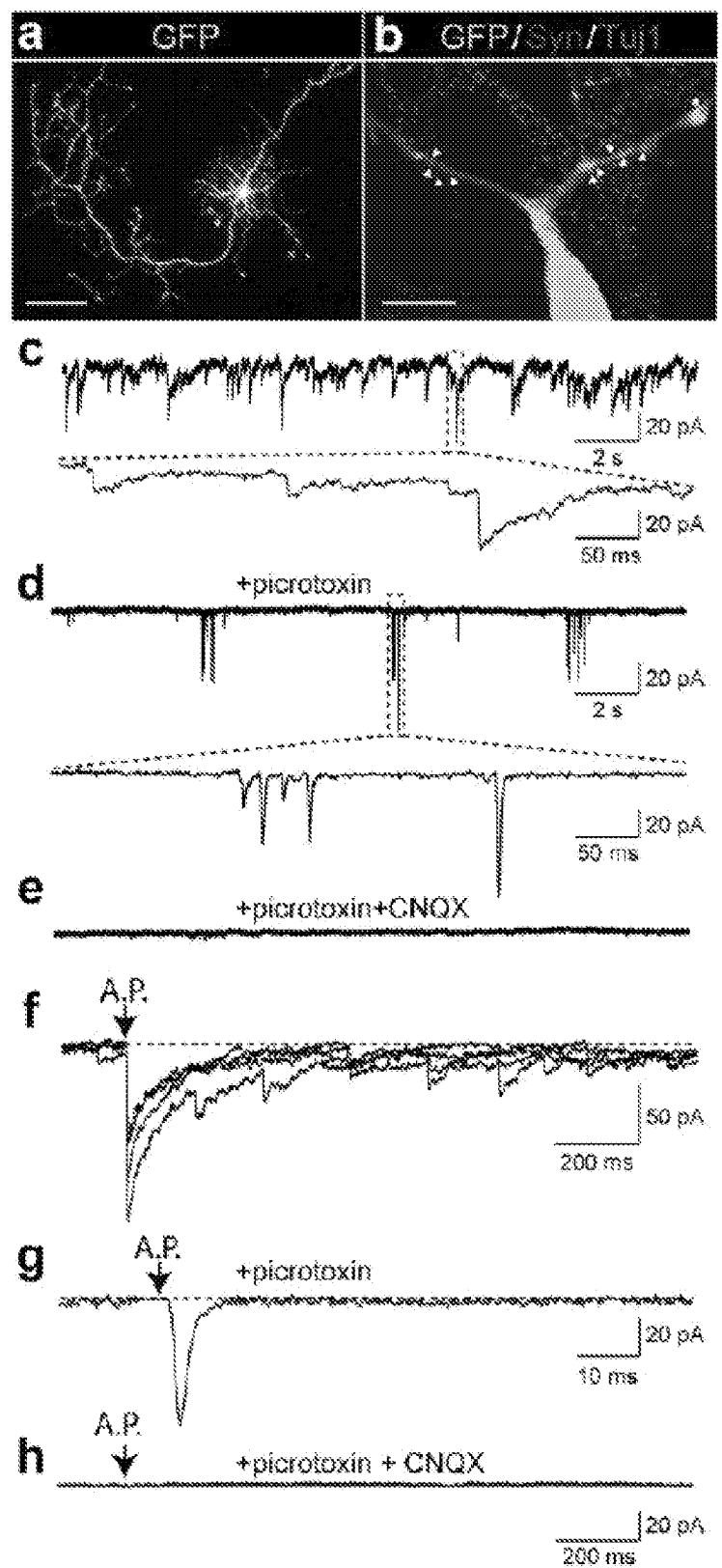
FIG. 18. Synaptic responses of HFF-iN cells. a, An HFF-iN cell with complex dendrite arborization and expressing EGFP co-cultured with mouse cortical neurons at day 35 after viral infection. b, Immunofluorescence image showing synaptic puncta, visualized with an antibody against synapsin. Synapses colocalize with neurites extending from HFF iN cells (arrow heads). c, Thirty-five days after viral infection spontaneous postsynaptic currents (PSCs) were recorded in HFF iN cells. The slow kinetics of the responses (see insert) indicated that the majority of these responses were GABAergic. d, These slow responses could be blocked by perfusion with picrotoxin. In this condition, bursting events of picrotoxin-resistant EPSCs were recorded. The insert shows the fast kinetics of these bursting postsynaptic responses. e, In the presence of picrotoxin and CNQX, no spontaneous activities were observed. f, Evoked postsynaptic current responses with mostly slow kinetics (see time scale). A.P.=action potential. g, In the presence of picrotoxin, also evoked fast-kinetic excitatory PSCs (EPSCs) could be revealed. h, No evoked synaptic responses were observed in the presence of picrotoxin and CNQX indicating that the postsynaptic currents were mediated by $GABA_A$ and AMPA receptors. Postsynaptic responses, either spontaneous or evoked, were recorded from a total of 11 cells from 3 independent experiments. Scale bars: 100 μm (a); 10 μm (b).

Next we asked whether BAMN-iN cells expressed functional neurotransmitter receptors a key prerequisite for synaptic transmission. Application of either GABA or L-glutamate through a pipette using picospritzer induced current responses which could be blocked by the channel inhibitors picrotoxin and CNQX, respectively (FIGS. 17g and h). We then explored if these HFF-iN cells could form functional synapses and integrate into preexisting neuronal networks. To that end, we dissociated the fibroblasts four days after infection with the BAMN factors and EGFP and plated them onto previously established primary mouse cortical cultures in conditions that promote synapse formation (see Methods). These co-cultures were maintained up to 5 weeks. Human iN cells could be readily distinguished from mouse neurons by virtue of their EGFP expression (FIG. 18a). Immunostaining with synapsin antibodies showed scattered synaptic puncta on the neurites of EGFP-positive cells (FIG. 18b). At 4 to 5 weeks of co-culture, whole cell recordings demonstrated that human iN cells exhibited spontaneous postsynaptic currents (PSCs) with variable kinetics (FIG. 18c). When the GABAA receptor inhibitor picrotoxin was added to the culture, the majority of PSCs were blocked demonstrating that the majority of postsynaptic events were inhibitory (IPSCs) (FIG. 18d). The picrotoxin-resistant PSCs were abolished by further addition of the AMPA receptor blocker CNQX, verifying that these bursting PSCs were excitatory (EPSCs) and mediated by glutamate receptors (FIG. 18e). Focal stimulation through a bipolar electrode evoked slow kinetic synaptic responses which could be blocked by picrotoxin (FIG. 18f) again indicating that the majority of the responses were mediated by GABAA receptors. In addition, evoked EPSC could be recorded in this condition (FIG. 18g) which were sensitive to further addition of CNQX (FIG. 18h). These results indicate that HFF-iN cells can functionally integrate into neuronal networks and form excitatory and inhibitory synaptic contacts, a principal property of neurons.

The results of this study highlight the power of lineage-specific transcription factors to induce specific cell fates in somatic and pluripotent cells. Currently, one important limitation of the potentially broad applications of iPS cell technology is the variability and length of available differentiation protocols. We propose ES-iN cells or iPS-iN cells as valuable alternative approach to generate functional neuronal cells from pluripotent stem cells in a rapid and reliable way extending previous work utilizing transcription factors to enhance ES cell differentiation. Compared to our previous experience with mouse fibroblasts, the conversion of human fibroblasts into neuronal cells was less efficient and robust.

Methods

Cell culture. H9 human ES cells were obtained from WiCell Research Resources and expanded in mTeSR1 (Stem Cell Technologies). Cells were routinely split with dispase every 4 to 5 days and seeded as small clumps on matrigel (Invitrogen). The day before infection, cells were treated with accutase and seeded as single cells in 3.5 cm tissue culture dishes on matrigel in mTeSR1 containing 2 μM Thiazovivin (Bio Vision) as described in Xu et al. Approximately $1\text{-}2\cdot 10^5$ cells were seeded in a single dish. Primary human fetal fibroblasts were isolated from the distal half of the leg of a GW9 embryo obtained from Advanced Bioscience Resources Inc. The tissue was dissociated to small clumps using scissors before being digested in 0.25% trypsin for 10 minutes at 37° C. and plated in MEF media (DMEM high glucose, calf serum, sodium pyruvate, non-essential amino acids, penicillin/streptomycin and β-mercaptoethanol). Before being used for experiments, primary cells were passaged 3-6 times. Primary mouse cortical cultures and glial monolayer cultures were established as described previously.

Characterization of primary human fibroblast culture. To exclude potential rare neural precursor cells in the primary fibroblast cultures we screened a number of marker proteins and transcripts by immunofluorescence and RT-PCR. Each antibody and primer pair was validated in the same reaction using an appropriate positive control. We included antibodies recognizing antigens of neural stem cells (SOX2, BRN2) and markers for neurons and astroglia (Tuj1, MAP2, GFAP). Cells were analyzed following culture in regular fibroblast medium (MEF medium) and in N3 media supplemented with EGF and FGF2 for 12 days (a condition promoting neural progenitor cell expansion). No positive cells were detected out of at least 100,000 passage 5 fibroblasts screened for any marker. In addition, using RT-PCR we could not detect the expression of either GFAP, MUSASHI1, p75, PAX6, or WNT1. Primers were validated on positive control cDNA from human embryonic stem cell derived neurons, neural stem cells, and neural crest stem cells. In contrast, two independent GAPDH primer pairs showed robust RT-dependent amplification.

Lentiviral Infections. Lentiviral production and fibroblast infections were performed as described previously. Briefly, primary human fetal fibroblasts were plated on poly-ornithine coated dishes and infected with lentiviral supernatant and polybrene (8 µg/µL) in fresh MEF media. Viral media was removed after 16-24 hours and replaced with MEF media containing doxycycline (2 µg/µL). After 24-48 hours, media was changed to N3 media (DMEM/F2 (Invitrogen), apotransferrin (100 µg/ml), insulin (5 µg/ml), sodium selenite (30 nM), progesterone (20 nM), putrescine (100 nM), penicillin/streptomycin) containing doxycycline (2 µg/µL). For human ES cell infections, H9 human embryonic stem cells were switched into N3 media containing polybrene (2 µg/µL) 24-48 hours after re-plating, and concentrated lentiviral particles were added. After 16-24 hours, cultures were switched into N3 media containing doxycycline (2 µg/µL) and changed daily before dissociation. Forty-eight hours after the initial addition of doxycycline, Ara-C (4 µg/µL) was added to the media to inhibit proliferation of ES cells. Infected ES cultures were dissociated with papain 24-48 hours after addition of Ara-C (d4-d5 post infection) and replated onto monolayer glial cultures in neuronal growth medium 12 containing Ara-C (2 µg/µL). All chemicals were purchased from Sigma if not otherwise specified.

Molecular cloning and virus production. Complementary DNAs for the transcription factors were reverse transcribed and PCR amplified from RNA extracted from the developing mouse brain and spinal cord or DNA plasmids as templates were purchased from Open Biosystems and cloned into FUW-based lentiviral constructs under the control of the tetracycline operator. Replication-incompetent, VSVg-coated lentiviral particles were packaged in HEK293T cells following transfection with calcium phosphate precipitation as described. HFFs were infected with viral supernatant. For ES cell infections, the virus was concentrated by ultracentrifugation (Beckman; 25,000 RPM, 90 min). The microRNA expression plasmids (hsa-miR-9, -10a, -124a and -196a) contained the short hair-pin sequences of indicated hsa-miRNAs under the transcriptional control of human U6 promoter which were cloned into FG12 vector upstream of a Ubiquitin C-EGFP expression cassette.

Electrophysiology. Cells were analyzed at indicated time points after infection. Action potentials were recorded with current-clamp whole-cell configuration. The pipette solution for current-clamp experiments contained (in mM): 123 K-gluconate, 10 KCl, 1 $MgCl_2$, 10 HEPES, 1 EGTA, 0.1 $CaCl_2$, 1 $K_2ATP$, 0.2 $Na_4GTP$ and 4 glucose, pH adjusted to 7.2 with KOH. Membrane potentials were kept around −65 to −70 mV, and step currents were injected to elicit action potentials. For whole-cell voltage dependent current recordings, the same internal solution as above mentioned were used. For synaptic functional evaluation, the internal solution contained (in mM): CsCl 135, HEPES 10, EGTA 1, Mg-ATP 4, Na4GTP 0.4, and QX-314 10, pH7.4. The bath solution contained (in mM): NaCl 140, KCl 5, $CaCl_2$ 2, $MgCl_2$ 2, HEPES 10, and glucose 10, pH7.4. Whole-cell currents including Na+ and K+ currents were recorded at a holding potential of −70 mV, voltage steps ranging from −80 mV to +90 mV were delivered at 10 mV increments. Synaptic responses were measured as described previously.

Immunofluorescence and RT-PCR. For immunofluorescence experiments, cells were fixed in 4% paraformaldehyde in PBS for 10 minutes at room temperature. Antibodies were diluted to indicated concentrations (see below). Following fixation, cells were incubated in 0.2% Triton X-100 in PBS for 5 minutes at RT. After washing twice with PBS, cells were blocked in a solution of PBS containing 4% BSA and 1% cosmic calf serum (CCS) for 30 minutes at RT. Primary and secondary antibodies were diluted in a solution of PBS containing 4% BSA and 1% CCS. Primary and secondary antibodies were applied for 1 hour and 30 minutes, respectively. Cells were washed three times with PBS between primary and secondary staining. For cell counts, neuronal cells were defined as cells, which stained positive for Tuj1 and had a process at least 3 times longer than the cell body. The following antibodies were used for our analysis: rabbit-GFAP (DAKO, 1:4000), mouse anti-MAP2 (Sigma, 1:500), mouse anti-NeuN (Millipore, 1:200), mouse anti-Peripherin (Sigma, 1:100), mouse anti-Sox2 (R&D Systems, 1:50), rabbit anti-Tuj1 (Covance, 1:1000), mouse anti-Tuj1 (Covance, 1:1000), goat anti-Brn2 (clone C-20, Santa Cruz Biotechnology, 1:100), mouse anti-BrdU (Becton-Dickinson, 1:50), sheep anti-Tyrosine Hydroxylase (Pel-Freez, 1:500), rabbit anti-synapsin (clone E028, provided by T.C.S., 1:1000), guinea pig anti-vGLUT1 (Millipore, 1:2000), mouse anti-GAD6 (Developmental Studies Hybridoma Bank (DSHB), 1:500), Ascl1 (Abcam, 1:200). FITC-, and Cy3-conjugated secondary antibodies were obtained from Jackson Immunoresearch. Alexa-488, Alexa-546 and Alexa-633-conjugated secondary antibodies were obtained from Invitrogen. DAPI (Sigma, 1:10,000). For RT-PCR analysis, RNA was isolated using Trizol (Invitrogen) following the manufacturer's instructions, treated with DNAse (Invitrogen) and reverse-transcribed with Superscript II (Invitrogen).

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of the present invention is embodied by the appended claims.

That which is claimed is:

1. A method of converting non-neuronal cells into induced neuronal/oligodendrocytes/astrocytes/neural stem cells (iNs), the method comprising: contacting a population of non-neuronal somatic cells in vitro with a neuron reprogramming (NR) system consisting of reprogramming factors Asci1, Brn2 and Myt1I for a period of time sufficient to reprogram said non-neural cells, wherein a population of iNs is produced.

2. The method of claim 1, wherein the non-neuronal cells are mouse cells.

3. The method of claim 1, wherein the non-neuronal cells are human somatic cells.

4. The method of claim 1 wherein said induced neural cells are induced oligodendrocytes.

5. The method of claim 1, wherein said induced neural cells are induced astrocytes.

6. The method of claim 1, wherein said induced neuronal cells are induced neural progenitor cells.

7. The method of claim 1, wherein the efficiency of reprogramming said somatic cells to become iNs is at least about 0.1%.

8. The method of claim 1, further comprising the steps of:
combining the NR system-contacted population with a reagent that specifically recognizes a marker associated with cells of the neuronal lineage;
selecting for cells that express said marker associated with cells of the neuronal lineage to provide a selected cell population;
wherein the population that is produced is an enriched population of IN cells.

9. The method of claim 8, wherein the selecting step is effected by flow cytometry (FACS).

10. The method of claim 8, wherein the selecting step is effected by magnetic activated cell sorting (MACS).

11. The method of claim 8, wherein the marker associated with cells of the neuronal lineage is Poly-Sialated Neural Cell Adhesion Molecule (PSA-NCAM).

12. A method of converting fibroblast cells into induced neuronal/oligodendrocytes/astrocytes/neural stem cells (iNs), the method comprising:
contacting a population of fibroblast cells in vitro with a neuron reprogramming (NR) system consisting of reprogramming factors Asci1, Brn2, Myt1I, for a period of time sufficient to reprogram said fibroblast cells, wherein a population of iNs is produced.

13. The method of claim 12, wherein the fibroblast cells are mouse cells.

14. The method of claim 12, wherein said induced neuronal cells are iNs.

15. The method of claim 12, wherein the efficiency of reprogramming fibroblast cells to become iNs is at least about 0.1%.

16. The method of claim 12, further comprising the steps of:
combining the NR system-contacted population with a reagent that specifically recognizes a marker associated with cells of the neuronal lineage; selecting for cells that express said marker associated with cells of the neuronal lineage to provide a selected cell population; wherein the population that is produced is an enriched population of iNs.

17. The method of claim 16, wherein the selecting step is effected by flow cytometry (FACS).

18. The method of claim 16, wherein the selecting step is effected by magnetic activated cell sorting (MACS).

19. The method of claim 16, wherein the marker associated with cells of the neuronal lineage is Poly-Sialated Neural Cell Adhesion Molecule (PSA-NCAM).

20. A method of converting fibroblast cells into induced neuronal/oligodendrocytes/astrocytes/neural stem cells (iNs), the method comprising: contacting a population of human fibroblast cells in vitro with a neuron reprogramming (NR) system consisting of reprogramming factors Asci1, Brn2, Myt1I and NeuroD, for a period of time sufficient to reprogram said fibroblast cells, wherein a population of iNs is produced.

* * * * *

SEQUENCE LISTING

```
<160> NUMBER OF SEQ ID NOS: 7

<210> SEQ ID NO 1
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 1

Arg Gln Ile Lys Ile Trp Phe Gln Asn Arg Arg Met Lys Trp Lys Lys
 1               5                  10                  15

<210> SEQ ID NO 2
<211> LENGTH: 20
<212> TYPE: DNA
<213> ORGANISM: Artificial Sequence
<220> FEATURE:
<223> OTHER INFORMATION: Synthetic primer

<400> SEQUENCE: 2
tcgagccctt ctcacttgtt                                               20

<210> SEQ ID NO 3
<211> LENGTH: 20
<212> TYPE: DNA
<213> ORGANISM: Artificial Sequence
<220> FEATURE:
<223> OTHER INFORMATION: Synthetic primer

<400> SEQUENCE: 3
ttgatgcatt ttgggggtat                                               20

<210> SEQ ID NO 4
<211> LENGTH: 20
<212> TYPE: DNA
<213> ORGANISM: Artificial Sequence
<220> FEATURE:
<223> OTHER INFORMATION: Synthetic primer

<400> SEQUENCE: 4
gaactgggca aggtcaagaa                                               20

<210> SEQ ID NO 5
<211> LENGTH: 20
<212> TYPE: DNA
<213> ORGANISM: Artificial Sequence
<220> FEATURE:
<223> OTHER INFORMATION: Synthetic primer

<400> SEQUENCE: 5
cgcttgtcac tttcgttcag                                               20

<210> SEQ ID NO 6
<211> LENGTH: 21
<212> TYPE: DNA
<213> ORGANISM: Artificial Sequence
<220> FEATURE:
<223> OTHER INFORMATION: Synthetic primer
```

```
<400> SEQUENCE: 6
cgtgggccgc cctaggcacc a                                        21

<210> SEQ ID NO 7
<211> LENGTH: 18
<212> TYPE: DNA
<213> ORGANISM: Artificial Sequence
<220> FEATURE:
<223> OTHER INFORMATION: Synthetic primer

<400> SEQUENCE: 7
cttagggttc aggggggc                                            18
```